United States Patent
Zasloff et al.

[11] Patent Number: 5,856,535
[45] Date of Patent: Jan. 5, 1999

[54] AMINOSTEROL ESTER COMPOUNDS

[75] Inventors: Michael Zasloff, Merion Station; William Kinney, Richboro; Steven Jones, West Chester, all of Pa.

[73] Assignee: Magainin Pharmaceuticals, Inc., Plymouth Meeting, Pa.

[21] Appl. No.: 769,689

[22] Filed: Dec. 18, 1996

Related U.S. Application Data

[63] Continuation-in-part of Ser. No. 290,826, Aug. 18, 1994, Pat. No. 5,637,691, Ser. No. 416,883, Apr. 20, 1995, Pat. No. 5,733,899, and Ser. No. 483,059, Jun. 7, 1995.

[51] Int. Cl.$^6$ ..................... C07J 41/00
[52] U.S. Cl. ................ 552/521; 540/106
[58] Field of Search ............. 552/521; 540/106

[56] References Cited

U.S. PATENT DOCUMENTS

| | | |
|---|---|---|
| 3,016,390 | 1/1962 | Counsell . |
| 3,246,019 | 4/1966 | Freiberg et al. ............ 552/521 |
| 3,370,070 | 2/1968 | Klimstra et al. . |
| 4,220,598 | 9/1980 | Hixson, Jr. et al. ............ 424/1 |
| 4,372,888 | 2/1983 | Hjelmeland ............ 260/397.1 |
| 4,425,273 | 1/1984 | Iida et al. ............ 262/397.1 |
| 4,514,393 | 4/1985 | Castagnola et al. ............ 260/397.1 |
| 4,545,938 | 10/1985 | Mosbach et al. ............ 260/397.1 |
| 4,550,163 | 10/1985 | Voss et al. ............ 544/244 |
| 4,565,811 | 1/1986 | DiSchiena ............ 514/182 |
| 4,771,042 | 9/1988 | Braughler et al. . |
| 4,793,948 | 12/1988 | Hatono et al. ............ 260/397.1 |
| 4,966,897 | 10/1990 | Angelastro et al. ............ 514/177 |
| 4,994,443 | 2/1991 | Folkman et al. . |
| 5,001,116 | 3/1991 | Folkman et al. . |
| 5,004,737 | 4/1991 | Kim et al. . |
| 5,039,529 | 8/1991 | Bergendal et al. . |
| 5,057,509 | 10/1991 | Pellicciari et al. ............ 514/182 |
| 5,061,701 | 10/1991 | Pellicciari et al. ............ 514/182 |
| 5,063,222 | 11/1991 | Komoto et al. ............ 514/180 |
| 5,075,464 | 12/1991 | Blohm et al. ............ 552/522 |
| 5,135,919 | 8/1992 | Folkman et al. . |
| 5,192,756 | 3/1993 | Zasloff et al. . |
| 5,250,524 | 10/1993 | Kramer et al. . |
| 5,646,316 | 7/1997 | Jacobsen et al. ............ 552/521 |

FOREIGN PATENT DOCUMENTS

| | | |
|---|---|---|
| 0394971 | 10/1990 | European Pat. Off. . |
| 0466315 | 1/1992 | European Pat. Off. . |
| 2361899 | 3/1978 | France . |
| 1565351 | 4/1980 | United Kingdom . |
| WO 87/02367 | 4/1987 | WIPO . |
| WO 91/19731 | 12/1991 | WIPO . |
| 93/25197 | 12/1993 | WIPO . |
| 94/19366 | 9/1994 | WIPO . |
| WO 94/20520 | 9/1994 | WIPO . |

OTHER PUBLICATIONS

K.S. Moore et al., "Squalamine: An aminosterol antibiotic from the shark," *Proc. Natl. Acad. Sci. USA* vol. 90, Feb. 1993, pp. 1354–1358.

A.M. Bellini, et al., "Antimicrobial Activity of Basic Cholane Derivatives Part IX," *Arch. Pharm.* (Weinheim), vol. 323, 1990, pp. 201–205.

A.M. Bellini et al., "Antimicrobial Activity of Basic Cholane Derivatives X," *Steroids*, vol. 56, Jul. 1991, pp. 395–397.

J. McKenna et al., "Bis–steroids as Potential Enzyme Models," *J.C.S. Chem. Comm.*, 1977, pp. 809–811.

S.L. Wehrli et al., "Structure of the novel steroidal antibiotic squalamine determined by two–dimensional NMR spectroscopy," *Steroids*, vol. 58, No. 8, Aug. 1993.

A Sadownik et al., "Rapid Construction of a Squalamine Mimic," *Journal of the American Chemical Society*, vol. 117, 1995, pp. 6138–6139.

(List continued on next page.)

*Primary Examiner*—Rebecca Cook
*Attorney, Agent, or Firm*—Finnegan, Henderson, Farabow, Garrett & Dunner, L.L.P.

[57] ABSTRACT

An aminosterol compound according to the following formula:

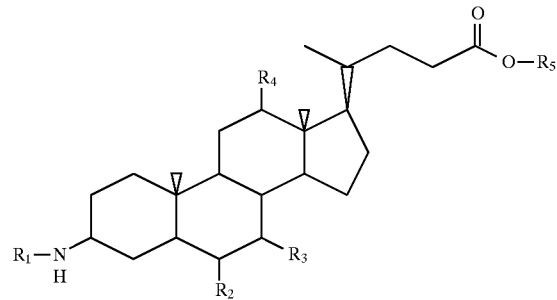

wherein:
$R_1$ is a member selected from the group of:

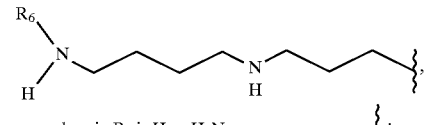

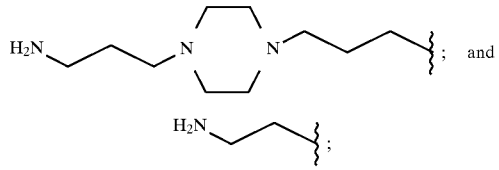

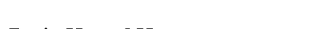

$R_2$ is H or OH;
$R_3$ is H or OH;
$R_4$ is H or OH; and
$R_5$ is a $C_1$ to $C_{12}$ alkyl group.

Preferably, $R_5$ is a $C_1$ to $C_6$ alkyl group, and a methyl group is particularly preferred.

15 Claims, No Drawings

OTHER PUBLICATIONS

R. Crum et al., "A New Class of Steroids Inhibits Angiogenesis in the Presence of Heparin or a Heparin Fragment," *Science*, vol. 230, Dec. 20, 1985, pp. 1377–1388.

W. Auerbach et al., "Angiogenesis Inhibition: A Review," *Pharmac. Ther.*, vol. 63, 1994, pp. 266–311.

A. Gagliardi et al, "Inhibition of Angiogenesis by Antiestrogens," *Cancer Research*, vol. 53, Feb. 1, 1993, pp. 533–535.

Moriarty, R.M., et al., "Synthesis of Squalamine. A Steroidal Antibiotic from the Shark," *Tetrahedron Letters*, vol. 35, No. 44, 31 Oct. 1994, pp. 8103–8106.

AMINOSTEROL ESTER COMPOUNDS

This application is a continuation-in-part of U.S. patent appl. Ser. No. 08/290,826, filed Aug. 18, 1994 now U.S. Pat. No. 5,637,691; U.S. patent appl. Ser. No. 08/416,883, filed Apr. 20, 1995; and U.S. patent appl. Ser. No. 08/483,059, filed Jun. 7, 1995. Each of these U.S. patent applications is entirely incorporated herein by reference.

FIELD OF THE INVENTION

The present invention relates to aminosterol ester compounds and pharmaceutical compositions containing such compounds.

BACKGROUND OF THE INVENTION

Various aminosterols have been discovered, and their use in various pharmacological applications has been disclosed. For example, as described in the above-noted patent applications, certain aminosterols have been found to selectively inhibit certain sodium proton exchangers ("NHE's") in cells. NHEs control various cellular properties and functions. For example, NHEs control cellular pH. It is critical that cells maintain an appropriate narrow pH range to assure that cell growth and certain body functions proceed in a suitable manner. If cells do not maintain an appropriate pH, severe health consequences, and even death can occur. Other aminosterols, such as squalamine described in the above-noted patent applications, have anti-angiogenic properties. Compounds that are anti-angiogenic typically are useful for treating cancers and other proliferative disorders. Compound 1436 has been found to have properties that indicate it will be useful in treating viral infections, such as HIV, SIV, and herpes.

Other aminosterols have been discovered or synthesized in addition to squalamine and compound 1436. More specifically, aminosterol esters have been produced and constitute the compounds according to this invention. Like squalamine and compound 1436, these aminosterol esters have interesting antibiotic properties and anti-proliferation properties for certain types of cells. The production and properties of these aminosterol esters will be discussed in more detail below.

BRIEF DESCRIPTION OF THE INVENTION

The present invention relates to aminosterol esters according to the following general formula:

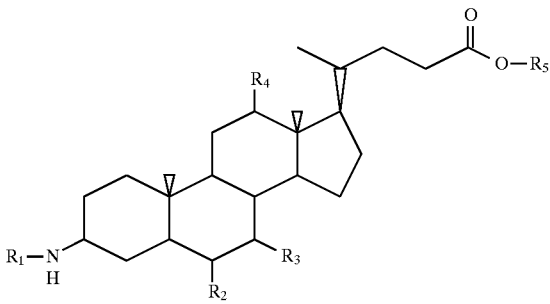

wherein:

$R_1$ is a member selected from the group consisting of:

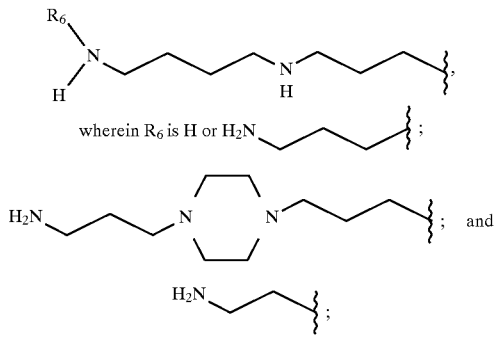

$R_2$ is H or OH;

$R_3$ is H or OH;

$R_4$ is H or OH; and $R_5$ is a $C_1$ to $C_{12}$ alkyl group.

The $R_5$ substituent group can be a $C_1$ to $C_{12}$ alkyl group, as noted above. Preferably, the $R_5$ group is a $C_1$ to $C_6$ alkyl group. As one particularly preferred subclass of the above-noted aminosterol esters, it is preferred that the $R_5$ substituent group is a methyl group, i.e., a $C_1$ alkyl group.

The $R_2$, $R_3$, and $R_4$ substituent groups can be oriented either α or β to the steroid ring base. Likewise, the polyamine side chain ("—NH—$R_1$") also can be oriented either α or β to the steroid ring base.

Specific ester compounds according to this invention include the following compounds:

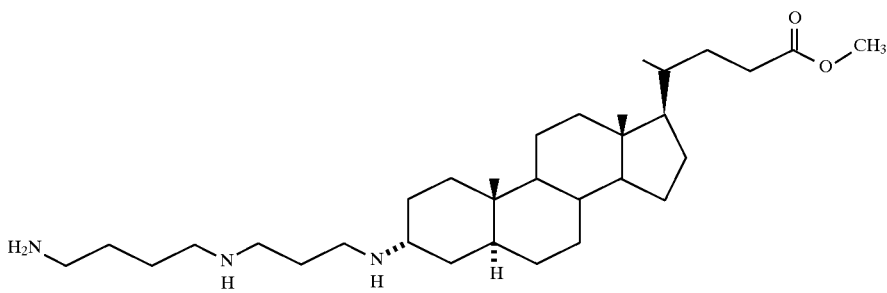

316

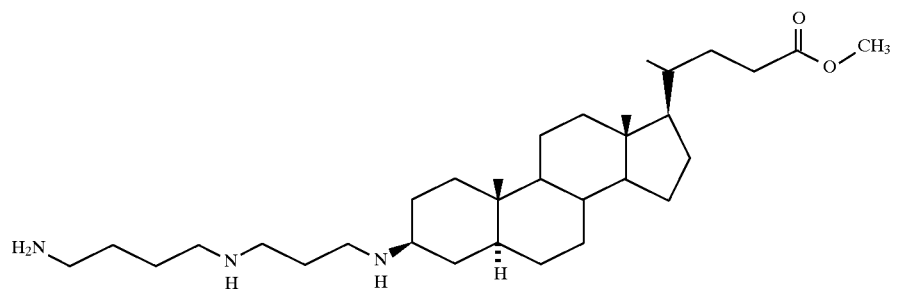
317
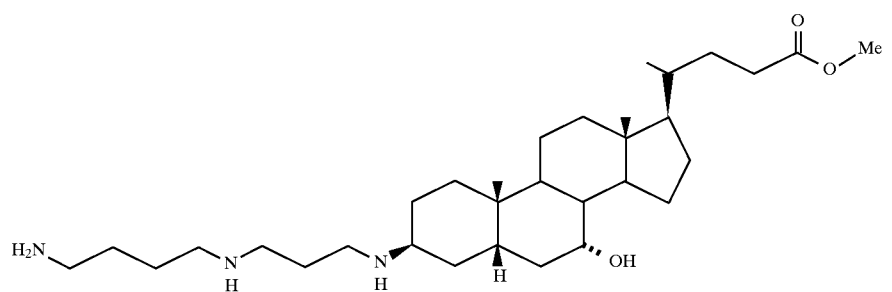
355
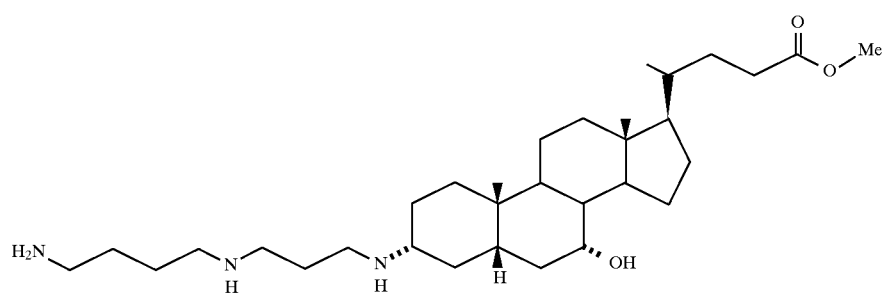
356
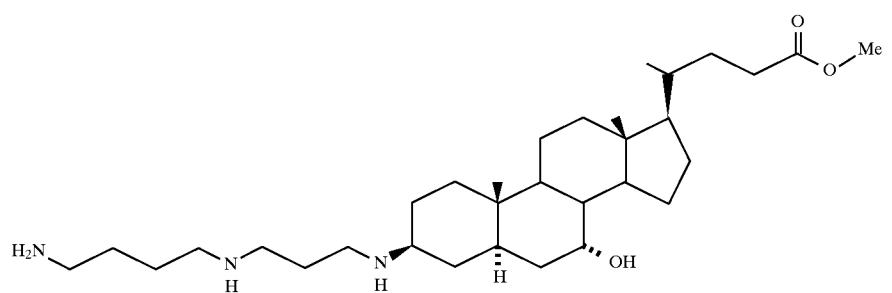
380
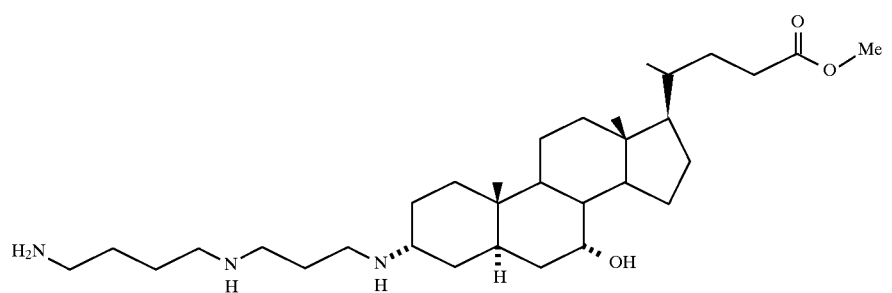
394

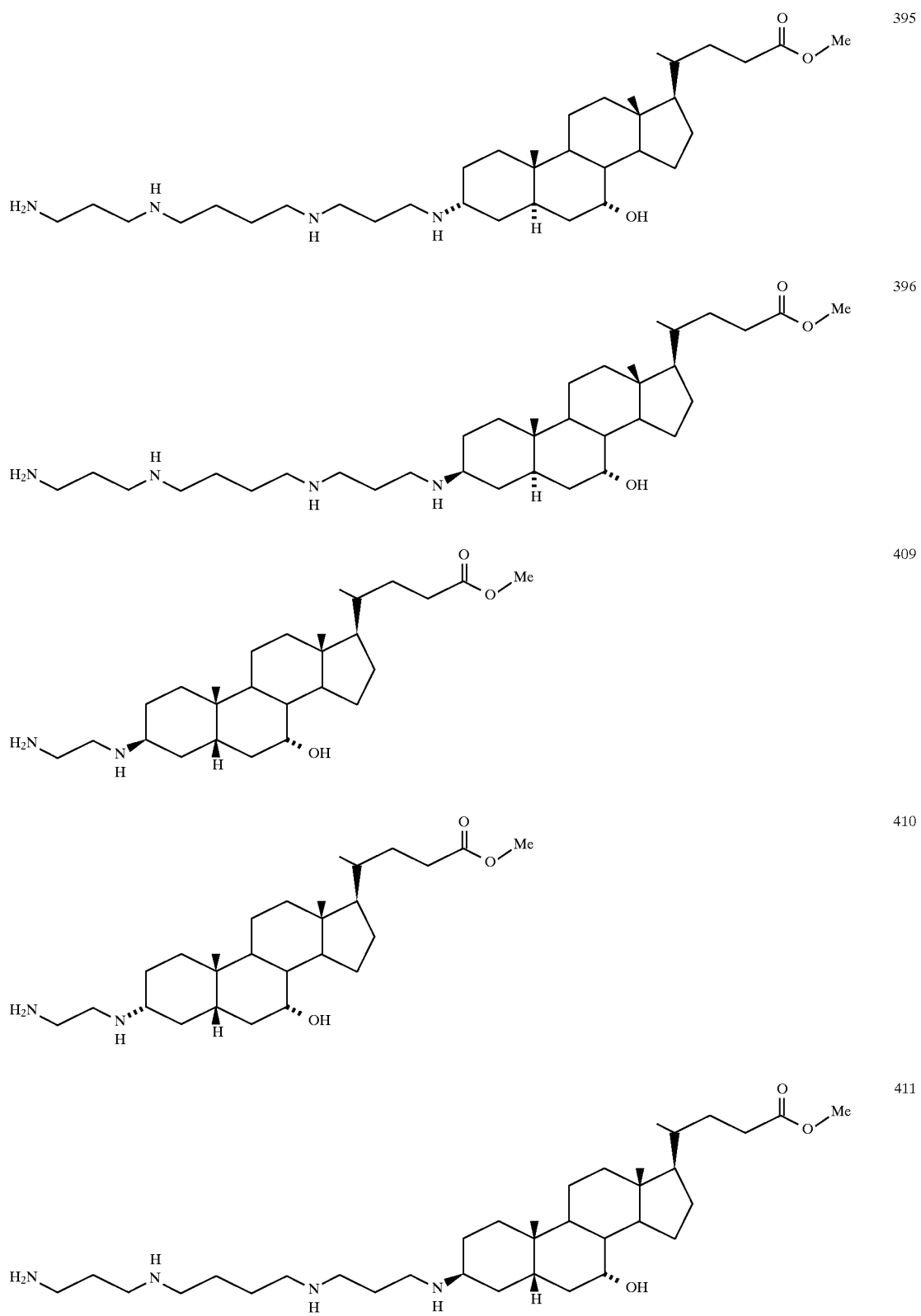

-continued
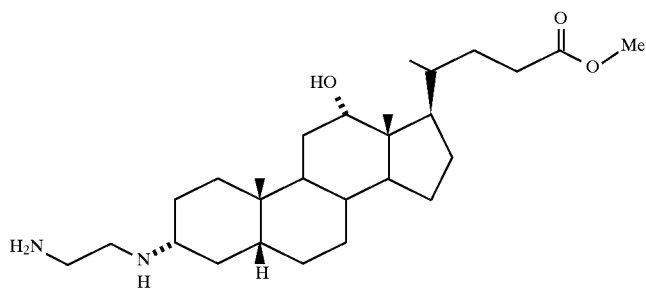
416
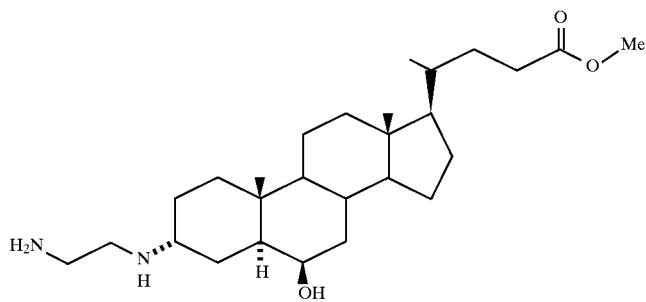
431
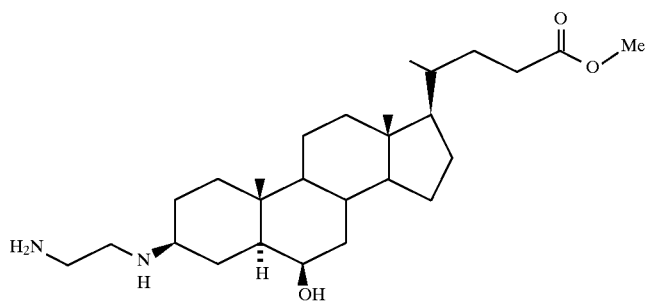
432
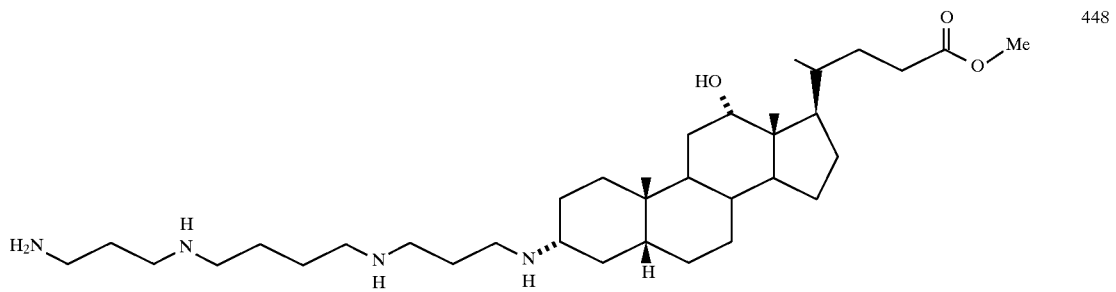
448
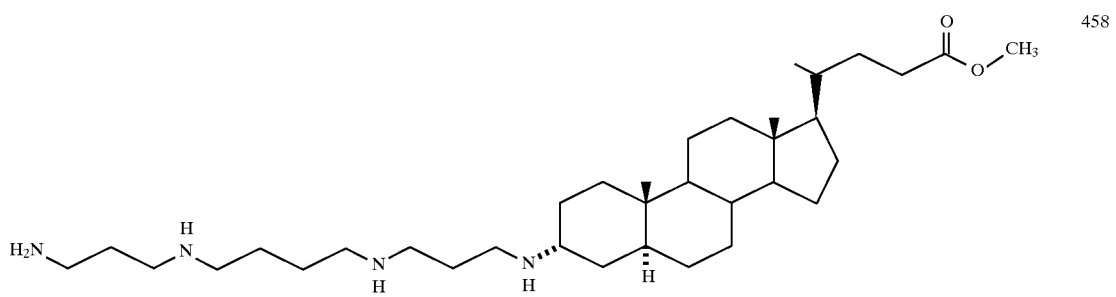
458

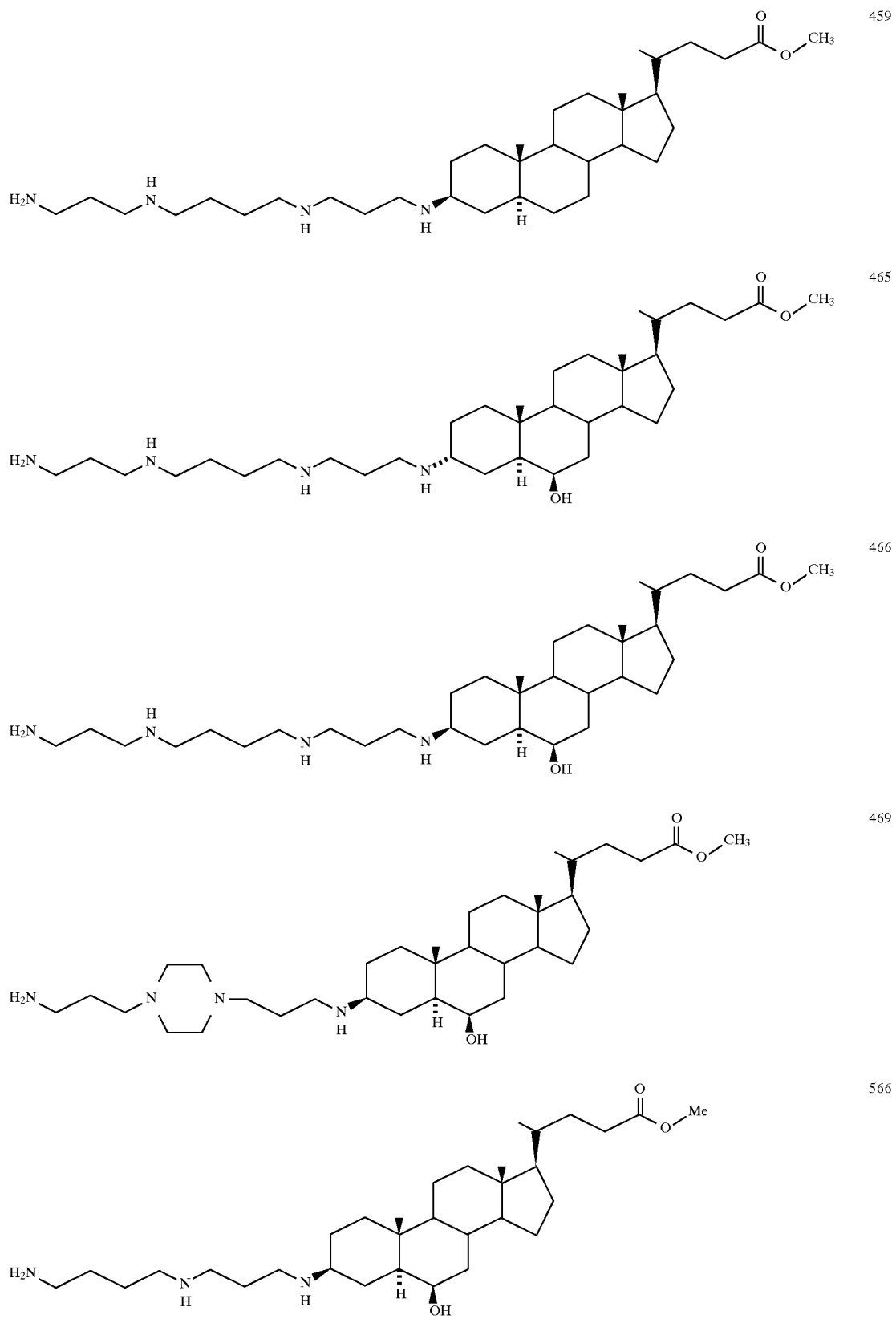

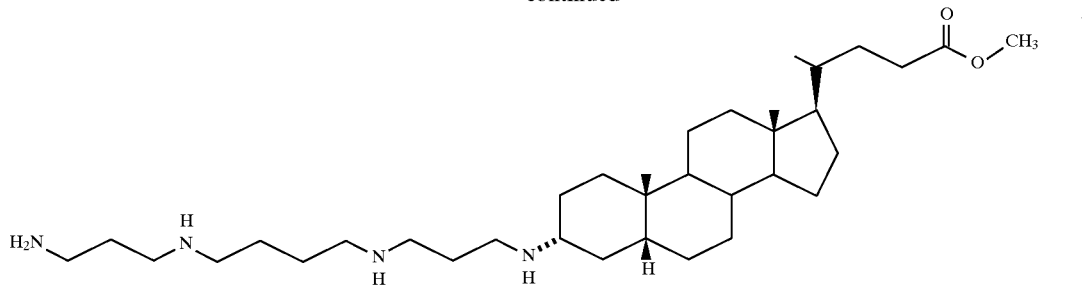

Other aspects, objects, and advantages of the invention will be apparent from the detailed disclosure below, which illustrates preferred features and embodiments of the invention. The specific examples described below should be construed as illustrating the invention and not as limiting the same.

DETAILED DESCRIPTION OF THE INVENTION

SYNTHESIS OF VARIOUS AMINOSTEROL COMPOUNDS

The steroid known as squalamine (also called "compound 1256" in this application) is the subject of U.S. Pat. No. 5,192,756 to Zasloff et al., the disclosure of which is entirely incorporated herein by reference. This compound is a broad-spectrum antibiotic, killing bacteria, fungi and protozoa. The total chemical synthesis of squalamine was reported in 1994, for example, in PCT Patent Publication No. WO 94/19366 (published Sep. 1, 1994), which document is entirely incorporated herein by reference.

EXAMPLE 1
Synthesis of Aminosterols

In addition to compound 1436 and squalamine, which were originally isolated from shark liver, synthetic aminosterol compounds have been developed. Various polyaminosterol compounds are described in U.S. patent appl. No. 08/416,883, which is the U.S. national phase of International Application No. PCT/US94/10265, filed Sep. 13, 1994. This PCT application is entirely incorporated herein by reference. The synthesis of various compounds is described in this related application, including the following:

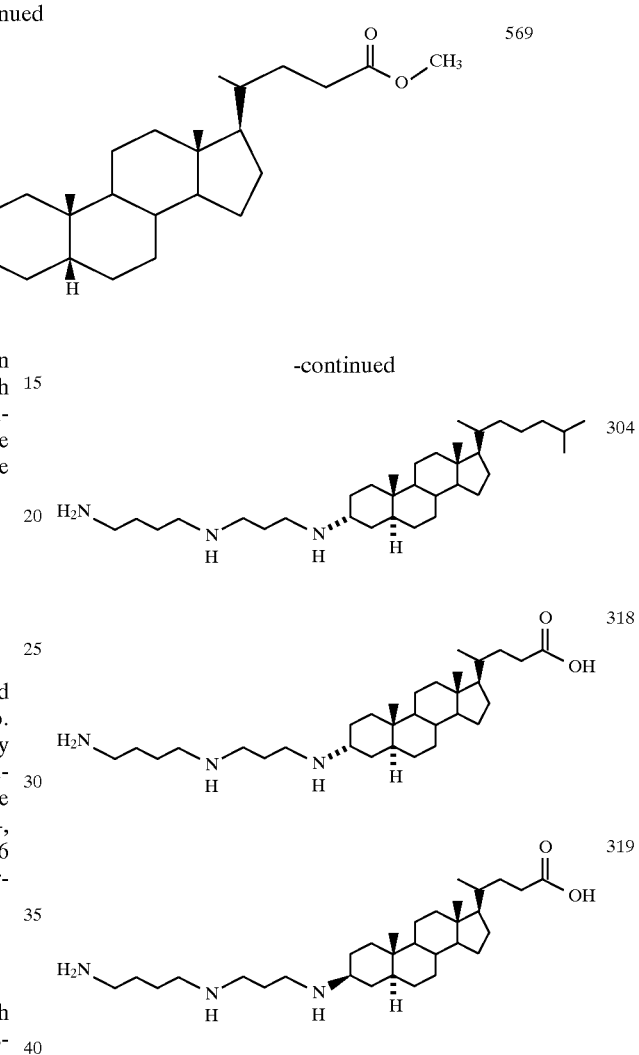

Additional aminosterol compounds have now been developed, including those exemplified below. The following describes the synthesis procedure for producing various aminosterol compounds, including aminosterols 303, 304, 318, and 319 identified above, as well as various aminosterol esters according to the invention.

Example A

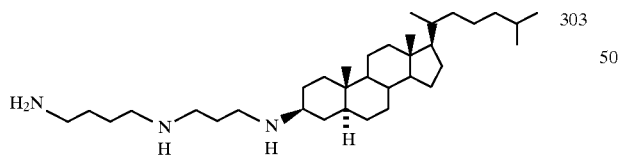

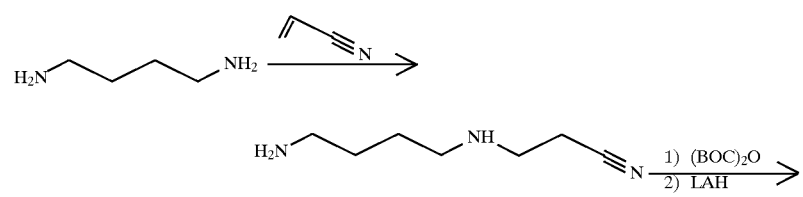

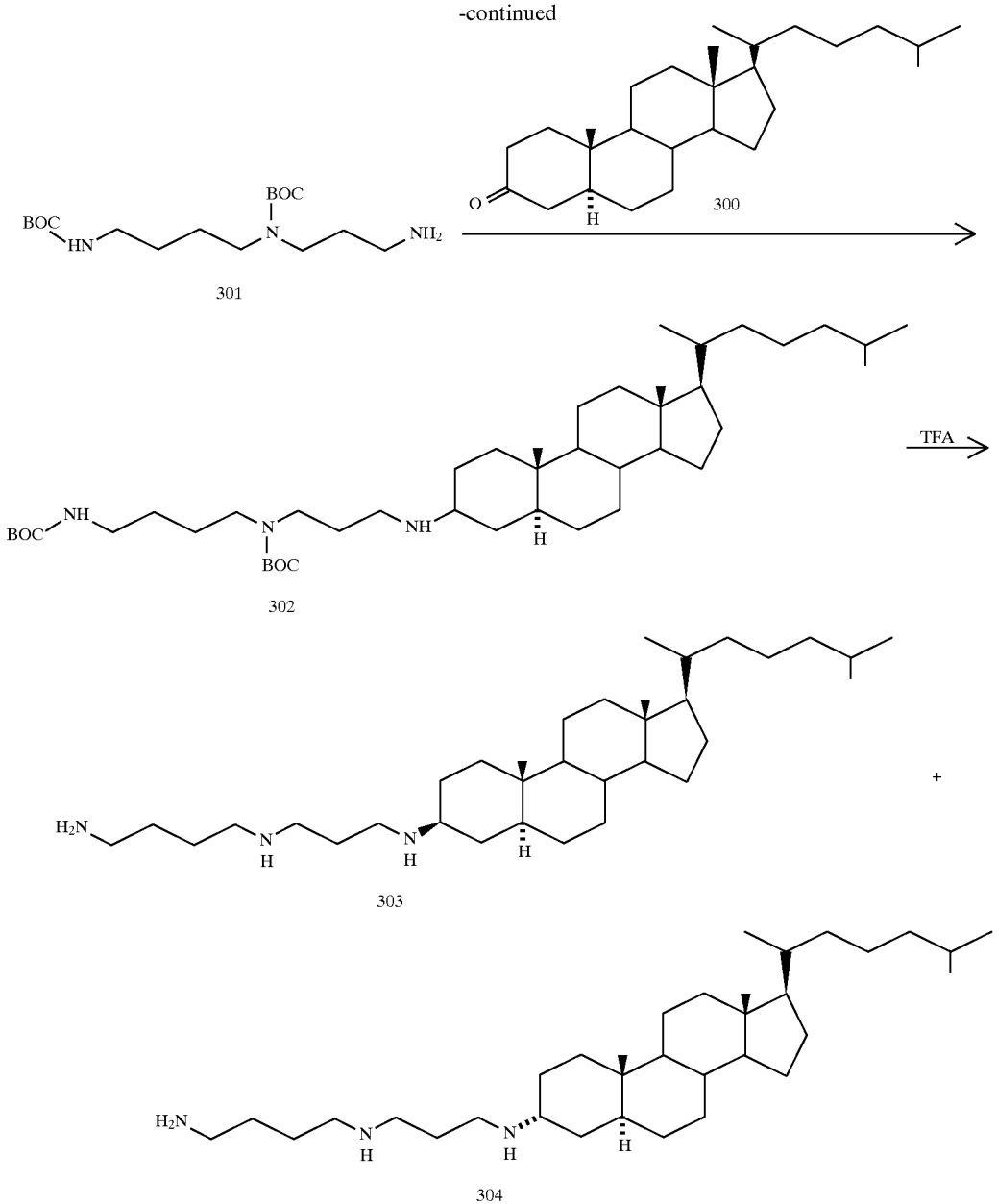

Preparation of compound 302: Reductive amination of 5α-cholestan-3-one produces a majority of the 3β-amino isomer (see M. H. Boutique, R. Jacquesy, *Bull. Soc. Chim.* (France), 1973, 750–753, which article is entirely incorporated herein by reference). A solution of 5α-cholestan-3-one 300 (898 mg, 2.32 mmol, available from Steraloids Inc. of New Hampshire) in dry tetrahydrofuran (10 ml) under nitrogen was treated with 3Å molecular sieves (5 g) and the triamine 301 (see K. Nakanishi et al., *Tetrahedron* 46 (9), 1990, 3267–3286, which article is entirely incorporated herein by reference) dissolved in dry methanol (25 ml). After 20 minutes at room temperature, sodium cyanoborohydride (696 mg, 11.0 mmol) was added, and the reaction mixture was stirred for four days, filtered through Celite® (a form of $SiO_2$ sold by Aldrich), and washed thoroughly with methanol and dichloromethane. After evaporation, the residue was partitioned between water (75 ml) and dichloromethane (75 ml), treated with 1N sodium hydroxide solution (15 ml) and brine (25 ml), and the layers were separated. The aqueous layer was extracted again with dichloromethane (75 ml), and the combined organics were dried ($Na_2SO_4$), filtered, and evaporated. The resulting colorless oil was dissolved in dichloromethane and applied to a flash column (4-cm diameter, gradient elution with 2.5–3.5% 2N methanolic ammonia (available from Aldrich) in dichloromethane). A mixture of 3α, β-amino isomers 302 was obtained (1.18 g, 71% yield) as a white foam. $^1$H NMR (200 MHz, $CDCl_3$) δ: 4.57 (br s, NH), 3.3–3.0 (m, 6H), 2.7–2.4 (m, 3H), 2.0–1.0 (m, 37H), 1.45 (s, 9H), 1.44 (s, 9H), 0.91–0.84 (m, 9H), 0.78 (s, 3H), 0.64 (s, 3H); MS(+FAB): 716 (M+H, 100).

Preparation of compounds 303 and 304: A solution of compound 302 in chloroform (50 ml) was cooled to 0° C. and treated with trifluoroacetic acid (40 ml) under nitrogen. After stirring for fifty minutes at room temperature, the reaction mixture was concentrated, dissolved in chloroform, and evaporated again (three times). The resulting solid was dissolved in methanol, treated with isopropylamine, and preadsorbed onto silica gel. Flash chromatography (4 cm, gradient elution with 2:8:30 to 2:8:15 isopropylamine:methanol:dichloromethane) provided the faster eluting material 304 (3α: amino isomer) in an impure state, followed by compound 303 (3β-amino isomer) as a solid (340 mg, 40% yield). $^1$H NMIR (200 MHz, CDCl$_3$) δ: 2.8–2.6 (m, 8H), 2.47 (br m, 3α-H), 2.0–0.9 (m, 37H), 0.9–0.8 (m, 9H), 0.78 (s, 3H), 0.64 (s, 3H).

The HCl salt of compound 303 was prepared by dissolving the free base in chloroform, treating with 1N HCl in ether (10 ml), and evaporating in vacuo. The solid was recrystallized from methanol in ether (15 ml final volume), and the filtered solid was concentrated overnight under high vacuum to yield compound 303-3HCl as a beige solid (261 mg, 26% yield). $^1$H NMR (200 MHz, CD$_3$OD) δ: 3.3–3.0 (m, 9H), 2.2–1.0 (m, 37H), 1.0–0.9 (m, 12H), 0.71 (s, 3H); MS(+FAB): 516.5 (M+H, 100); Anal. calcd. for C$_{34}$H$_{65}$N$_3$-3HCl-H$_2$O: C=63.48, H=10.97, N=6.53; Found: C=63.72, H=10.71, N=6.25.

Crude compound 304 was again purified by flash chromatography (2 cm, 1:4:20 isopropylamine:methanol:chloroform) to yield the free base (44 mg, 5% yield) ($^1$H NMR (200 MHz, CD$_3$OD) δ: 3.40 (m, 3β-H), 3.3–2.9 (m, 8H), 2.2–1.0 (m, 37H), 1.0–0.8 (m, 12H), 0.70 (s, 3H)), which was dissolved in methanol:dichloromethane (2 ml), treated with 1N HCl in ether (3 ml), concentrated in vacuo, and recrystallized from methanol in ether (1 ml final volume) to produce a gelantinous substance. After cooling in an ice bath, the solid was filtered, washed with ether, and concentrated under high vacuum to deliver compound 304-3HCl (18 mg, 2% yield). $^1$H NMR (200 MHz, CD$_3$OD) δ: 3.45 (m, 3β-H), 3.3–3.0 (m, 8H), 2.3–1.0 (m, 37H), 1.0–0.9 (m, 12H), 0.70 (s, 3H); MS(+FAB): 516.6 (M+H, 100).

Example B

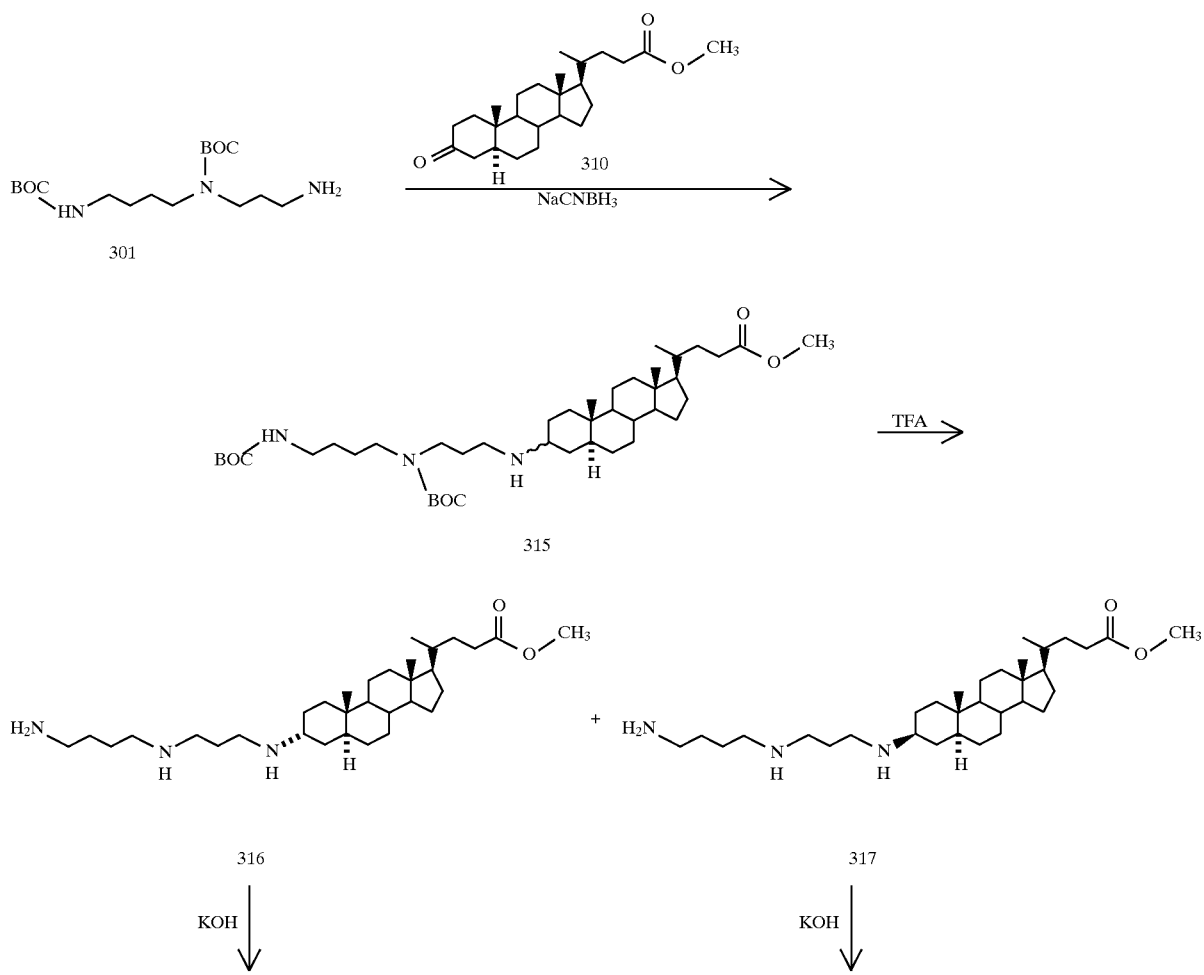

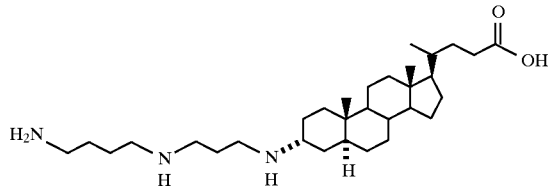

318

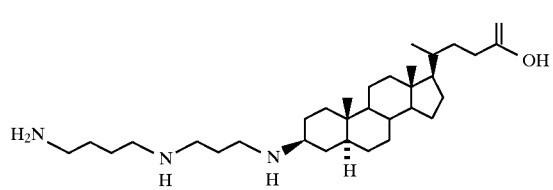

319

Preparation of compound 315: To a solution of 5α-cholanic acid-3-one methyl ester 310 (719 mg, 1.85 mmol, available from Steraloids Inc., of New Hampshire) in anhydrous tetrahydrofuran (10 ml) was added 3Å sieves (4 g), a solution of triamine 301 (650 mg, 1.88 mmol) in dry methanol (25 ml), and sodium cyanoborohydride (600 mg, 9.55 mmol). After stirring for eighteen hours at room temperature, the reaction mixture was filtered through Celite® (SiO$_2$ available from Aldrich) and washed with methanol (20 ml), dichloromethane (20 ml), 10% sodium hydroxide (15 ml), and brine (25 ml). The layers were separated, and the aqueous layer was extracted with more dichloromethane (3×10 ml), and the combined organic layers were washed with brine, dried (Na$_2$SO$_4$), and evaporated. The crude material was purified by flash chromatography (2 cm, gradient elution with 2–4% 2N methanolic ammonia (Aldrich) in dichloromethane), producing compound 315 (1.09 g, 82% yield) as a mixture of C-3 isomers. $^1$H NMR (200 MHz, CDCl$_3$) δ: 4.57 (br s, NH), 3.65 (s, 3H), 3.4–3.0 (m, 6H), 2.8–2.5 (m, 3H), 2.4–1.0 (m, 34H), 1.45 (s, 9H), 1.44 (s, 9H), 0.91 (d, J=6 Hz, 3H), 0.78 (s, 3H), 0.64 (s, 3H) MS(+FAB): 719 (M+H, 100).

Preparation of compounds 316 and 317: A solution of compound 315 (910 mg, 1.27 mmol) in chloroform (39 ml) was treated with trifluoroacetic acid (33 ml) at 0° C. After one hour at room temperature, the reaction mixture was evaporated, dissolved in chloroform, and evaporated again (three times). The crude material was dissolved in methanol, treated with isopropylamine, and preadsorbed onto silica gel. Flash chromatography (2 cm, gradient elution with 1:4:15 to 1:4:6 isopropylamine:methanol:chloroform) yielded the 3α-amino isomer 316 as a crude product and the 3β-amino isomer 317 as a pure product (319 mg, 48% yield). $^1$H NMR (200 MHz, CDCl$_3$) δ: 3.66 (s, 5H), 2.8–2.6 (m, 8H), 2.47 (br m, 3α-H), 2.4–1.0 (m, 34H), 0.90 (d, J=6 Hz, 3H), 0.78 (s, 3H), 0.64 (s, 3H); MS(+FAB): 518 (M+H, 100).

Preparation of compound 318: Crude compound 316, obtained as described above, was dissolved in methanol (20 ml) and treated with 0.5N potassium hydroxide solution (15 ml) in methanol and water (5 ml). After refluxing for thirty minutes and leaving at room temperature overnight, the reaction mixture was purified in the manner described below for the isolation of compound 319, producing the 3α-amino isomer 318 (50 mg, 8% yield, two steps). $^1$H NMR (200 MHz, CD$_3$OD) δ: 3.13 (m, 3β-H), 3.0–2.6 (m, 8H), 2.3–1.0 (m, 34H), 0.96 (d, J=6 Hz, 3H), 0.84 (s, 3H), 0.70 (s, 3H); IR (KBr, cm$^{-1}$): 2930, 2850, 1560, 1444, 1396, 1120, 752; MS(+FAB): 504 (M+H, 100).

Preparation of compound 319: A solution of compound 317 (240 mg, 0.46 mmol) in methanol (15 ml) was treated with 0.5N potassium hydroxide in methanol (10 ml) and water (3.3 ml) under nitrogen at reflux for 3.5 hours. After cooling to room temperature, the reaction mixture was acidified with 1N HCl to a pH of 4–5, extracted with chloroform (3×20 ml), and dried over MgSO$_4$. The solvent was evaporated, and the product was purified by flash chromatography (1 cm diameter, elution with 1:3:10 ammonium hydroxide:methanol:chloroform), producing the 3β-amino isomer 319 as a beige solid (130 mg, 56% yield). $^1$H NMR (200 MHz, CD$_3$OD) δ: 2.9–2.6 (m, 9H), 2.2–1.0 (m, 34H), 0.95 (d, J=6 Hz, 3H), 0.84 (s, 3H), 0.70 (s, 3H); IR (KBr, cm$^{-1}$): 3268, 2928, 2850, 1560, 1444, 1396, 1118, 750; MS(+FAB): 504 (M+H, 100).

Example C

Preparation of compound 353 and compound 354:

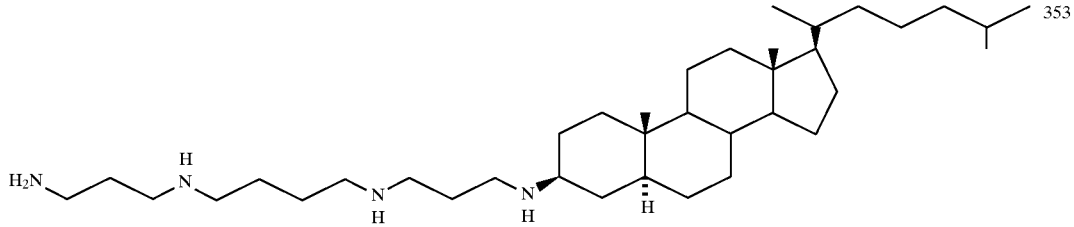

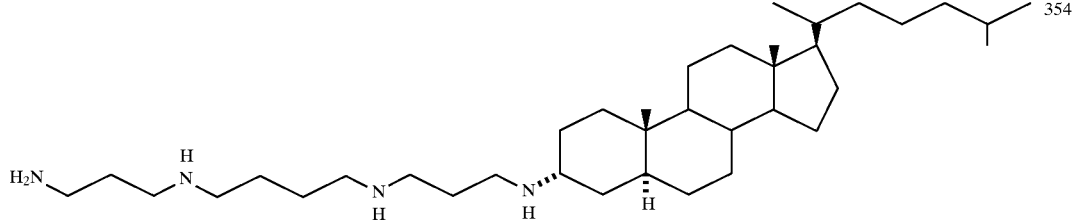

The above compounds were prepared by reductive coupling of 5α-cholestan-3-one 300 (from Steraloids Inc.) to spermine (4 equivalents) with sodium cyanoborohydride in a manner analogous to the preparation of compound 303. Purification was achieved on silica gel (gradient elution with 9:3:1 to 3:3:1 chloroform:methanol:isopropylamine). Compound 353 (more polar) and compound 354 (less polar) were converted to their hydrochloride salts in the same manner as for compound 303. α-Amino compound 354: $^1$H NMR (200 MHz, CD$_3$OD) δ: 3.47 (m, 1H), 3.3–2.9 (m, 12H), 2.3–1.0 (m, 39H), 1.0–0.8 (m, 12H), 0.70 (s, 3H); IR (KBr, cm$^{-1}$): 3396, 2934, 1594, 1457, 1383; MS(+FAB): 573.6 (M+1), Anal. calcd. for C$_{37}$H$_{72}$N$_4$·4HCl·H$_2$O: C=60.31, H=10.67, N=7.60; Found: C=60.01, H=10.83, N=7.67. β-Amino compound 353: $^1$H NMR (200 MHz, CD$_3$OD) δ: 3.3–3.0 (m, 13H), 2.2–1.0 (m, 39H), 1.0–0.8 (m, 12H), 0.70 (s, 3H); IR (KBr, cm$^{-1}$): 2945, 1596, 1466, 1383; MS exact mass (+FAB) calcd.: 573.5835; Found: 573.5801; Anal. calcd. for C$_{37}$H$_{72}$N$_4$·4HCl·H$_2$O: C=58.87, H=10.68, N=7.42; Found: C=58.49, H=10.94, N=7.94.

Compound 353 is a simple adduct of spermine and cholestanol, representing a very inexpensive compound. It can be synthesized like compound 354 in the following straightforward manner:

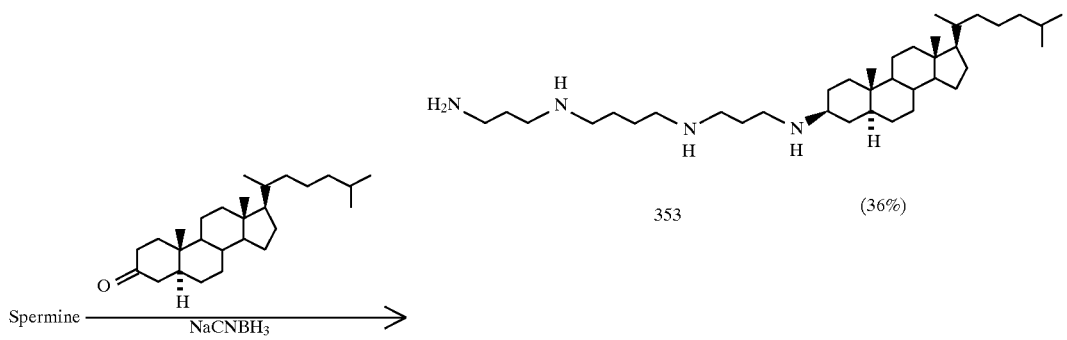

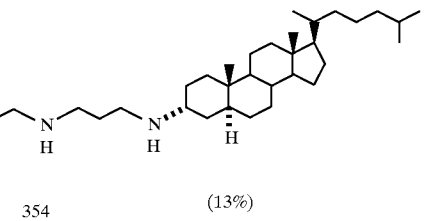

Example D

Preparation of compound 458 and compound 459:

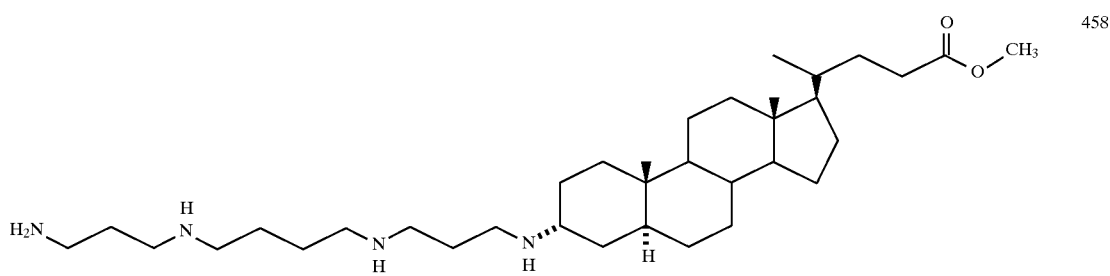

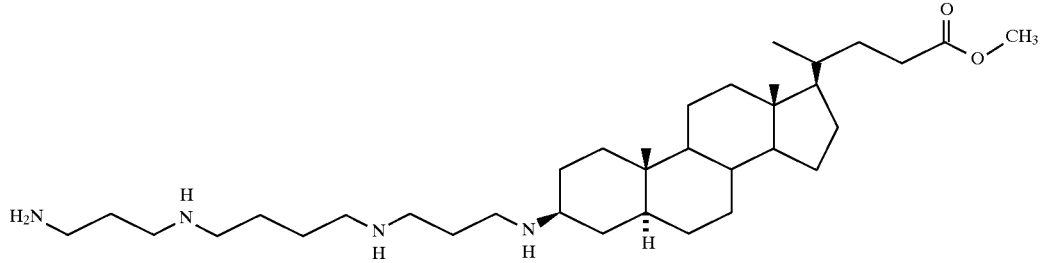

459

The above compounds were prepared from methyl 3-oxo-5α-cholanoate 310 (from Steraloids) and spermine (1.35 equivalents, available from Aldrich) as in the synthesis of compound 353. Purification on silica gel (gradient elution with 6:3:1 to 3:5:2 chloroform:methanol:isopropylamine) produced the less polar α-amino compound 458 and the more polar β-amino compound 459. These compounds were converted to their hydrochloride salts as done for compound 303. Compound 458: $^1$H NMR. (400 MHz, CD$_3$OD) δ: 3.64 (s, 3H), 3.45 (m, 1H), 3.25–3.05 (m, 12H), 2.4–1.0 (m, 36H), 0.93 (d, J=6 Hz, 3H), 0.87 (s, 3H), 0.70 (s, 3H); IR (KBr, cm$^{-1}$): 2943, 1741, 1458, 1169; MS(+FAB): 575.6 (M+1); Anal. calcd. for C$_{35}$H$_{66}$N$_4$O$_2$·4HCl·1.2H$_2$O: C=56.63, H=9.83, N=7.55; Found: C=56.58, H=9.46, N=7.29. Compound 459: $^1$H NMR (400 MHz, CD$_3$OD) δ: 3.63 (s, 3H), 3.2–3.0 (m, 13H), 2.4–1.0 (m, 36H), 0.92 (d, J=6 Hz, 3H), 0.86 (s, 3H), 0.69 (s, 3H); IR (KBr, cm$^{-1}$): 2942, 1739, 1595, 1459, 1382, 1170; MS(+FAB): 575.6 (M+1); Anal. calcd. for C$_{35}$H$_{66}$N$_4$O$_2$·4HCl·1.4H$_2$O: C=56.35, H=9.84, N=7.51; Found: C=56.35, H=9.26, N=7.67.

Example E

Preparation of compounds 380, 381, 382, and 394:

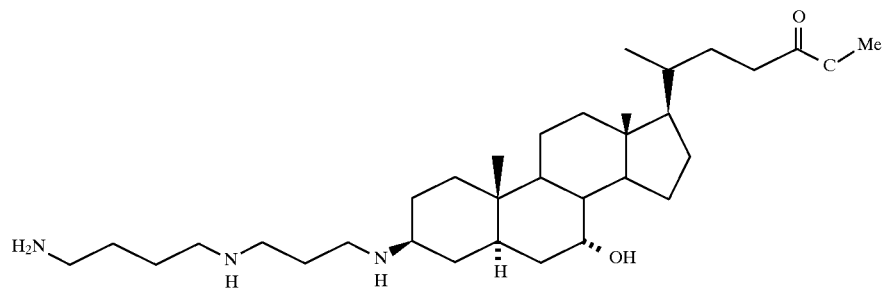

380

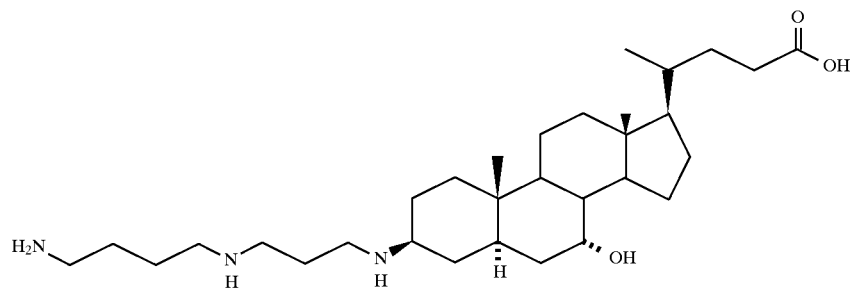

381

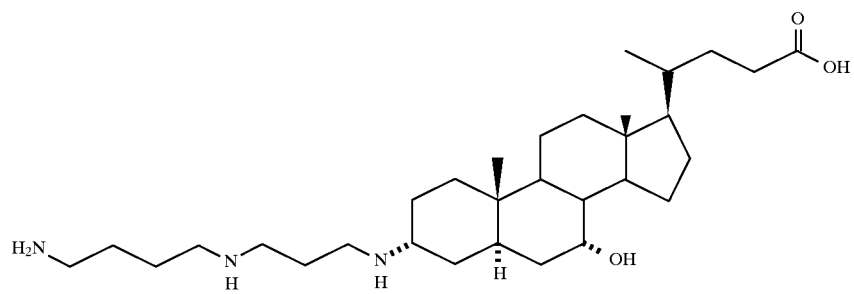

382

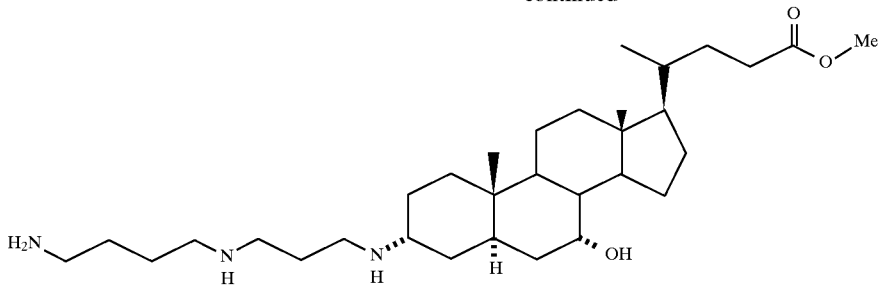

The steroid methyl 7α-hydroxy-3-oxo-5α-cholanoate was prepared according to the method of Iida et al., *Chem. Pharm. Bull.* 41(4), 1993, 763–765, which article is entirely incorporated herein by reference. This steroid was coupled to the polyamine compound 301 with sodium cyanoborohydride, the BOC groups (t-butyloxycarbonyl groups) were removed with trifluoroacetic acid to yield the usters 380 and 394. Hydrolysis of the esters was performed as in the preparation of compound 319 except that lithium hydroxide was used as the base, yielding compounds 381 and 382. Purification was achieved on silica gel (15:4:1 to 10:4:1 chloroform:methanol:isopropylamine). Compounds 381 and 382 were treated with 2M ammonia in methanol and evaporated (3×20 ml) to drive off isopropylamine. The hydrochloride salt was prepared as for compound 303.

Compound 380, $C_{32}H_{59}N_3O_3$: $^1H$ NMR (200 MHz, CDCl$_3$) δ: 3.83 (br s, 1H), 3.66 (s, 3H), 2.8–2.4 (m, 9H), 2.3–1.0 (m, 32H), 0.92 (d, J=6 Hz, 3H), 0.78 (s, 3H), 0.65 (s, 3H); IR (KBr, cm$^{-1}$): 3278, 2928, 1736, 1447, 1163; MS(+FAB): 534 (M+1).

Compound 381, $C_{31}H_{57}N_3O_3$-1.7 H$_2$O: $^1H$ NMR (200 MHz, CD$_3$OD) δ: 3.80 (br s, 1H) 3.0–2.5 (m, 9H), 2.2–1.1 (m, 32H), 0.94 (d, J=6 Hz, 3H), 0.84 (s, 3H), 0.69 (s, 3H); IR (KBr, cm$^{-1}$): 3380, 2929, 1560, 1395; MS(+FAB) calcd.: 520.4478 (M+1); Found: 520.4506; Anal. calcd.: C=67.64, H=11.06, N=7.63; Found: C=67.64, H=10.24, N=7.83.

Compound 382, $C_{31}H_{57}N_3O_3$-2H$_2$O: $^1H$ NMR (200 MHz, CD$_3$OD) δ: 3.80 (br s, 1H), 3.15 (br s, 1H), 3.1–2.6 (m, 8H), 2.2–1.1 (m, 32H), 0.96 (d, J=6 Hz, 3H), 0.85 (s, 3H), 0.69 (s, 3H); IR (KBr, cm$^{-1}$): 3416, 2930, 1560, 1395; MS(+FAB) calcd.: 520.4478 (M+1); Found: 520.4489; Anal. calcd: C=66.99, H=11.06, N=7.56; Found: C=66.93, H=10.16, N=7.28.

Compound 394, $C_{32}H_{59}N_3O_3$-3HCl-0.5H$_2$O: $^1H$ NMR (200MHz, CD$_3$OD) δ: 3.83 (br s, 1H), 3.64 (s, 3H), 3.48 (br s, 1H), 3.3–2.9 (m, 8H), 2.4–1.1 (m, 32 H), 0.94 (d, J=6 Hz, 3H), 0.87 (s, 3H), 0.70 (s, 3H); MS(+FAB): 535 (M+1); Anal. calcd.: C=58.93, H=9.74, N=6.44; Found: C=58.71, H=10.13, N=6.39.

Example F

Preparation of compounds 395, 396, and 397:

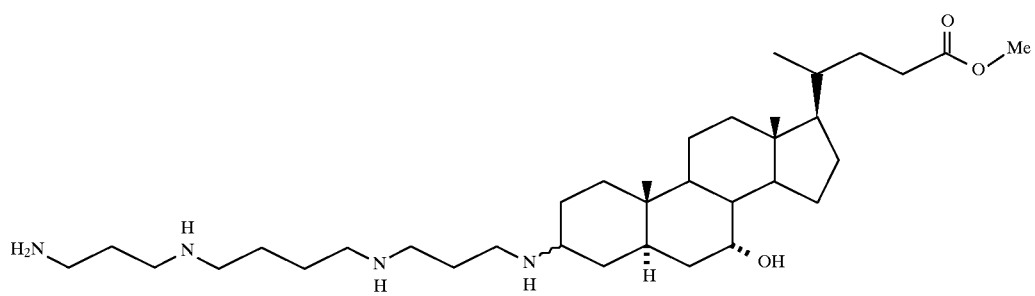

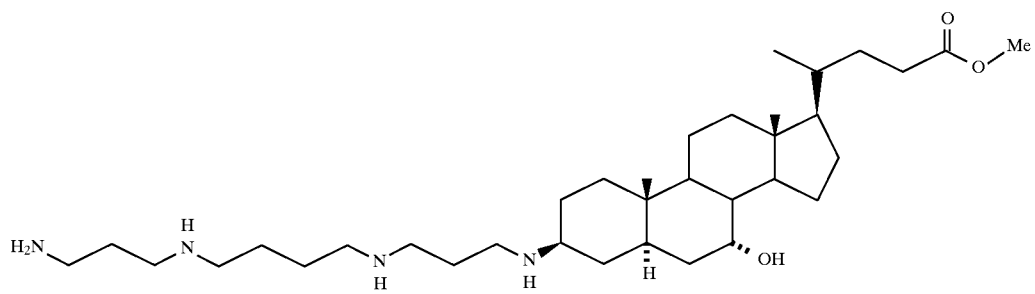

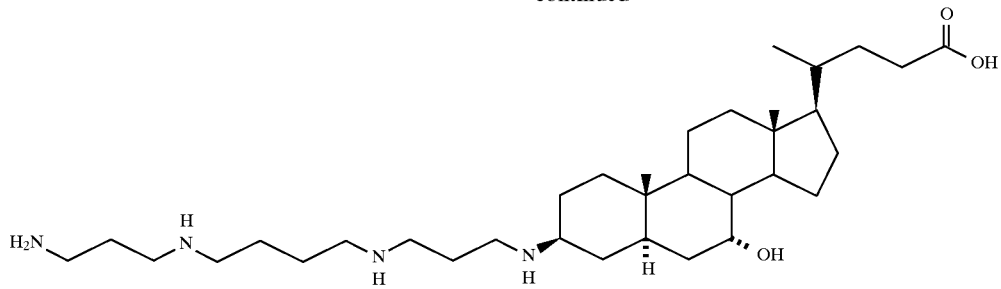

Methyl 7α-hydroxy-3-oxo-5α-cholanoate, which is described in the preparation of compound 380 above, was coupled to spermine (2 equivalents, from Aldrich) with sodium cyanoborohydride, and the ester was hydrolyzed as in the preparation of compound 319, except that lithium hydroxide was used as the base. Purification of compounds 395 and 396 was achieved on silica gel (15:5:1 to 5:5:1 chloroform:methanol:isopropylamine). Purification of compound 397 was achieved on silica gel (2:6:1 benzene:methanol:isopropylamine), followed by treatment with 2M ammonia in methanol (3×20 ml) to drive off isopropylamine. The hydrochloride salts of compounds 395 and 396 were prepared in the same manner as for compound 303.

Compound 395, $C_{35}H_{66}N_4O_3 \cdot 4HCl \cdot 2H_2O$: $^1H$ NMR (200 MHz, $CD_3OD$) δ: 3.80 (br s, 1H), 3.64 (s, 3H), 3.3–3.0 (m, 13H), 2.4–1.0 (m, 34H), 0.94 (d, J=6 Hz, 3H), 0.87 (s,3H), 0.70 (s, 3H); Anal. calcd.: C=54.40, H=9.65, N=7.25; Found: C=54.16, H=9.31, N=7.12.

Compound 396, $C_{35}H_{66}N_4O_3 \cdot 4HCl \cdot 0.5H_2O$: MS(+FAB): 592 (M+1); Anal. calcd.: C=56.37, H=9.60, N=7.51; Found: C=56.43, H=9.83, N=7.27.

Compound 397, $C_{34}H_{64}N_4O_3$: $^1H$ NMR (200 MHz, $CD_3OD$) δ: 3.78 (br s, 1H), 2.9–2.5 (m, 13H), 2.2–1.1 (m, 34H), 0.95 (d, J=6 Hz, 3H), 0.87 (s, 3H), 0.70 (s, 3H); MS(+FAB): 577.3 (M+1).

Example G

Preparation of compound 470:

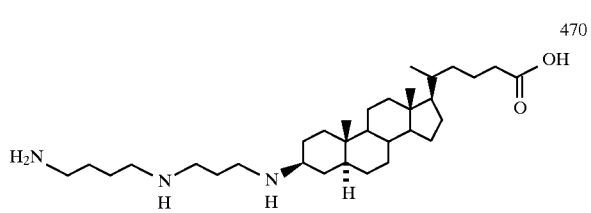

Preparation of precursors:

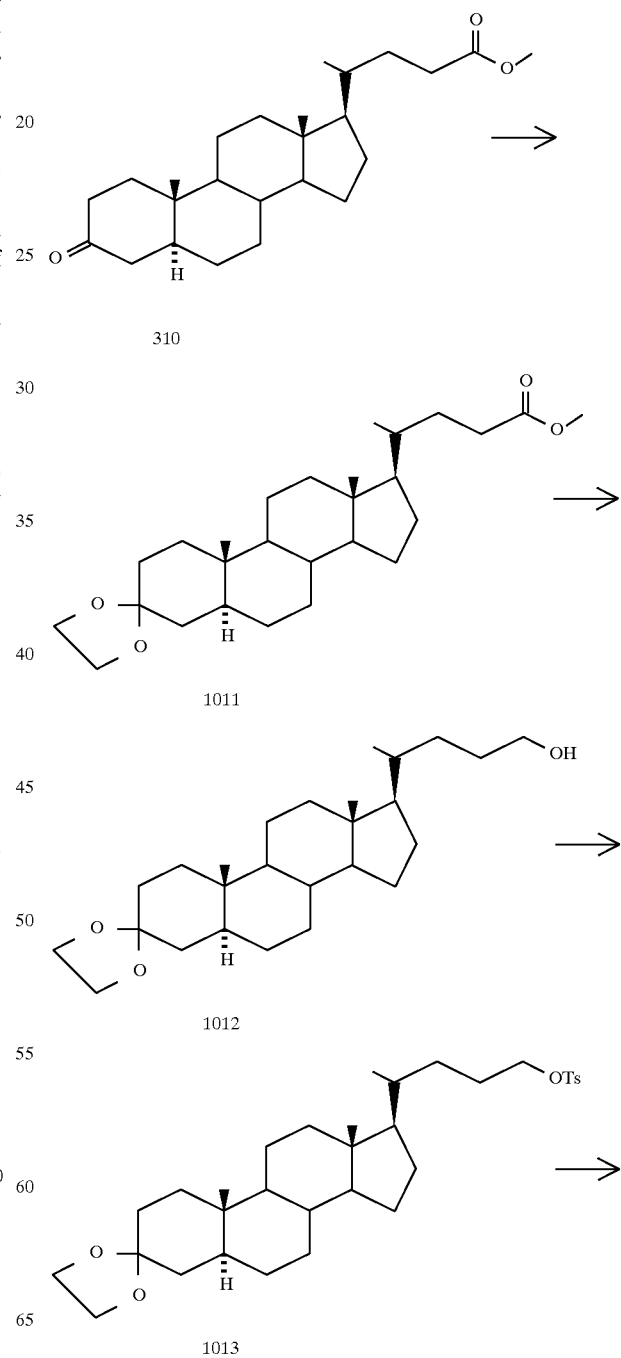

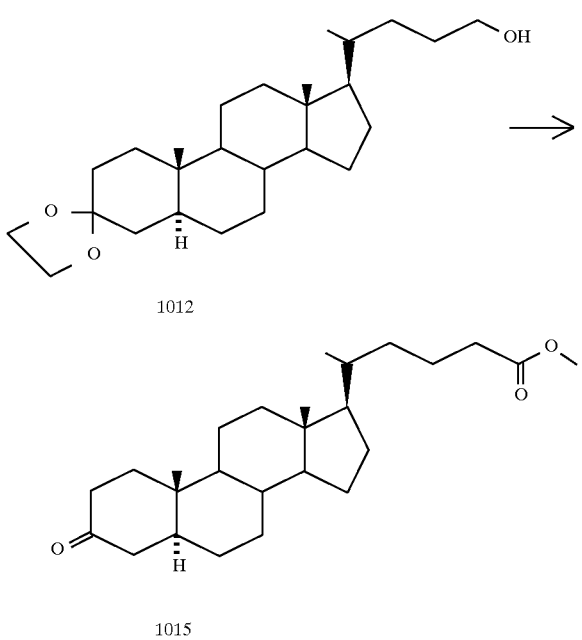

1012

1015

Preparation of compounds 1011 and 1012: A solution of methyl 3-oxo-5α-cholanoate (compound 310 from Steraloid Inc., 2.00 g, 5.15 mmol), p-toluenesulfonic acid (250 mg), and ethylene glycol (25 ml) in benzene (160 ml) was heated to reflux with the removal of water for 6 hours. After cooling to room temperature, saturated sodium bicarbonate (30 ml) was added, and the aqueous phase was extracted with benzene and ethyl acetate. The organic layers were washed with water and brine, dried over sodium sulfate, and evaporated to yield compound 1011, which was used for the next step without purification.

A solution of 1M lithium aluminum hydride (25 ml, 25 mmol) in ether under nitrogen was treated with a solution of compound 1011 in anhydrous ether (80 ml) and heated to reflux for 5 hours. After stirring overnight, the reaction mixture was quenched at 0° C. with water and 2N sodium hydroxide solution. The aqueous layer was extracted with ether, followed by washing with brine, drying over magnesium sulfate, and evaporating to produce compound 1012 (1.80 g, 86% yield). $^1$H NMR (400 MHz, CDCl$_3$) δ: 3.94 (s, 4H), 3.62 (m, 2H), 2.0–1.0 (m, 28H), 0.92 (d, J=6 Hz, 3H), 0.81 (s, 3H), 0.66 (s, 3H).

Preparation of compounds 1013 and 1014: A solution of compound 1012 (3.63 g, 8.97 mmol) in anhydrous pyridine (16 ml) was treated with p-toluenesulfonyl chloride (2.3 g, 12.1 mmol) at room temperature, and left overnight. Ice water was added, and the reaction mixture was left for 30 minutes with stirring. Then 6N hydrochloric acid was added (70 ml), and the aqueous layer was extracted with dichloromethane and ether. The organic layers were washed with 2N hydrogen chloride, saturated sodium bicarbonate and brine, dried, and evacuated to yield crude compound 1013. Compound 1013 was dissolved in dimethylsulfoxide (40 ml) and treated with sodium cyanide (1.4 g, 28 mmol) at 90° C. for 2.5 hours under nitrogen. After cooling, the reaction mixture was treated with ice water and extracted into ether and dichloromethane. The organic layers were washed with brine, dried over sodium sulfate, and purified by chromatography (4-cm diameter, gradient elution with 0–25% ethyl acetate in hexane) to yield pure compound 1014. $^1$H NMR (400 MHz, CDCl$_3$) δ: 3.94 (s, 4H), 2.32 (m, 2H), 2.0–1.0 (m, 28H), 0.93 (d, J=6 Hz, 3H), 0.81 (s, 3H), 0.66 (s, 3H); IR (KBr, cm$^{-1}$): 2930, 2247, 1445, 1381, 1357, 1133, 1091, 928, 899; MS(+FAB): 414.4 (M+1).

Preparation of compound 1015: A solution of compound 1014 (480 mg, 1.16 mmol) in acetic acid (35 ml) and concentrated hydrochloric acid (25 ml) was refluxed for 25 hours. After evaporating the solvent, the residue was partitioned between water and ethyl acetate. After drying and evaporating, the crude carboxylic acid was dissolved in methanol (25 ml), treated with concentrated hydrochloric acid (1 ml), and brought to reflux for 20 minutes. After evaporation of solvent, the product was dissolved in ethyl acetate and water and extracted again with ethyl acetate. The organic layers were washed with brine, dried over sodium sulfate, and purified by flash chromatography (2-cm diameter, gradient elution with 0–25% ethyl acetate in hexane) to produce pure compound 1015 (298 mg, 64% yield), m.p. 147°–148° C. $^1$H NMR (400 MHz, CDCl$_3$) δ: 3.67 (s, 3H), 2.4–1.0 (m, 30H), 1.01 (s, 3H), 0.93 (d, J=6 Hz, 3H), 0.68 (s, 3H); $^{13}$C NMR (400 MHz, CDCl$_3$) δ: 212.3, 174.5, 56.5, 56.1, 54.0, 51.6, 46.9, 44.9, 42.8, 40.1, 38.8, 38.4, 35.8, 35.7, 35.6, 34.7, 31.9, 29.2, 28.4, 24.4, 21.7, 21.6, 18.8, 12.2, 11.7; MS(+FAB): 403.3 (M+1); Anal. calcd. for $C_{26}H_{42}O_3$: C=77.56, H=10.51; Found: C=77.49, H=10.52.

Preparation of compound 470: Steroid 1015 was coupled to polyamine 301 with sodium cyanoborohydride, the BOC groups were removed with trifluoroacetic acid, and the ester was hydrolyzed as in the preparation of compound 319, except that lithium hydroxide was used as the base. Purification was achieved on silica gel (gradient elution with 14:4:1 to 4:4:1 chloroform:methanol:isopropylamine). After evaporation from methanol:chloroform (3×), the compound was treated with 2M ammonia in methanol and evaporated (3×20 ml) to drive off isopropylamine. $^1$H NMR (400 MHz, CD$_3$OD) δ: 2.8–2.6 (m, 9H), 2.2–1.0 (m, 36H), 0.92 (d, J=6 Hz, 3H), 0.80 (s, 3H), 0.66 (s, 3H); MS(+FAB): 518.4 (M+1); Anal. calcd.: C=71.73, H=11.47, N=7.84; Found: C=72.03, H=11.06, N=7.53.

Example H

Preparation of compounds 431, 432, 433, 465, 466, 467, and 469.

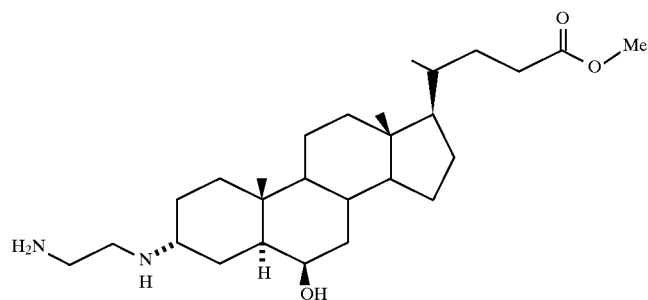
431
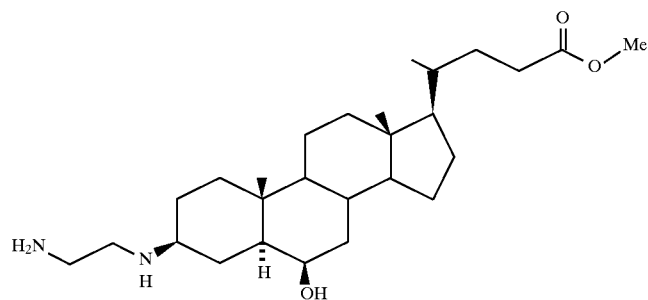
432
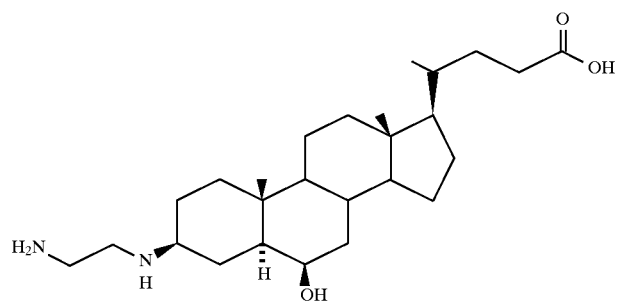
433
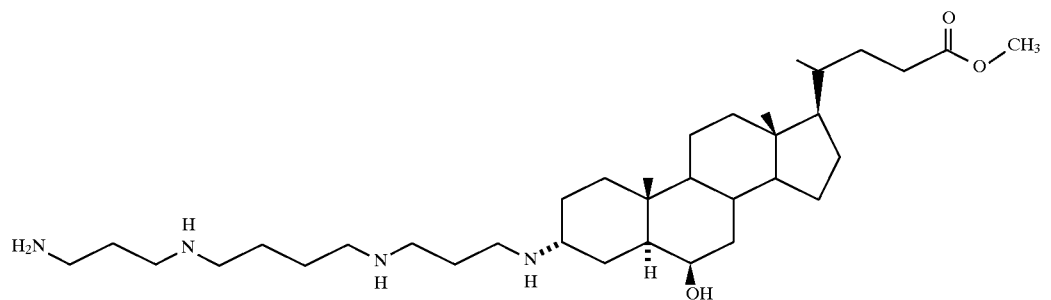
465
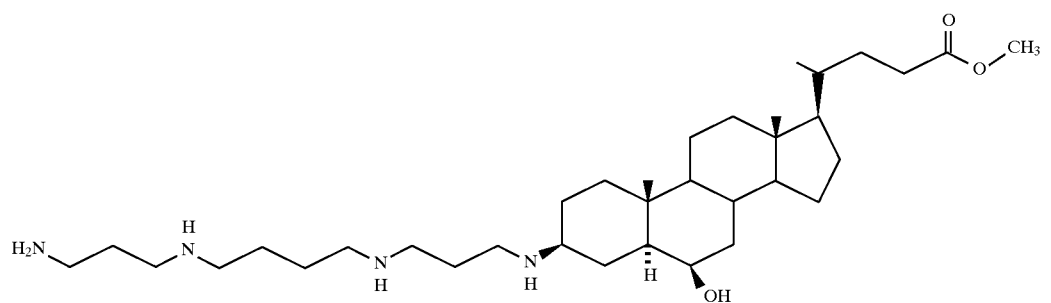
466

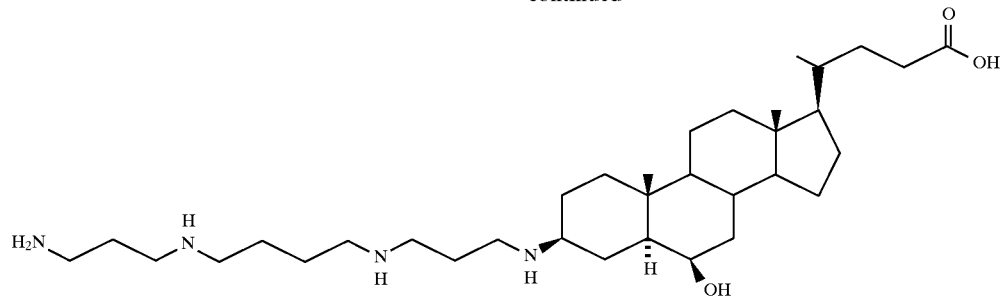
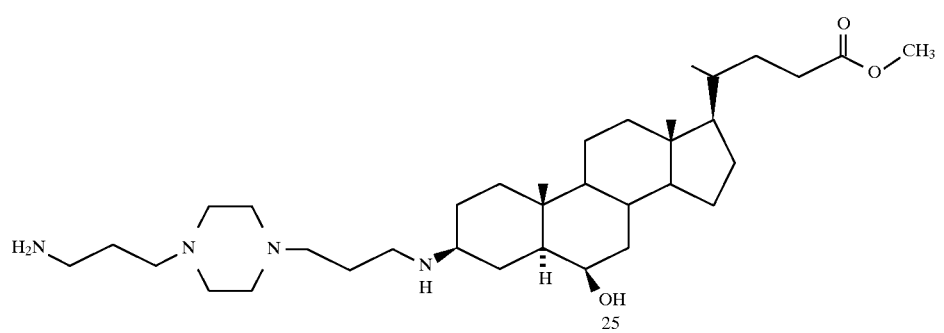
Preparation of precursors:
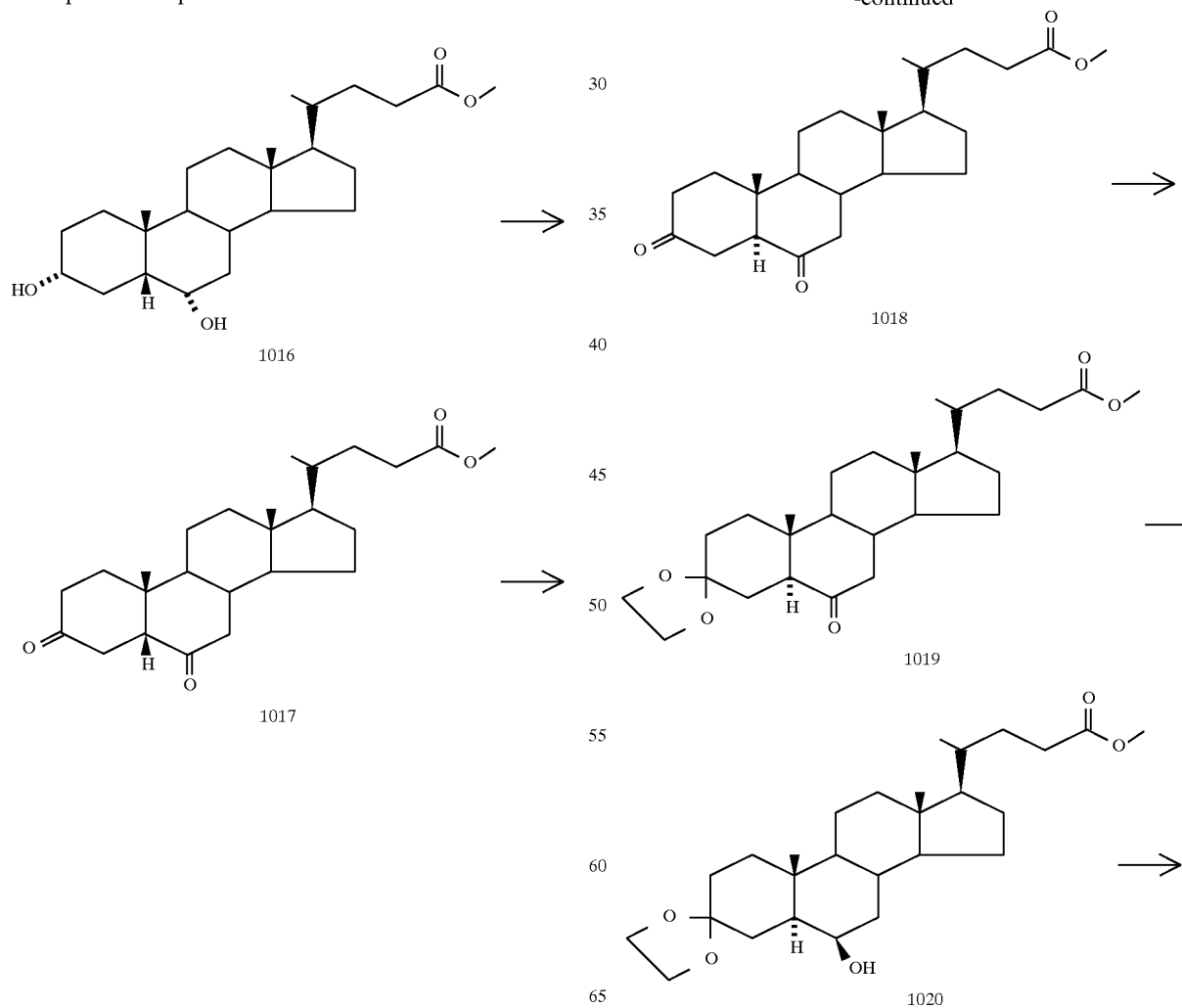

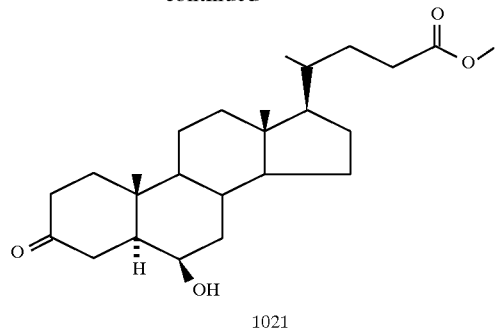

1021

Preparation of compound 1016: The methyl ester of hyodeoxycholic acid was prepared by acid-catalyzed esterification of hyodeoxycholic acid in methanol. To a magnetically stirred 500-ml round-bottom flask containing absolute methanol (200 ml) was added hyodeoxycholic acid (10 g, 25.5 mmol, from Aldrich) and concentrated sulfuric acid (5 ml) dropwise. The reaction was stirred overnight and then treated with dichloromethane (250 ml), followed by washing with sodium bicarbonate solution (2×100 ml) and brine (100 ml). The organic layer was then dried over anhydrous sodium sulfate, filtered, and dried under vacuum to yield compound 1016 (10.1 g, 97% yield) (see *Organic Preparations and Procedures Int.* 19(2–3), 1987, 197–208, which excerpt is entirely incorporated herein by reference).

Preparation of compound 1017: The 3,6-dioxo sterol was prepared by oxidation of methyl hyodeoxycholic acid with pyridinium chlorochromate. Compound 1016 (10.1 g, 25 mmol) was dissolved in dichloromethane (200 ml). To a magnetically stirred flask in an ice water bath was added pyridinium chlorochromate (33 g, 150 mmol, from Aldrich). The reaction was allowed to warm to room temperature and to proceed for 8 hours, until the product was the only visible TLC spot. A major portion of the dichloromethane was removed under vacuum, and ethyl acetate (250 ml) was then added to the flask. The chromium crust in the bottom of the flask was broken up with a spatula, and the contents of the flask were filtered through a Celite® (SiO$_2$ available from Aldrich) column. The elutant from the column was then reduced in volume under vacuum and filtered through a Florisil® column (elution with ethyl acetate). Florisil® is a magnesium silicate material that is available from Aldrich. The elutant was again reduced in volume to approximately 200 ml, and diethyl ether (100 ml) was added, followed by washing with sodium bicarbonate solution (2×250 ml) and then brine (250 ml). The organic layer was dried over anhydrous sodium sulfate, filtered, and dried under vacuum. The total yield of methyl 3,6-dioxo-5β-cholan-24-oate 1017 without recrystallization was 9.6 g (24 mmol, 96%) (see *Organic Preparations and Procedures Int.* 19(2–3), 1987, 197–208). The product can be recrystallized from a number of solvents (absolute methanol, ethyl acetate in hexanes, or diethyl ether in hexanes) if any chromium remains.

Preparation of compound 1018: The 3,6-dioxo-5α sterol was prepared by acid-catalyzed isomerization of the 5β sterol. To methanol (250 ml) was added the 3,6-dioxo-5β sterol 1017 (9.6 g, 24 mmol) and tetrahydrofuran (25 ml) to dissolve the sterol completely. Concentrated hydrochloric acid (12.5 ml) was added, and the reaction was allowed to proceed overnight. The solvent was then removed under vacuum to yield 9.6 g (100% yield) of methyl 3,6-dioxo-5α-cholan-24-oate 1018 (see *Organic Preparations and Procedures Int.* 19(2–3), 1987, 197–208; authors used base-catalyzed isomerization using sodium methoxide rather than HCl).

Preparation of compound 1019: The mono-protection of methyl 3,6-dioxo-5α-cholan-24-oate 1018 may be accomplished using a variety of techniques. One technique involved refluxing compound 1018 (9.6 g, 23.8 mmol) in toluene (250 ml) with ethylene glycol (1.77 g, 28.5 mmol) in the presence of catalytic p-toluenesulfonic acid. A Dean Stark trap was used for removing the toluene/water azeotrope. The reaction was judged to be complete by TLC after approximately 20 minutes. The reaction was worked up by pouring the toluene over sodium bicarbonate solution (500 ml) and ice slurry. The organic layer was washed with additional sodium bicarbonate (200 ml) and brine (200 ml), dried over anhydrous sodium sulfate, filtered, and dried under vacuum. The crude product was chromatographed on silica gel (4 cm×25 cm, elution with 33% ethyl acetate in hexanes). Methyl 3-dioxolane-6-oxo-5α-cholan-24-oate 1019 (8.9 g, 81%) was the second band off the column; the only other product present was the less polar di-dioxolane. Subsequent techniques yielded better results by substituting benzene for toluene and following the reaction by TLC, which apparently allows for greater selectivity. The reaction can be stopped before significant di-protection occurs in the lower boiling solvent. Compound 1019: m.p. 124°–126° C.; $^1$H NMR (200 MHz, CDCl$_3$) δ: 4.04–3.93 (m, 4H), 3.68 (s, 3H), 0.95 (d, J=6 Hz, 3H), 0.78 (s, 3H), 0.69 (s, 3H); IR (KBr, cm$^{-1}$): 2945, 1742, 1709, 1439, 1381, 1313, 1162, 1090; MS(FD): 446(M$^+$), 388.

Preparation of compound 1020: The 6β-hydroxy sterol was prepared in good yield from the mono-protected diketone by reduction with sodium borohydride. The 3-dioxolane-6-oxo sterol 1019 (5 g, 11 mmol) was dissolved in tetrahydrofuran (10 ml) and added to absolute methanol (200 ml) and sodium borohydride (2.5 g, 66 mmol). The sodium borohydride was dissolved and stirred for approximately 20–30 minutes before the addition of the sterol. After stirring overnight, the reaction mixture was treated with chloroform (500 ml), and washed with distilled water (2×200 ml) and then brine (100 ml). The organic layer was then dried over sodium sulfate, filtered, concentrated under vacuum, and purified by flash chromatography on silica gel (4 cm×25 cm, elution with 2:1:1 hexanes:ethyl acetate:methylene chloride) to yield methyl 3-dioxolane-6β-hydroxy-5α-cholan-24-oate 1020 (4.35 g, 87% yield). Alternatively, the crude product can be recrystallized from benzene in hexanes, ethyl acetate in hexanes, or chloroform in hexanes (2×) to yield a product of high purity without need for column chromatography. Compound 1020: m.p. 164° C.; $^1$H NMR (200 MHz, CDCl$_3$) δ: 4.04–3.93 (m, 4H), 3.77 (br s, 1H), 3.66 (s, 3H), 1.03 (s, 3H), 0.92 (d, J=6 Hz, 3H), 0.69 (s, 3H); IR (KBr, cm$^{-1}$): 3533, 2937, 1726, 1438, 1379, 1255, 1191, 1096; X-ray diffraction revealed the expected structure.

Preparation of compound 1021: The 3-dioxolane was deprotected using acidic acetone solution. The 3-dioxolane-6β-hydroxy-sterol 1020 (4.0 g, 8.9 mmol) was dissolved in acetone (200 ml) and treated with concentrated hydrochloric acid solution (10 ml). After approximately 1 hour, the reaction mixture was poured into a sodium bicarbonate solution. The solution was extracted with dichloromethane (3×200 ml), washed with distilled water (100 ml) and then brine (100 ml), dried over anhydrous sodium sulfate, filtered, and evaporated under vacuum to yield methyl 3-oxo-6β-hydroxy-5α-cholan-24-oate 1021 (3.45 g, 100% yield): $^1$H NMR (200 MHz, CDCl$_3$) δ: 3.8 (br m, 1H), 3.69 (s, 3H), 1.24 (s, 3H), 0.95 (d, J=6 Hz, 3H), 0.74 (s, 3H); IR (KBr, cm$^{-1}$): 3447, 2954, 1742, 1707, 1431.

Preparation of compounds 431 and 432: The ethylenediamine compounds were prepared as follows. A magnetically stirred solution of 50:50 methanol:tetrahydrofuran (100 ml) and ethylenediamine (2 ml) was treated with acetic acid to lower the pH to approximately 6. The 3-oxo sterol 1021 (1.5 g, 3.7 mmol) was added, and the mixture was stirred for 15 minutes. Sodium cyanoborohydride (1 g, 16 mmol) was dissolved in 10 ml methanol and added to the reaction vessel, and the pH was again adjusted to 6 by the addition of acetic acid. The reaction was stirred for 1 hour, and the contents of the flask were poured into a pH 10.5 carbonate-buffer ice slurry (250 ml). The solution was extracted with chloroform (5×150 ml). The organic layers were combined, dried over anhydrous sodium sulfate, filtered, dried under vacuum, and purified by flash chromatography on silica gel (4 cm×25 cm, elution with 8:2:1 chloroform:methanol:isopropylamine) to produce the less polar α-isomer 431 (260 mg, 15% yield) and the more polar β-isomer 432 (840 mg, 49% yield). Compound 431: $^1$H NMR (400 MHz, CD$_3$OD) δ: 3.74 (m, 1H), 3.65 (s, 3H), 3.53 (m, 1H), 1.06 (s, 3H), 0.94 (d, J=6 Hz, 3H), 0.74 (s, 3H); IR (KBr, cm$^{-1}$): 3426, 2943, 1740, 1590, 1438, 1379, 1258, 1168, 1027; MS(+FAB): 449.5 (M+1); Anal. calcd. for C$_{27}$H$_{48}$N$_2$O$_3$-2HCl-0.7H$_2$O: C=60.70, H=9.70, N=5.24; Found: C=60.97, H=9.68, N=5.34. Compound 432: $^1$H NMR (400 MHz, CD$_3$OD) δ: 3.75 (m, 1H), 3.64 (s, 3H), 1.02 (s, 3H), 0.94 (d, J=6 Hz, 3H), 0.73 (s, 3H); IR (KBr, cm$^{-1}$): 3560, 3366, 3257, 2936, 1726, 1648, 1605, 1438, 1376, 1166, 1047; MS(+FAB): 449.5 (M+1); Anal. calcd. for C$_{27}$H$_{48}$N$_2$O$_3$-0.4H$_2$O: C=71.13, H=10.79, N=6.14; Found: C=71.15, H=10.71, N=6.28.

Preparation of compounds 465 and 466: To a magnetically stirred flask containing anhydrous methanol (100 ml) was added compound 1021 (1.5 g, 3.7 mmol), spermine (2 g, 9.9 mmol), powdered 3Å sieves (2 g), and acetic acid until the pH was 6. The flask was sealed, the contents stirred overnight, and then sodium cyanoborohydride (1 g, 16 mmol) in methanol (10 ml) was added. The pH was again adjusted with acetic acid, and the reaction mixture was stirred for 8 hours. The workup was similar to the workup for the ethylenediamine compounds 431 and 432 described above. The crude product was purified by flash chromatography (5 cm×25 cm, elution with 4:5:1 chloroform:methanol:isopropylamine), producing the less polar α-amino isomer 465 and the more polar β-amino isomer 466. The total yield of amino sterol was 1.3 g (58% yield). Compound 465: $^1$H NMR (400 MHz, CD$_3$OD) δ: 3.75 (m, 1H), 3.65 (s, 3H), 3.54 (m, 1H), 1.06 (s, 3H), 0.95 (d, J=6 Hz, 3H), 0.74 (s, 3H); IR (KBr, cm$^{-1}$): 3406, 2944, 1740, 1596, 1466, 1168, 1049, 1027; MS(+FAB): 591.4 (M+1); Anal. calcd. for C$_{35}$H$_{66}$N$_4$O$_3$-4HCl-1.2H$_2$O: C=55.43, H=9.62, N=7.39; Found: C=55.70, H=9.15, N=7.12. Compound 466: $^1$H NMR (400 MHz, CD$_3$OD) δ: 3.79 (m, 1H), 3.65 (s, 3H), 1.06 (s, 3H), 0.95 (d, J=6 Hz, 3H), 0.74 (s, 3H); IR (KBr, cm$^{-1}$): 3406, 2944, 1740, 1595, 1459, 1381, 1167, 1051, 1026; MS(+FAB): 591.4 (M+1); Anal. calcd. for C$_{35}$H$_{66}$N$_4$O$_3$-4HCl-1.2H$_2$O: C=55.43, H=9.62, N=7.39; Found: C=55.48, H=9.03, N=7.33.

Preparation of compound 469: This compound was prepared in a manner analogous to that used for compound 466, but using polyamine 1023 produced by the following reaction:

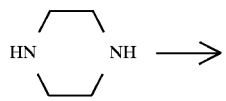

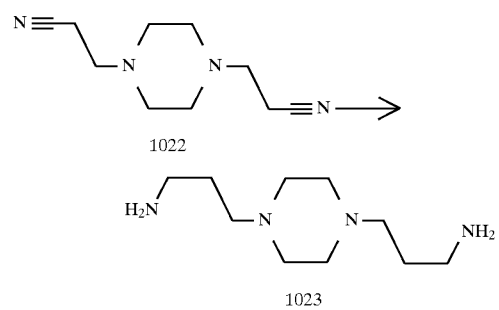

The polyamine 1023 was prepared from piperazine by double addition of acrylonitrile to yield compound 1022, which was reduced by Raney nickel catalyzed hydrogenation. β-amino isomer 469: $^1$H NMR (400 MHz, CD$_3$OD) δ: 3.78 (m, 1H), 3.64 (s, 3H), 3.5–3.3 (m, 8H), 3.2–3.0 (m, 9H), 2.4–1.0 (m, 30H), 1.03 (s, 3H), 0.92 (d, J=6.5 Hz, 3H), 0.71 (s, 3H); IR (KBr, cm$^{-1}$): 3406, 2943, 1736, 1594, 1443, 1165; MS(+FAB): 589.4 (M+1); Anal. calcd. for C$_{35}$H$_{64}$N$_4$O$_3$-4HCl-3H$_2$O: C=53.29, H=9.46, N=7.10; Found: C=53.06, H=8.90, N=8.43.

Preparation of compounds 433 and 467: An amount of aminosterol methyl ester (1 mmol) as the free base (compounds 432 and 466, respectively) was weighed into a 25-ml round-bottom flask. The aminosterol was dissolved in a minimal amount of tetrahydrofuran (2 ml), treated with 1N potassium hydroxide solution (10 ml), and magnetically stirred for 1 hour. The solution was then neutralized with 1N HCl, and the solvent was removed under vacuum. The residue was redissolved in a minimal amount of deionized water and applied to an octadecyl-functionalized silica gel column (Aldrich, 2×10 cm, gradient elution of acetonitrile in 2% trifluoroacetic acid in water). The fractions containing aminosterol were pooled, and the solvent was removed under vacuum. The aminosterol was redissolved in 0.1N HCl, and the solvent was removed under vacuum (2×) to insure the removal of trifluoroacetate. Benzene was added to the resulting hydrochloride salts, followed by evaporation overnight to remove as much water as possible.

Ethylenediamine β-amino isomer 433 was not treated with HCl, but isolated as the trifluoroacetate salt. Compound 433: $^1$H NMR (400 MHz, CD$_3$OD) δ: 3.78 (m, 1H), 1.06 (s, 3H), 0.95 (d, J=6.5 Hz, 3H), 0.74 (s, 3H); IR (KBr, cm$^{-1}$): 3533, 3488, 2941, 1716, 1679, 1615, 1489, 1431, 1191; MS(+FAB): 435.5 (M+1), 531.5 (likely a trace of the trifluoroacetamide); Anal. calcd. for C$_{26}$H$_{46}$N$_2$O$_3$-2TFA-0.7H$_2$O: C=53.36, H=7.37, N=4.15; Found: C=54.36, H=7.45, N=4.40.

Spermine β-amino isomer 467: $^1$H NMR (400 MHz, CD$_3$OD) δ: 3.80 (m, 1H), 1.05 (s, 3H), 0.95 (d, J=6.5 Hz, 3H), 0.73 (s, 3H); IR (KBr, cm$^{-1}$): 3406, 2944, 1718, 1637, 1458; MS(+FAB): 577.4 (M+1); Anal. calcd. for C$_{34}$H$_{64}$N$_4$O$_3$-4HCl-4H$_2$O: C=51.38, H=9.64, N=7.05; Found: C=51.40, H=8.77, N=7.01.

Example I

Preparation of bile acid methyl esters 409, 410, 411, 355, 356, 416, 448, 414, 415, 412, 413, 417, and 449:

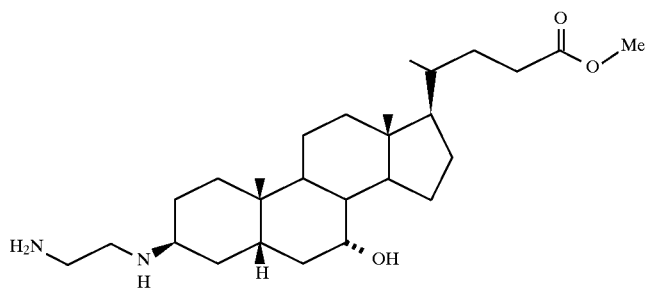
409
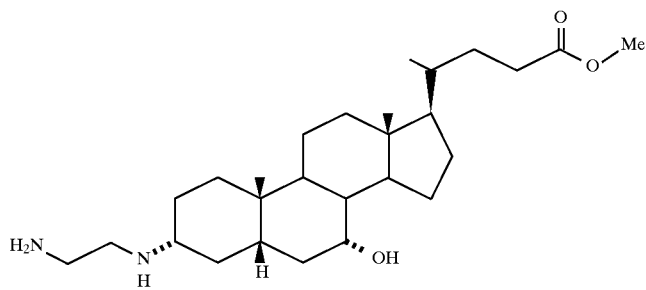
410
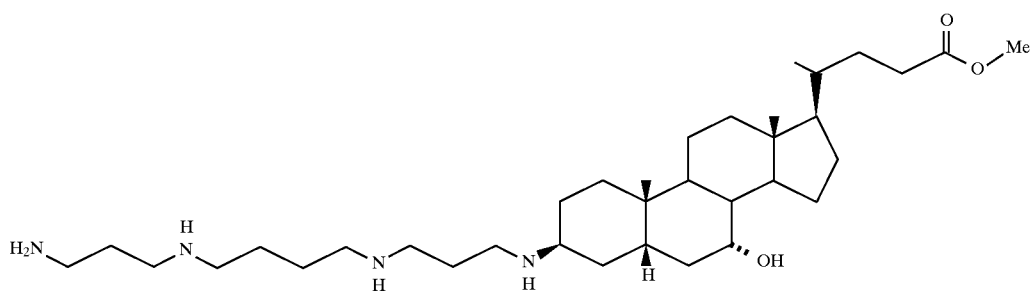
411
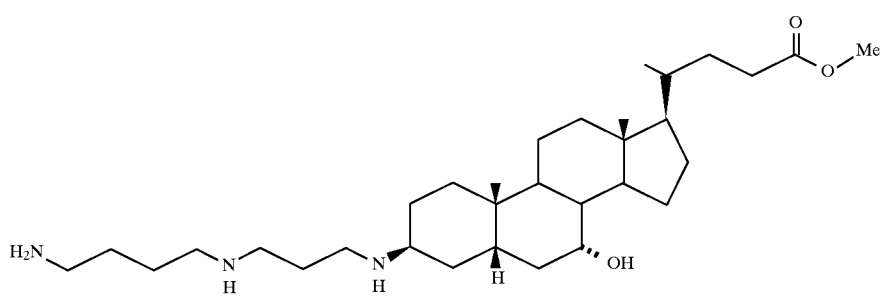
355
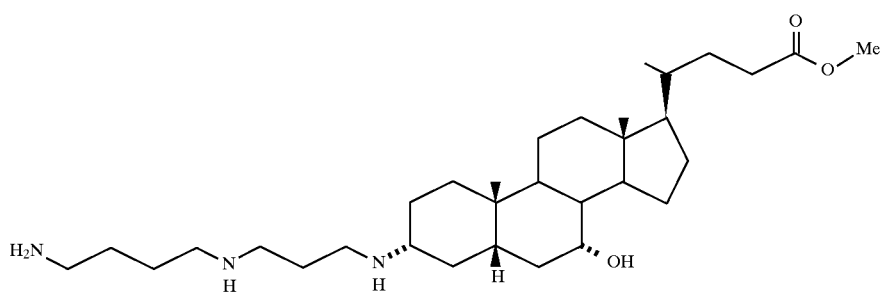
356

-continued
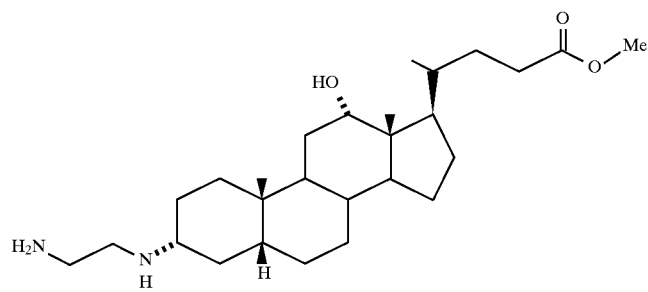
416
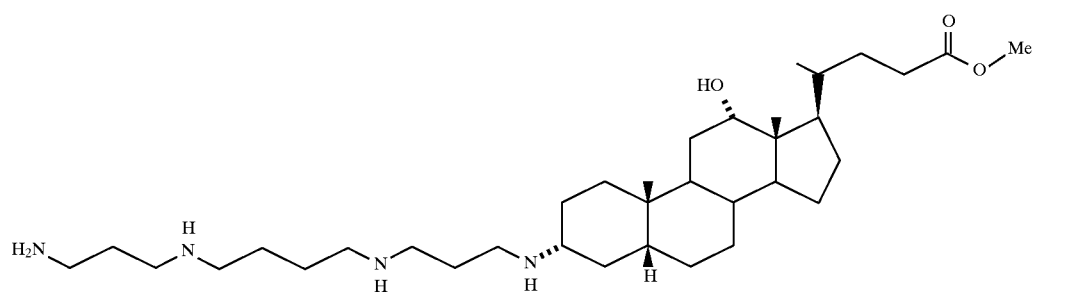
448
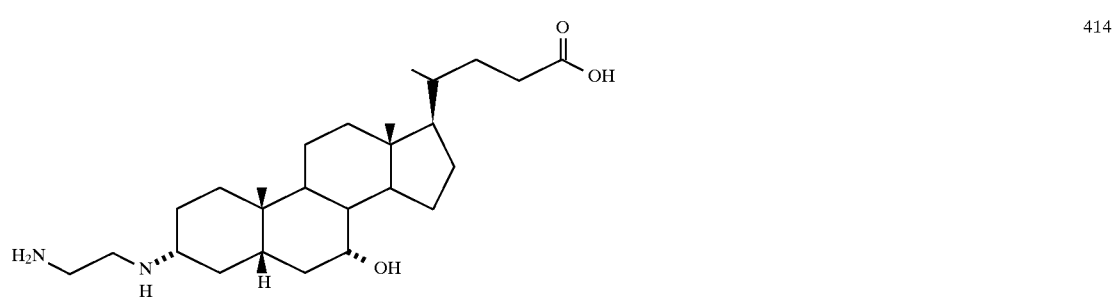
414
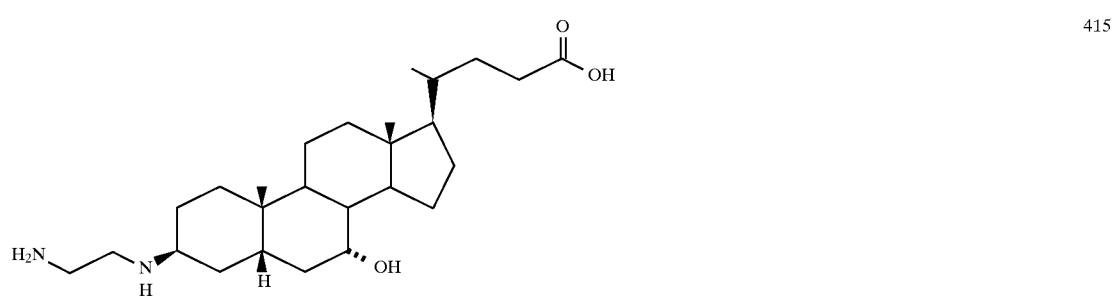
415
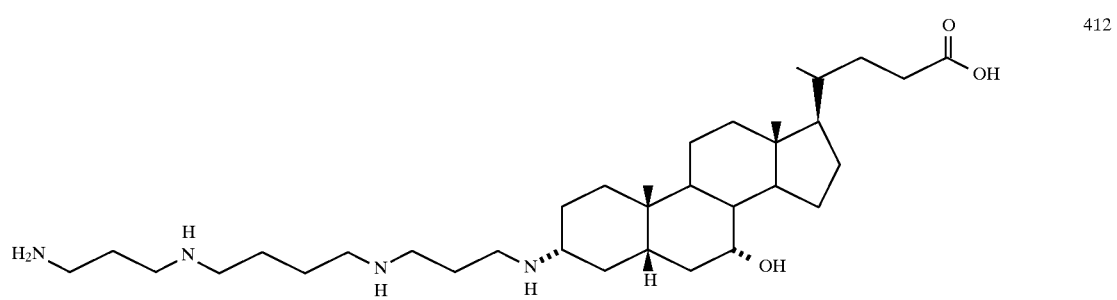
412

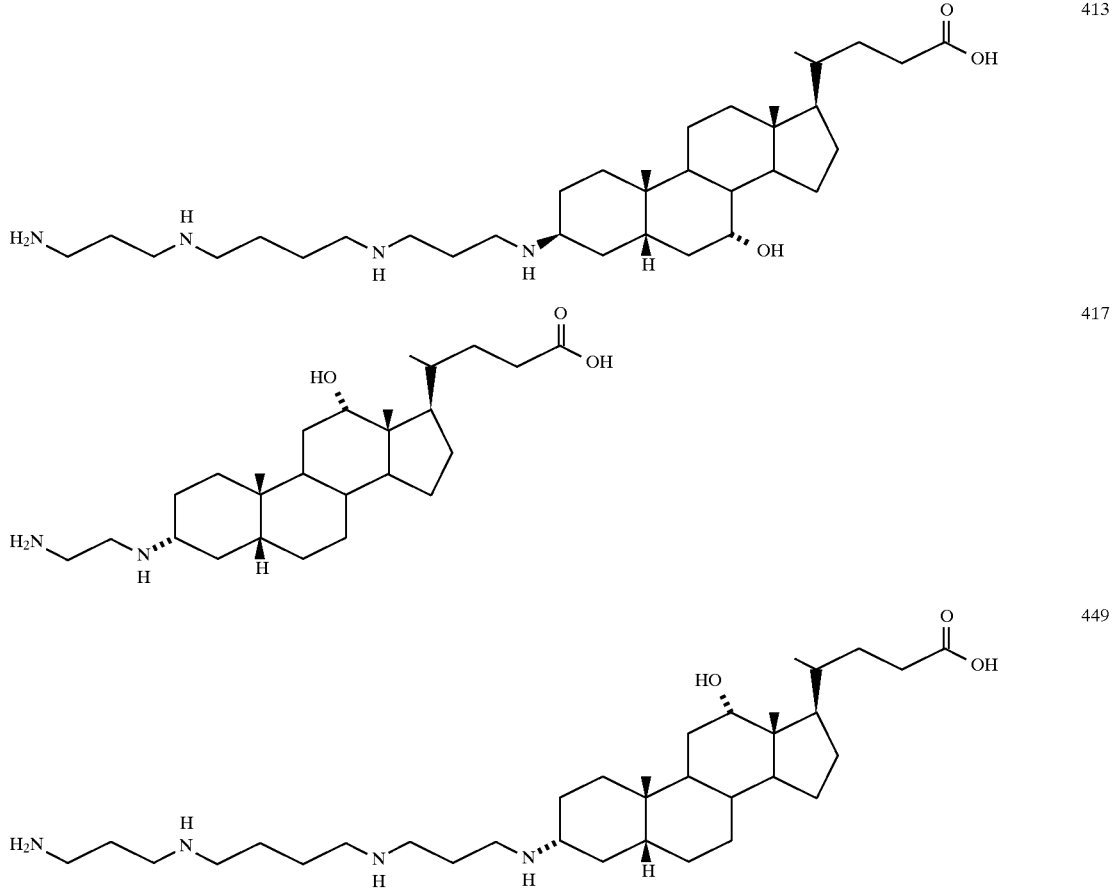

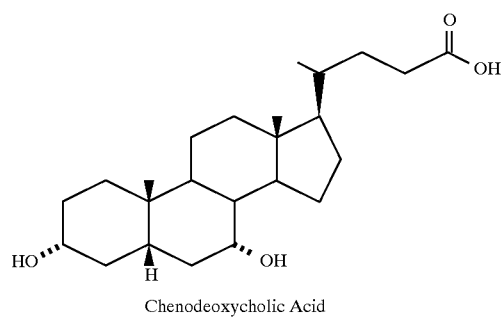

Chenodeoxycholic Acid

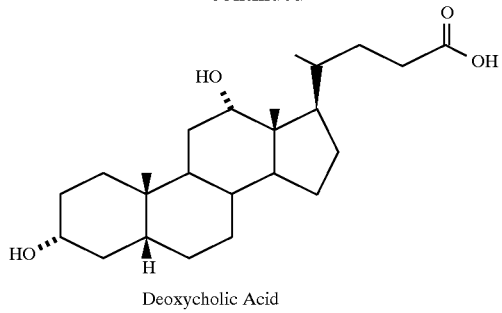

Deoxycholic Acid

Preparation of precursors: The methyl esters of chenodeoxycholic acid and deoxycholic acid (available from Aldrich), which are structurally depicted below, were prepared by the same procedure as used to esterify hyodeoxycholic acid to compound 1016.

Silver carbonate oxidations of bile acid esters to prepare 3-keto steroids: Both chenodeoxycholic and deoxycholic acid derivatives were prepared by reductive aminations of the 3-oxo sterols with the appropriate amines. The 3-oxo sterols were prepared by similar procedures as described below.

Silver carbonate on Celite® (SiO$_2$ available from Aldrich) was prepared by dissolving 4 equivalents of silver nitrate in deionized water and adding sufficient Celite® (SiO$_2$ available from Aldrich) to result in 50% silver carbonate on Celite® (SiO$_2$ available from Aldrich). To the magnetically stirred solution was added 2.2 equivalents of sodium carbonate dissolved in deionized water, with continued vigorous stirring. The resulting silver carbonate precipitated on Celite® (SiO$_2$ available from Aldrich) was filtered through a glass-fritted funnel, washed with tetrahydrofuran, and allowed to dry in a vacuum desiccator. The methyl ester of the bile acid to be oxidized was dissolved in toluene, treated with 2 equivalents of silver carbonate on Celite® (SiO$_2$ available from Aldrich), and heated to reflux using a Dean Stark apparatus for azeotropic removal of water. The oxidation was complete in less than 6 hours for both sterols. The only product in both cases was the desired 3-oxo sterol. The solution was filtered, and the solvent was removed under vacuum. The product in both cases recrystallized readily from ethyl acetate in hexanes to give the 3-oxo sterol in excellent yield (>89% in both cases).

Preparation of compounds 409 and 410: The 3-oxo sterol methyl ester of chenodeoxycholic acid (1.5 g, 3.7 mmol) was dissolved in methanol, to which a ten-fold excess of ethylenediamine (2.5 ml) was added. The pH was lowered with acetic acid to approximately 6, NaBH$_3$CN (1 g, 15.9 mmol) dissolved in methanol was added, and the pH was again adjusted with acetic acid. The solution was stirred for 1 hour, and then worked up and purified in the same manner as compound 431. The total yield of aminosterol was 58%, with an approximate ratio of α-amino isomer to the less polar β-amino isomer of 7:3. β-Amino isomer 409: $^1$H NMR (400 MHz, CD$_3$OD) δ: 3.81 (m, 1H), 3.68 (s, 3H), 3.42 (m, 1H), 1.04 (s, 3H), 0.95 (d, J=6.5 Hz, 3H), 0.72 (s, 3H); IR (KBr, cm$^{-1}$): 3428, 2940, 2055, 1740, 1591, 1440, 1377, 1169, 1077, 984; MS(+FAB): 449.3 (M+1); Anal. calcd. for C$_{27}$H$_{48}$N$_2$O$_3$-2HCl-1.2H$_2$O: C=59.70, H=9.72, N=5.16; Found: C=59.59, H=9.49, N=5.15. α-Amino isomer 410: $^1$H NMR (400 MHz, CD$_3$OD) δ: 3.82 (m, 1H), 3.65 (s, 3H), 3.05 (br m, 1H), 1.00 (s, 3H), 0.94 (d, J=6.5 Hz, 3H) 0.72 (s, 3H); IR (KBr, cm$^{-1}$): 3522, 2944, 2017, 1718, 1619, 1448, 1377, 1314, 1282, 1260, 1163, 1018; MS(+FAB): 449.3 (M+1); Anal. calcd. for C$_{27}$H$_4$N$_2$O$_3$-2HCl-3.7H$_2$O: C=55.13, H=9.84, N=4.76; Found: C=55.03, H=9.32, N=4.78.

Preparation of compound 411: This spermine compound was prepared by the same procedure as the ethylenediamine compounds 409 and 410, except for the following modification. One gram of the 3-oxo sterol methyl ester of chenodeoxycholic acid and 1 g of spermine (approx. 2 equiv.) were used, and the chromatography required a more polar solvent system (5:4:1 CHCl$_3$:methanol:isopropylamine was used). The total yield of aminosterol was 48%. The ratio of α-amino isomer to β-amino isomer 411 was not determined due to incomplete separation. Compound 411: $^1$H NMR (400 MHz, CD$_3$OD) δ: 3.83 (m, 1H), 3.65 (s, 3H), 3.42 (m, 1H), 1.04 (s, 3H), 0.95 (d, J=6.5 Hz, 3H), 0.70 (s, 3H); IR (KBr, cm$^{-1}$): 3404, 2946, 2059 1739, 1595, 1458, 1378, 1168, 1073, 1012, 985, 759; MS(+FAB): 591.4 (M+1); Anal. calcd. for C$_{36}$H$_{66}$N$_4$O$_3$-4HCl-4H$_2$O: C=51.97, H=9.72, N=6.93; Found: C=51.6, H=8.53, N=6.77.

Preparation of compounds 355 and 356: The 3-oxo sterol methyl ester of chenodeoxycholic acid was coupled to polyamine 301 with sodium cyanoborohydride, the BOC groups were removed with trifluoroacetic acid, and the ester was hydrolyzed as in the preparation of compound 319. Purification was achieved on silica gel (15:4:1 to 10:4:1 chloroform:methanol:isopropylamine). Less polar β-amino isomer 355, C$_{32}$H$_{59}$N$_3$O$_3$. $^1$H NMR (400 MHz, CDCl$_3$) δ: 3.87 (m, 1H), 3.68 (s, 3H), 3.15 (m, 1H), 3.0–2.7 (m, 8H), 2.4–1.0 (m, 32H), 0.99 (s, 3H), 0.91 (d, J=6 Hz, 3H), 0.66 (s, 3H); MS(DCI): 534 (M+1). More polar α-amino isomer 356, C$_{32}$H$_{59}$N$_3$O$_3$-3HCl: $^1$NMR (400 MHz, CD$_3$OD) δ: 3.82 (m, 1H), 3.25–2.95 (m, 9H), 2.5–1.0 (m, 32H), 0.97 (s, 3H), 0.94 (d, J=6 Hz, 3H), 0.69 (s, 3H); MS(DCI): 534 (M+1).

Preparation of compound 416: The procedures used for the preparation of deoxycholic acid derivatives were the same as those used in the preparation of the chenodeoxycholic acid derivatives. For the ethylenediamine compound 416, the total yield of aminosterol was 62%, with the ratio of α-amino isomer 416 to β-amino isomer being 4:1. Compound 416: $^1$H NMR (400 MHz, CD$_3$OD) δ: 3.97 (m, 1H), 3.68 (s, 3H), 3.22 (br m, 1H), 1.02 (d, J=6.5 Hz, 3H), 1.01 (s, 3H), 0.73 (s, 3H); IR (KBr, cm$^{-1}$): 3418, 2940, 1739, 1616, 1456, 1379, 1253, 1169, 1036; MS(+FAB): 449.4 (M+1); C$_{27}$H$_{48}$N$_2$O$_3$-2HCl-0.5H$_2$O: C=61.12, H=9.69, N=5.28; Found: C=61.20, H=9.50, N=5.07.

Preparation of compound 448: For the spermine derivatives of deoxycholic acid, the total yield of aminosterol was 46% (difficulty in the workup was likely responsible for the lower yield). The ratio of α-amino isomer 448 to β-amino isomer was not determined due to incomplete separation. Compound 448: $^1$H NMR (400 MHz, CD$_3$OD) δ: 3.98 (m, 1H), 3.67 (s, 3H), 1.01 (d, J=6 Hz, 3H), 1.01 (s, 3H), 0.73 (s, 3H); IR (KBr, cm$^{-1}$): 2944, 1738, 1594, 1451, 1378, 1169, 1038, 758; MS(+FAB): 591.5 (M+1); Anal. calcd. for C$_{35}$H$_{66}$N$_4$O$_3$-4HCl-2.3H$_2$O: C=54.02, H=9.66, N=7.20; Found: C=54.00, H=8.64, N=7.22.

Preparation of compounds 414 and 415: The free acids were prepared from the methyl esters as in the preparation of 6β-hydroxy 433. α-Amino isomer 414: $^1$H NMR (400 MHz, CD$_3$OD) δ: 3.83 (m, 1H), 3.06 (br m, 1H), 1.04 (s, 3H), 0.96 (d, J=6 Hz, 3H), 0.73 (s, 3H); IR (KBr, cm$^{-1}$): 2940, 2053, 1709, 1452, 1378, 1167, 1076, 1007, 975; MS(+FAB): 435.5 (M+1); Anal. calcd. for C$_{26}$H$_{46}$N$_2$O$_3$-2HCl-1.5H$_2$O: C=58.41, H=9.62, N=5.24; Found: C=58.24, H=9.40, N=5.47. β-Amino isomer 415: $^1$NMR (400 MHz, CD$_3$OD) δ: 3.83 (m, 1H), 3.47 (m, 1H), 1.06 (s, 3H), 0.95 (d, J=6 Hz, 3H), 0.73 (s, 3H); IR (KBr, cm$^{-1}$): 3488, 2935, 2054, 1709, 1593, 1499, 1450, 1246, 1168, 1077, 1022, 984; MS(+FAB): 435.5 (M+1); Anal. calcd. for C$_{26}$H$_{46}$N$_2$O$_3$-2HCl-1.5H$_2$O: C=58.41, H=9.62, N=5.24; Found: C=58.59, H=9.35, N=5.43.

Preparation of compounds 412, 413, 417, and 449: These compounds were produced using procedures analogous to those above in this Example.

α-Amino 412: $^1$H NMR (400 MHz, CD$_3$OD) δ: 3.83 (m, 1H), 3.00 (br m, 1H), 1.04 (s, 3H), 0.96 (d, J=6 Hz, 3H), 0.74 (s, 3H); IR (KBr, cm$^{-1}$): 3413, 2942, 2061, 1710, 1594, 1460, 1377, 1167, 1074; MS(+FAB): 577.7 (M+1); Anal. calcd. for C$_{34}$H$_{64}$N$_4$O$_3$-4HCl-2.5H$_2$O: C=53.19, H=9.58, N=7.30; Found: C=53.27, H=9.47, N=7.32.

β-Amino 413: $^1$H NMR (400 MHz, CD$_3$OD) δ: 3.8 (m, 1H), 3.4 (m, 1H), 1.05 (s, 3H), 0.96 (d, J=6 Hz, 3H), 0.73 (s, 3H); MS(+FAB): 577.7 (M+1).

Deoxycholic acid ethylenediamine 417 (α-amino isomer): $^1$H NMR (400 MHz, CD$_3$OD) δ: 4.03 (m, 1H), 3.22 (br m, 1H), 1.03 (d, J=6 Hz, 3H), 1.00 (s, 3H), 0.74 (s, 3H); IR (KBr, cm$^{-1}$): 2940, 1706, 1456, 1379, 1254, 1034; MS(+FAB): 435.4 (M+1); Anal. calcd. for C$_{26}$H$_{46}$N$_2$O$_3$-2HCl-2H$_2$O: C=57.45, H=9.64, N=5.15; Found: C=57.32, H=9.22, N=5.13.

Deoxycholic acid spermine 449 (α-amino isomer): $^1$H NMR (400 MHz, CD$_3$OD) δ: 4.02 (m, 1H), 1.04 (d, J=6 Hz, 3H), 1.00 (s, 3H), 0.75 (s, 3H); IR (KBr, cm$^{-1}$): 2941, 1716, 1448, 1038; MS(+FAB): 577.4 (M+1); Anal. calcd. for C$_{34}$H$_{64}$N$_4$O$_3$-4HCl-1.5H$_2$O: C=54.57, H=9.54, N=7.47; Found: C=54.31, H=8.71, N=7.80.

Example J

Preparation of compounds 566 and 569:

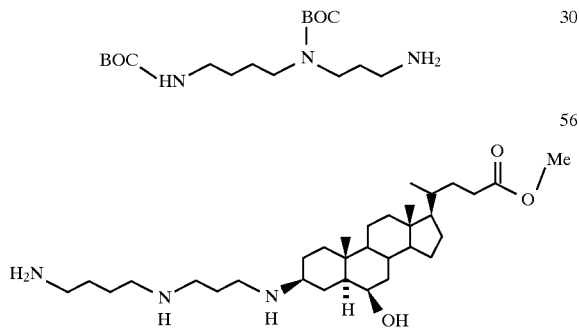

Preparation of compound 566. Compound 566 was prepared in an analogous manner to that used for compound 466, but using polyamine 301 instead of spermine. The product of the reductive coupling was deprotected with trifluoroacetic acid to remove the BOC groups and yield compound 566. Compound 566: $^1$H NMR (400 MHz, CD$_3$OD): δ3.74 (m, 1H), 3.61 (s, 3H), 3.3–2.9 (m, 9H), 2.4–1.0 (m, 32H), 1.01 (s, 3H), 0.90 (d, J=6 Hz, 3H), 0.70 (s, 3H); MS (+FAB): 534.4 (M+1); Anal. calcd. for C$_{32}$H$_{59}$N$_3$O$_3$-3TFA: C=52.1 1, H=7.13, N=4.80; Found: C=52.02, H=6.97, N=4.67.

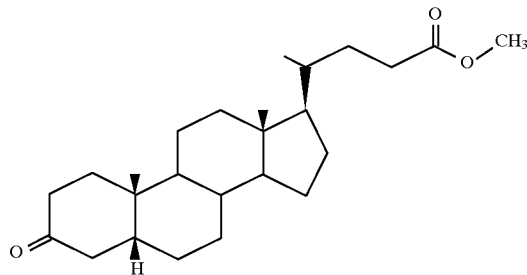

Preparation of compound 569. Compound 569 was prepared in an analogous manner to compound 466, but methyl 3-oxo-5β-cholanoate (from Steraloids Inc.) was used as the starting steroid component. Compound 569: MS (+FAB):

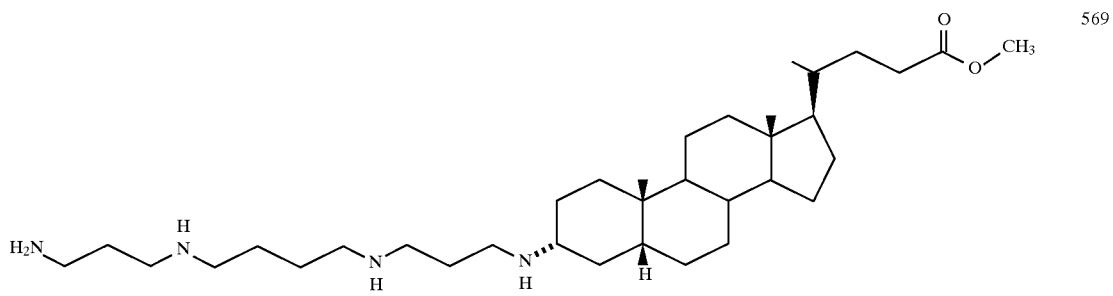

575.5 (M+1); $^1$H NMR (400 MHz, CD$_3$OD): δ3.61 (s, 3H), 3.1–3.0 (m, 12H), 2.3–1.0 (m, 36H), 1.00 (s, 3H), 0.90 (d, J=6 Hz, 3H), 0.66 (s, 3H); Anal. calcd. for C$_{35}$H$_{66}$N$_4$O$_2$-4TFA: C=50.09, H=6.84, N=5.43, F=22.11; Found: C=50.04, H=6.41, N=5.21, F=20.66.

Based on the above description, one skilled in the art would be capable of producing additional aminosterol ester compounds that fall within the general formula identified above through routine experimentation.

PROPERTIES OF THE AMINOSTEROL ESTERS

Various properties of specific aminosterol esters are described below. Some properties are described in comparison with other aminosterols, such as squalamine, compound 1436, and compound 1437.

Inhibition of Endothelial Cell Cord Formation In Vitro

Endothelial cells have the capacity in vitro to form tubular aggregates resembling capillaries in various early stages of formation. This conversion occurs under relatively specific conditions, in which essential growth factors along with an effective substratum are provided. It has been shown that both the interaction of growth factors with the endothelial cell and its attachment to a substratum activate the NHE. The activation of this exchanger is believed to be required for subsequent morphologic transformation of the endothelial cell into a multicellular tubular structure.

To assess the effect of compounds on the cord-like structures formed by human microvascular cells when plated in the presence of VEGF (Vascular Endothelial Growth Factor) and basic fibroblast growth factor on a collagen matrix, a standard cord formation assay was performed using the method described by Goto, et al., "Synergistic Effects of Vascular Endothelial Growth Factor and Basic Fibroblast Growth Factor on the Proliferation and Cord Formation of Bovine Capillary Endothelial Cells Within Collagen Gels," Laboratory Investigation, Vol. 69, No. 5, 1993, pp. 508–517. This article is entirely incorporated herein by reference. The test results are shown in the table below.

| EFFECT OF VARIOUS AMINOSTEROLS ON ENDOTHELIAL CORD FORMATION | | | | |
|---|---|---|---|---|
| | μg/ml | | | |
| | 0.01 | 0.1 | 1.0 | 10.0 |
| Fumagillin | | − | +/− | + |
| Squalamine | − | + | + | + |
| Compound 319 | − | + | + | + |
| Compound 353 | | + | + | + |
| Compound 410 | | − | + | +* |
| Compound 411 | | − | − | + |
| Compound 412 | | − | − | + |
| Compound 413 | | − | − | + |
| Compound 415 | | − | − | +/T |
| Compound 432 | | | − | − |
| Compound 449 | | | − | +/− |
| Compound 467 | | | − | − |

Notes:
+ = Inhibition of angiogenesis;
− = No inhibition of angiogenesis;
T = Toxic;
* = cell rounding @ 10 μg/ml.

As shown in the above Table, squalamine inhibits cord formation at about 0.1 μg/ml, compared with fumagillin, which exhibits comparable activity at 10 μg/ml. At these concentrations, squalamine does not appear to profoundly affect cell viability or proliferation. This property in vitro roughly correlates with anti-angiogenic activity in more complex in vivo models (see Goto et al., *Lab Investigation* 69, 1993, 508–518, which article is entirely incorporated herein by reference). Notably, ester compounds 410 and 411 also inhibit angiogenesis at higher doses.

The Vitelline Capillaries of 3–5 Day Chick Embryo Model

In the course of evaluating squalamine in the "classical" chick chorioallantoic membrane model, it was noted that this steroid exerted a dramatic and rapid effect on capillary vessel integrity in the three- to five-day old chick embryo. Using the chick embryo vitelline capillaries assay, various aminosterol compounds were tested for their ability to induce capillary regression. Each compound was applied in 0.1 ml of 15% Ficol 400 and PBS onto the embryo, and vascular regression was assessed after 60 minutes. These tests were conducted by the chorioallantoic membrane anti-angiogenesis assay by applying the material to be assayed to 3 day old fertilized chick embryos in the manner described by Wilks et al., "Inhibition of Angiogenesis With Combination Angiostatic Steroids and Suramin," *Radiation Biology*, Vol. 60, Nos. 1/2, 1991, pp. 73–77, which article is entirely incorporated herein by reference.

Squalamine was found to disrupt vitelline capillaries in 3- to 5-day chick embryos. The 3-day chick embryo consists of an embryonic disc from which numerous vessels emerge and return, forming a "figure 8"-shaped structure—the embryo in the center with vascular loops extending outward over both poles. Application of squalamine onto the embryonic structure (0.1 ml in 15% Ficol in PBS) resulted in progressive "beading up" of the vitelline vessels, with the finest capillaries being the first to exhibit these changes. Following a lag period of around 15 minutes, the constriction of continuity between capillary and secondary vessels, generally on the "venous" side, was observed. Continued pulsatile blood flow progressed, resulting in a "swelling" of the blind tube, followed by a pinching off of the remaining connection and formation of an enclosed vascular sac resembling a "blood island." This process progressed until only the largest vessels remained intact. The embryonic heart continued to beat vigorously. No hemorrhage was seen, reflecting the integrity of the capillary structure. In addition, no obvious disruption of circulating red cells was observed microscopically, demonstrating the absence of hemolysis.

Utilizing this assay, which appears to demonstrate what is commonly called capillary "regression," a minimum concentration of squalamine and other aminosterol compounds required to observe an effect in 60 minutes can be determined. Results are summarized in the table below.

| EFFECTS OF VARIOUS AMINOSTEROLS IN CHICK EMBRYO VITELLINE CAPILLARY REGRESSION ASSAY | | | | | |
|---|---|---|---|---|---|
| | Amount of Compound Applied (μg) | | | | |
| Compound | 10 | 1 | 0.1 | 0.01 | 0.001 |
| Compound 1436 | + | + | + | + | +/− |
| Compound 319 | + | + | + | + | +/− |
| squalamine | + | + | + | + | 0 |
| Compound 415 | | + | + | + | 0 |
| Compound 410 | | + | +/− | +/− | 0 |
| Compound 412 | | + | 0 | 0 | 0 |
| Compound 411 | | +/− | 0 | 0 | 0 |
| Compound 382 | + | + | 0 | 0 | 0 |
| Compound 396 | | + | 0 | 0 | 0 |
| Compound 353 | | +/− | | | |
| Compound 413 | | 0 | | | |
| Compound 414 | | 0 | | | |
| Compound 381 | | 0 | | | |
| Compound 303 | | 0 | | | |
| Compound 318 | | 0 | | | |
| Compound 409 | | 0 | | | |
| Vehicle | 0 | 0 | 0 | 0 | 0 |

Notes:
+ = Vascular reactivity;
0 = No vascular reactivity;
+/− = Equivocal reactivity;
Vehicle = 15% (w/w) Ficol in phosphate-buffered saline.

As apparent from the above Table, 0.1–0.01 μg of squalamine in 0.1 ml medium can induce changes. Compounds having various ranges of activities were found, with squalamine, compound 319, and compound 415 being especially active. Additionally, ester compound 410 demonstrated substantial activity in this assay. This experiment demonstrates that the steroids tested can dramatically restructure capillaries over a time interval amounting to several minutes. The results reflect that this effect is accomplished through inhibition of NHE.

Tadpole Assay

A tadpole assay was conducted to test the properties of various aminosterols. This tadpole assay is described in U.S. patent application Ser. No. 08/483,059. For this assay, tadpoles, preferably *Xenopus laevis* Stages 59–60 tadpoles, were employed to study the effect of a compound by monitoring capillary occlusion in the tadpole's tail. Animals at these stages were used because they represent the period of transition through metamorphosis at which time the animal possess both embryonic and adult stage tissues. Compounds, when tested in this assay, can affect the shape, viability, and integrity of the embryonic tissues while not affecting the adult tissues, providing a powerful, highly specific screen. For example, substances that destroy all of the animal's epithelium, both adult and embryonic, could be regarded as toxic. Substances that destroy only the embryonic tissues exhibit a very unique specificity.

In this assay, tadpoles are introduced into Petri dishes containing a solution of the test compound in distilled water, preferably about 100 ml. The preferred concentration of the test compound is from about 1 μg/ml to about 10 μg/ml. The volume of liquid is sufficient for the animal to swim freely and drink from the solution. Thus, the effect observed results from oral absorption and subsequent systemic distribution of the agent. If the volume of liquid is not sufficient to permit oral intake, the effects that are observed would result from absorption through the surface epithelium. Thus, this simple assay can identify if an compound has characteristics of oral availability.

In another embodiment of this assay, a solution of a compound in water can be injected directly into the abdomen of the animal using standard techniques. Concentrations of the compound from about 0.05 mg/ml to about 0.5 mg/ml in about 0.05 ml of water are preferred.

After an amount of time, typically about 60 minutes, the occlusion of blood flow through capillaries in the tadpole's tail are observed under an inverted microscope at a magnification of roughly 100×.

When the tadpoles were introduced into distilled water containing squalamine at 10 μg/ml, it was observed that blood flow through the capillaries of the tail shut down. The process occurred from the caudal to cranial direction. Blood flow within the most distal vessels stopped initially, followed by the larger vessels. During this period, it was observed that the cardiovascular system was otherwise robust, as evidenced by a continued heartbeat, pulsatile expansion of the great vessels, and, most curiously, unaltered blood flow through the fine capillaries of the hands and feet. Thus, selective cessation of blood flow was seen in localized regions. If the animals are maintained in squalamine for several days, enhanced regression of the most distal aspects of the tail, as well as the peripheral aspects of the tail fin are observed, corresponding to regions of the animal perfused by the occluded vasculature.

This effect apparently results from selective change in the resting diameter of the capillaries of the tail. Inhibition of the endothelial cell NHE evidently leads to a change in shape of the cell making up the capillary, resulting in diminished flow. The continued functioning of capillary beds in the "adult" portions of the tadpole (the limbs) indicates that squalamine is selective for certain capillaries. From the results of the tadpole tail capillary occlusion assay, compound 319, squalamine and compound 1436 were found to induce a common vascular occlusive effect.

Various other aminosterols were tested in the tadpole assay. Compound 1437, described, for example in U.S. patent appl. Ser. No. 08/483,059, contains an unusual ergosterol-like side chain. In the tadpole assay, this molecule can be distinguished readily from other steroids extracted from shark on the basis of its dramatic effect on the embryonic epithelium covering the tadpole tail.

Using the tadpole assay described above, within 60 minutes of exposure to steroid 1437 at 10 μg/ml, the larval skin was observed to shed off in a sheet. The rapid appearance of the process suggests that an NHE expressed by this epithelial tissue is the target. Since NHE activity and cell membrane proteins involved in adhesion cross-communicate (Schwartz et al., Proc. Nat'l. Acad. Sci. 888, 7849–7853, which article is entirely incorporated herein by reference), it is proposed that inhibition of NHE on the epithelium results in disruption of cellular contacts between the epithelium and its substratum, leading to a shedding effect.

Because of the results in the assay described above, the anticancer effects of compound 1437 against several cancer lines was assessed. Compound 1437 was found to exhibit anticancer activity against the human ovarian carcinoma, SKOV3. Thus, compound 1437 should find use in the treatment of carcinomas exhibiting a sensitive phenotype.

As the study above demonstrates, compound 1437 targets a "mesothelium-like" epithelial layer, a skin layer that is comprised of only one cellular layer. Such a layer resembles epithelial surfaces such as the human peritoneum, synovium, pericardium and ependyma.

Accordingly, compound 1437 should exhibit antiproliferative effects on these tissues and malignancies which derive from them. In addition, these tissues can support viral infections, and therefore in these instances the compound should provide therapeutic antiviral benefit.

By use of the Xenopus tadpole assay, it was possible to identify compounds that exhibit little chemical resemblance to compound 1437, but produce the same pharmacological effect with respect to epithelial shedding. Using such a method, it was found that aminosterol esters 409, 410, 416, 431, and 432 are functionally similar to compound 1437.

Antimicrobial and Other Activity

The aminosterol NHE inhibitors represent a class of antibiotics based on mechanism of action. Because these agents also interact with specific NHE isoforms in human tissues, prudent selection of an antibiotic of this class can eliminate undesirable side effects, due to host NHE inhibition, or potentiate the therapeutic intent. Thus, use of an agent like compound 1436 would suppress lymphoid proliferation during active treatment of an infection. An effective antifungal agent can be designed further to increase specificity for its pathogenic target over sensitive vertebrate isoforms.

As seen in Table I at the end of this specification, the antibacterial/antifungal spectrum differs from compound to compound. Thus, it is possible to achieve an antimicrobial steroid with or without squalamine-like pharmacological activity.

As set forth in Table II, which follows Table I, the activities of natural and synthetic aminosterols in the different assays vary. In light of the foregoing, it is now possible to screen for steroids with or without squalamine-like pharmacological activity.

Table III, following Table II, shows various properties of aminosterol ester compound 569. Notably, this aminosterol compound has higher inhibition of HIV than compound 1436.

Additional properties of certain aminosterol compounds described above are shown in Table IV. Notably, compound 469 has a higher potency in the mitogen proliferation assay than compound 1436. See Table IV. Aminosterol esters 459, 569, and 466 also have substantial potency in this assay, as shown in Table IV.

In Table V, several aminosterol esters show efficacy in killing melanoma cells in the MTT assay. Notably, many of them are more potent than compound 1436 in this assay.

Furthermore, like compound 1361, compounds 459, 466, and 566 have been found to induce swelling of red blood cells. This activity is believed to make compounds 459, 466, and 566 useful for treatment of malaria or sickle cell anemia.

For the attached Tables, the mitogen proliferation assay was performed by treating mice (male or female) with various amounts of the aminosterol test compounds. Some time later (typically between 2 hours and 14 days), the mice are sacrificed and their spleens removed. Splenocytes are harvested and cultured in the presence of between 1–10

μg/ml of Con A (Sigma) for 48 hours. See James Morgan, "Monoclonal Antibody Production," *Modern Methods in Pharmacology*, pp. 29–67, eds., Spector and Back, 1988. This excerpt is entirely incorporated herein by reference. Cell proliferation is monitored either by direct cell counting or by measurement of the incorporation of radioactive thymidine.

The MTT assay for cell number is performed as follows. Cells are counted on a hemocytometer and diluted to a concentration of approx. 10,000 cells/well (55,000 cells/ml× 0.18 ml). Cells are then plated in a 96 well microtiter plate and allowed to attach overnight. The next day, compounds are serially diluted from 1000 to 15.6 μg/ml and run in duplicate. 20 μl of each dilution are transferred to the pre-seeded microtiter plates. The final concentrations are 100 to 1.56 μg/ml. The plates are then incubated for 48 hours at 37° C. in 5% $CO_2$. After 48 hours, MTT solution is added. The plate is re-incubated for 4 hours. Readings are done by removing all but 30 μl of media and MTT solution and dissolving the formazan crystals with DMSO. The formazan is dissolved by mixing on a rotating plate at low speed for about 30 minutes. Absorbance of converted dye is measured at a wavelength of 560 nm with background subtraction at 630 nm. The percent survival is determined by a comparison between the mean absorbance of the duplicate test lanes and the growth control.

The protocol for analyzing the activity of an aminosterol against HIV and SIV replication in vitro ("HIV Inhib.") was as follows. The effect of the aminosterols was tested on recall antigen-induced HIV replication from peripheral blood mononuclear cells (PBMC) of an HIV-infected subject. PBMC from an HIV(+), PPD(+) subject were isolated by ficoll hypaque density gradient, and CD8+ cells were depleted (>98% depleted) by immunomagnetic bead separation. CD8– depleted PBMC (1.5 million/well) were plated in RPMI+ 10% FCS (p/s, glutamine, herpes; 1 mM) containing 1 mM aminoguanidine and exposed to various concentrations of aminosterols (0–15, 15 μM) for 1 hour prior to stimulation of the cells with the recall antigen PPD (1 μg/ml) or with the mitogen (lectin), PHA. Culture supernatants were harvested (frozen at –80° C.) and cultures refed with media ± the aminosterol every three days (PHA-stimulated wells also received 10 U/ml interleukin IL-2). Culture supernatants were later thawed and analyzed for HIV replication by determination of HIV reverse transcriptase (RT) activity by standard 32P TTP incorporation assays (Wiley, R., et al., *Journal Virology*, 1988, which article is entirely incorporated herein by reference). On Day 7 post-stimulation, cells from each test were removed (1/10 volume of the resuspended culture) for analysis of proliferative activity by standard 3H thymidine incorporation assays.

THERAPEUTIC ADMINISTRATION AND COMPOSITIONS

The mode of administration of aminosterol compounds of the invention may be selected to suit the particular therapeutic use. Modes of administration generally include, but are not limited to, transdermal, intramuscular, intraperitoneal, intravenous, subcutaneous, intranasal, inhalation, intralesional, endothelial and oral routes. The compounds of the invention may be administered by any convenient route, for example, by infusion or bolus injection, or by absorption through epithelial or mucocutaneous linings (e.g., oral mucosa, rectal, and intestinal mucosa, etc.), and the active aminosterol ingredient may be administered together with other biologically active agents. Administration may be local or systemic.

The present invention also provides pharmaceutical compositions that include one or more aminosterol compounds as an active ingredient. Such pharmaceutical compositions include a therapeutically effective amount of the aminosterol compounds (or a pharmaceutically acceptable salt thereof) and a pharmaceutically acceptable carrier or excipient. Examples of such a carrier include, but are not limited to, saline, buffered saline, dextrose, water, glycerol, ethanol, and combinations thereof. The particular form and formulation of the pharmaceutical composition should be selected to suit the mode of administration.

The pharmaceutical composition, if desired, also may contain minor amounts of wetting or emulsifying agents, or pH buffering agents. The pharmaceutical composition may be in any suitable form, such as a liquid solution, suspension, emulsion, tablet, pill, capsule, sustained release formulation, or powder. The pharmaceutical composition also may be formulated as a suppository, with traditional binders and carriers, such as triglycerides. Oral formulations may include standard carriers, such as pharmaceutical grades of mannitol, lactose, starch, magnesium stearate, sodium saccharine, cellulose, magnesium carbonate, etc.

Various delivery systems are known and may be used to administer a therapeutic compound of the invention, e.g., encapsulation in liposomes, microparticles, microcapsules and the like.

In one embodiment, the pharmaceutical composition is formulated in accordance with routine procedures as a pharmaceutical composition adapted for intravenous administration to humans. Typically, compositions for intravenous administration are solutions in sterile isotonic aqueous buffer. Where necessary, the pharmaceutical composition also may include a solubilizing agent and a local anesthetic to ameliorate pain at the cite of the injection. Generally, the ingredients are supplied either separately or mixed together in unit dosage form, for example, as a dry lyophilized powder or water-free concentrate in a hermetically sealed container such as an ampule or sachette indicating the quantity of active agent. Where the pharmaceutical composition is to be administered by infusion, it may be dispensed with an infusion bottle containing sterile pharmaceutical grade water or saline. Where the pharmaceutical composition is administered by injection, an ampoule of sterile water for injection or saline may be provided so that the ingredients may be mixed prior to administration.

The amount of the therapeutic compound of the invention that will be effective in the treatment of a particular disorder or condition will depend oil the nature of the disorder or condition, and this amount can be determined by standard clinical techniques known to those skilled in the art through routine experimentation. The precise dose to be employed in the pharmaceutical composition also will depend on the route of administration and the seriousness of the disease or disorder, and should be decided according to the judgement of the practitioner and each patient's circumstances. Effective therapeutical doses may be determined from extrapolations of dose-response curves derived from in vitro or animal-model test systems.

The following dosage ranges are exemplary. Suitable dosages for intravenous administration are generally about 20 micrograms to 40 milligrams of active compound per kilogram body weight. Suitable dosage ranges for intranasal administration are generally about 0.01 mg/kg body weight to 1 mg/kg body weight. Suitable concentrations for topical 5 administration are generally at least about 0.01% by weight. Suitable dosages for oral administration are generally about 500 micrograms to 800 milligrams per kilogram body weight, and preferably about 1–200 mg/kg body weight. Suppositories generally contain, as the active ingredient, 0.5 to 10% by weight of the aminosterol compounds. Oral formulations preferably contain 10% to 95% active ingredient.

Exemplary dosages of the aminosterol compounds for most pharmacological or therapeutical uses fall within the range of about 0.01 mg/kg body weight to about 100 mg/kg body weight. Preferred dosages are from 0.1 to 25 mg/kg body weight.

The invention also may include a pharmaceutical pack or kit including one or more containers filled with pharmaceutical compositions in accordance with the invention. Associated with such containers may be a notice in the form prescribed by a government agency regulating the manufacture, use or sale of pharmaceuticals or biological products, which notice reflects approval by the agency of manufacture, use or sale for human administration.

By the term "effective amount" in this application, applicants refer to a suitable amount of the active ingredient of the invention, with an appropriate carrier or excipient, including a sufficient amount of the active ingredient to provide the desired effects or results. The effective amount can be readily ascertained by those skilled in the art through routine experimentation.

In describing the invention, applicants have stated certain theories in an effort to disclose how and why the invention works in the manner in which it works. These theories are set forth for informational purposes only. Applicants do not wish to be bound by any specific theory of operation.

While the invention has been described in terms of various specific preferred embodiments and specific examples, those skilled in the art will recognize that various changes and modifications can be made without departing from the spirit and scope of the invention, as defined in the appended claims.

TABLE I

ANTIBIOTIC ACTIVITY OF NATURAL AND SYNTHETIC AMINOSTEROLS

| Structure | MIC Values (μg/mL) | | | |
|---|---|---|---|---|
| | S. aureus | E. Coli | P. aerug | C. albicans |
| Compound 303 | 8 | 128–256 | 128 | 256 |
| MSI-1256 | 0.5–1 | 2–4 | 16 | 8 |
| Compound 304 | 2–4 | 128 | 128 | 128 |

TABLE I-continued
ANTIBIOTIC ACTIVITY OF NATURAL AND SYNTHETIC AMINOSTEROLS
| Structure | MIC Values (μg/mL) | | | |
|---|---|---|---|---|
| | S. aureus | E. Coli | P. aerug | C. albicans |
| Compound 319 | 64 | 32–64 | 32 | 8 |
| Compound 318 | 128 | 32 | 64 | >256 |
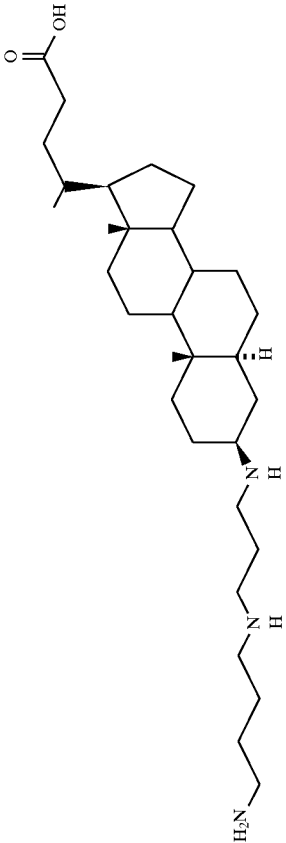
Compound 319
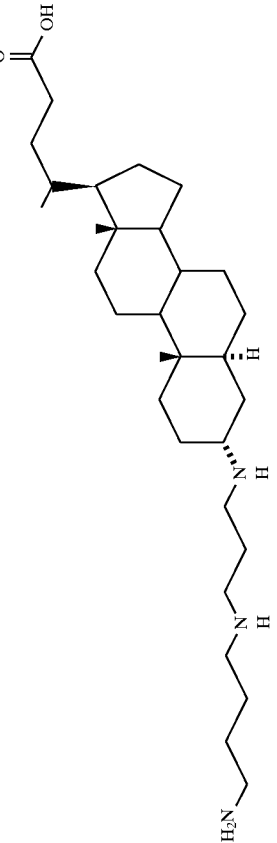
Compound 318

TABLE I-continued

ANTIBIOTIC ACTIVITY OF NATURAL AND SYNTHETIC AMINOSTEROLS

| Structure | MIC Values (µg/mL) | | | |
|---|---|---|---|---|
| | S. aureus | E. Coli | P. aerug | C. albicans |
| Compound 353 | 16 | 128 | 64 | 32 |
| Compound 354 | 8 | 64–128 | 64 | 16–32 |
| Compound 380 | 4–8 | 32 | 64 | 32 |

TABLE I-continued
ANTIBIOTIC ACTIVITY OF NATURAL AND SYNTHETIC AMINOSTEROLS
| Structure | MIC Values (μg/mL) | | | |
|---|---|---|---|---|
| | S. aureus | E. Coli | P. aerug | C. albicans |
| 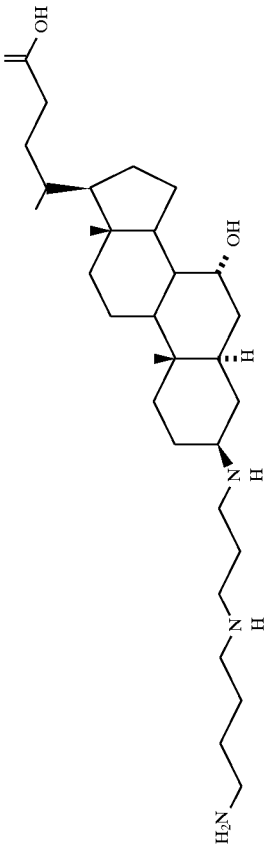 Compound 381 | 32 | 64 | 32 | 128 |
| 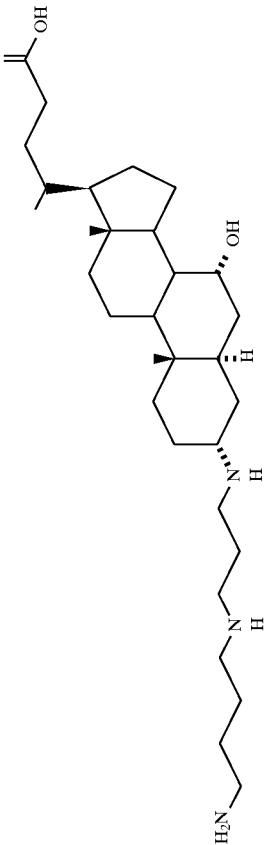 Compound 382 | 16 | 64 | 32 | 32 |

TABLE I-continued
ANTIBIOTIC ACTIVITY OF NATURAL AND SYNTHETIC AMINOSTEROLS
| Structure | MIC Values (μg/mL) | | | |
|---|---|---|---|---|
| | S. aureus | E. Coli | P. aerug | C. albicans |
| Compound 394 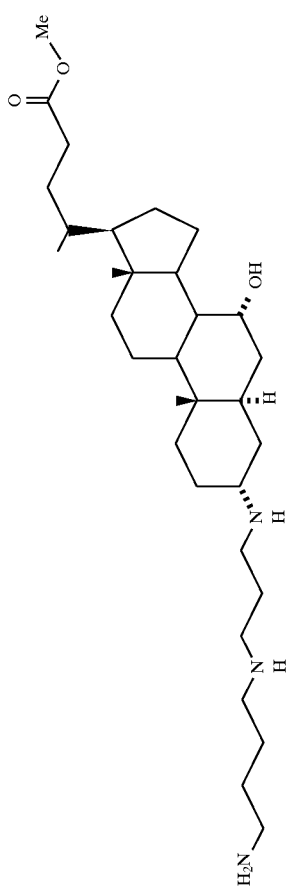 | 4 | 64 | 64 | 32 |
| Compound 395 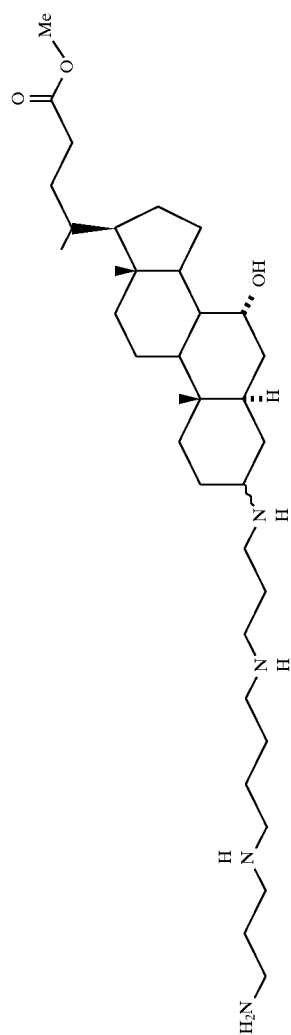 | 4 | 32 | 64 | 64 |

TABLE I-continued

ANTIBIOTIC ACTIVITY OF NATURAL AND SYNTHETIC AMINOSTEROLS

| Structure | MIC Values (μg/mL) | | | |
|---|---|---|---|---|
| | S. aureus | E. Coli | P. aerug | C. albicans |
| Compound 396 | 2–4 | 64 | 128 | 16 |
| Compound 397 | 16 | 32–64 | 16 | 32 |

TABLE I-continued
ANTIBIOTIC ACTIVITY OF NATURAL AND SYNTHETIC AMINOSTEROLS
| Structure | MIC Values (μg/mL) | | | |
|---|---|---|---|---|
| | S. aureus | E. Coli | P. aerug | C. albicans |
| Compound 355 | 64 | 256 | >256 | 256 |
| Compound 356 | 4 | 32–64 | 64 | 64 |
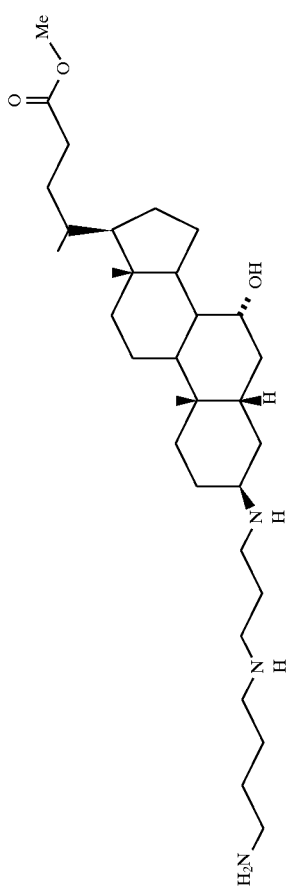
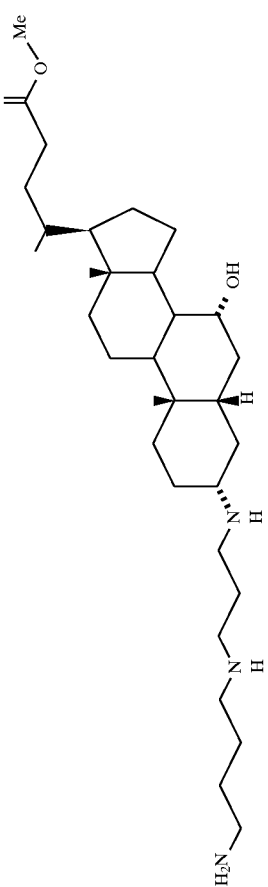

TABLE I-continued

ANTIBIOTIC ACTIVITY OF NATURAL AND SYNTHETIC AMINOSTEROLS

| Structure | MIC Values (μg/mL) | | | |
|---|---|---|---|---|
| | S. aureus | E. Coli | P. aerug | C. albicans |
| Compound 409 | 32 | 64 | 128 | 16 |
| Compound 410 | 16 | 16 | 32 | 16 |

TABLE I-continued
ANTIBIOTIC ACTIVITY OF NATURAL AND SYNTHETIC AMINOSTEROLS
| Structure | MIC Values (μg/mL) | | | |
|---|---|---|---|---|
| | S. aureus | E. Coli | P. aerug | C. albicans |
| Compound 411 | 8 | 64 | 64 | 2 |
| Compound 412 | 64 | 8 | 8 | 8 |
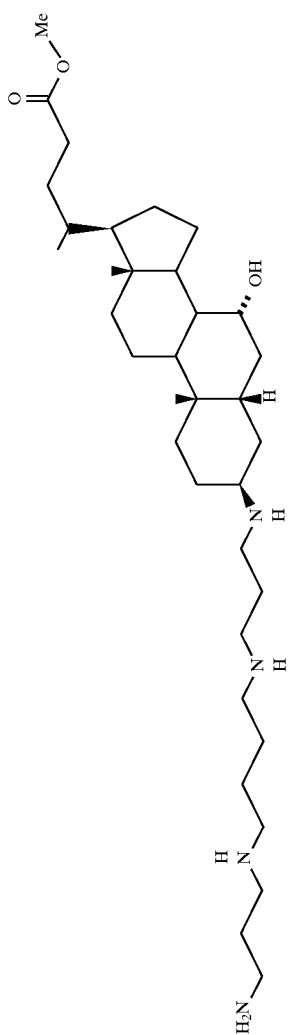

TABLE I-continued

ANTIBIOTIC ACTIVITY OF NATURAL AND SYNTHETIC AMINOSTEROLS

| Structure | MIC Values (μg/mL) | | | |
|---|---|---|---|---|
| | S. aureus | E. Coli | P. aerug | C. albicans |
| Compound 413 | 8 | 256 | 64 | 32 |
| Compound 414 | 32 | 64 | 64 | 64 |

TABLE I-continued

ANTIBIOTIC ACTIVITY OF NATURAL AND SYNTHETIC AMINOSTEROLS

| Structure | MIC Values (μg/mL) | | | |
|---|---|---|---|---|
| | S. aureus | E. Coli | P. aerug | C. albicans |
| Compound 415 | 128 | 128 | 256 | 256 |
| Compound 416 | 8 | 8 | 16–32 | 32 |

TABLE I-continued

ANTIBIOTIC ACTIVITY OF NATURAL AND SYNTHETIC AMINOSTEROLS

| Structure | MIC Values (μg/mL) | | | |
|---|---|---|---|---|
| | S. aureus | E. Coli | P. aerug | C. albicans |
| Compound 417 | 16–32 | 64 | 128 | 32 |
| Compound 431 | 16 | 32–44 | 128 | 8 |

TABLE I-continued
ANTIBIOTIC ACTIVITY OF NATURAL AND SYNTHETIC AMINOSTEROLS
| Structure | MIC Values (μg/mL) | | | |
| --- | --- | --- | --- | --- |
| | S. aureus | E. Coli | P. aerug | C. albicans |
| 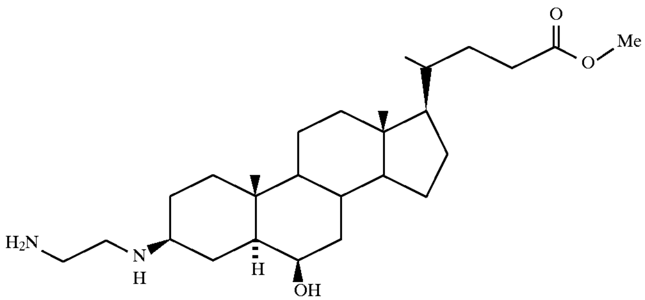 | 1 | 8–16 | 64 | 2–4 |
| Compound 432 | >256 | >256 | 128 | |
| Compound 433 | | | | >256 |
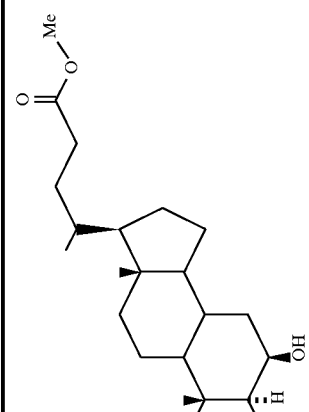
Compound 432
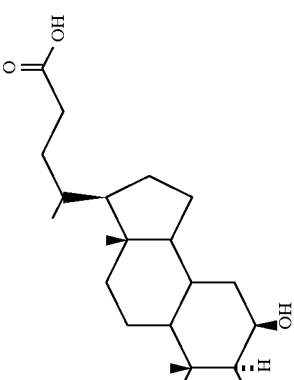
Compound 433

TABLE I-continued
ANTIBIOTIC ACTIVITY OF NATURAL AND SYNTHETIC AMINOSTEROLS
| Structure | MIC Values (μg/mL) | | | |
|---|---|---|---|---|
| | S. aureus | E. Coli | P. aerug | C. albicans |
| Compound 1436 | 1 | 1–2 | 4 | 8 |
| Compound 1437 | 2 | 4 | 16 | 16 |
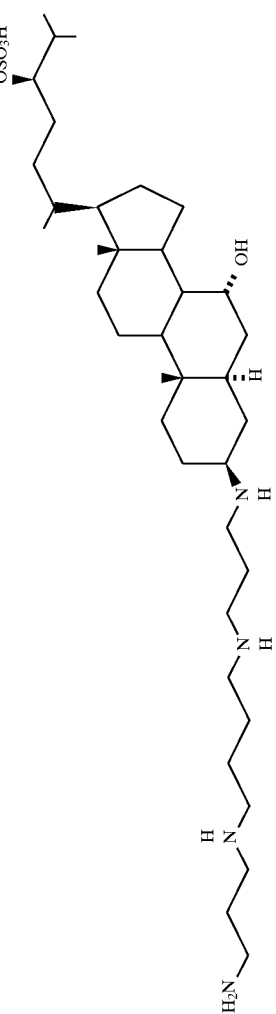

TABLE I-continued

ANTIBIOTIC ACTIVITY OF NATURAL AND SYNTHETIC AMINOSTEROLS

| Structure | MIC Values (μg/mL) | | | |
|---|---|---|---|---|
| | S. aureus | E. Coli | P. aerug | C. albicans |
| Compound 448 | 2 | 16 | 8 | 8 |
| Compound 449 | 4 | 8–16 | 4 | 4 |

TABLE I-continued
ANTIBIOTIC ACTIVITY OF NATURAL AND SYNTHETIC AMINOSTEROLS
| Structure | MIC Values (μg/mL) | | | |
|---|---|---|---|---|
| | S. aureus | E. Coli | P. aerug | C. albicans |
| Compound 458 | 4 | 32 | 64 | 2 |
| Compound 459 | 1–2 | 32 | 64 | 2 |
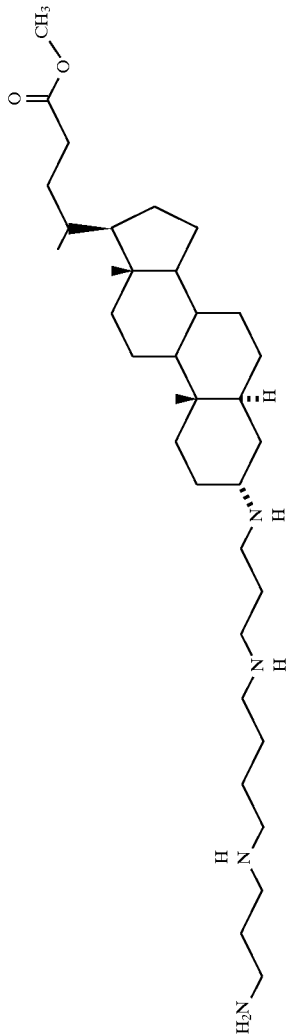
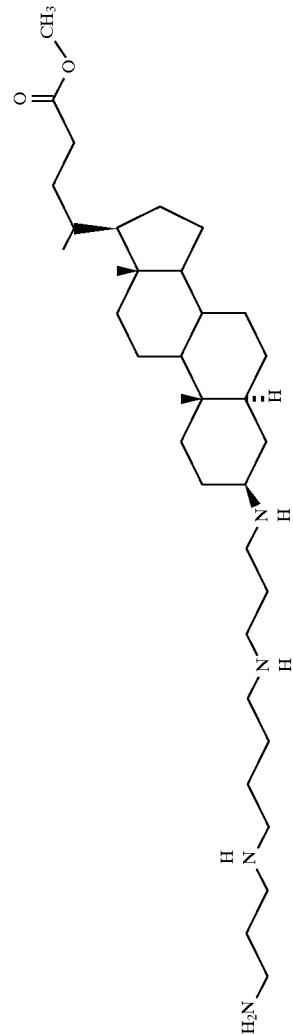

TABLE I-continued

ANTIBIOTIC ACTIVITY OF NATURAL AND SYNTHETIC AMINOSTEROLS

| Structure | MIC Values (μg/mL) | | | |
| --- | --- | --- | --- | --- |
| | S. aureus | E. Coli | P. aerug | C. albicans |
| Compound 465 | 2–4 | 32 | 128 | 4 |
| Compound 466 | 2 | 32 | 32 | 2 |

TABLE I-continued

ANTIBIOTIC ACTIVITY OF NATURAL AND SYNTHETIC AMINOSTEROLS

| Structure | MIC Values (μg/mL) | | | |
|---|---|---|---|---|
| | S. aureus | E. Coli | P. aerug | C. albicans |
| Compound 467 | 16 | 16 | 8 | 4 |

TABLE II

ACTIVITY OF NATURAL AND SYNTHETIC AMINOSTEROLS
IN CHICK EMBRYO AND TADPOLE ASSAYS

| Structure | Chick embryo diss. assay (µg) | Tadpole (10 µg/mL) | | | | | | Cord Formation (µg/mL) | HM MTT assay (µg/mL) | LLC MTT (µg/mL) |
|---|---|---|---|---|---|---|---|---|---|---|
| | | V | M | E | TB | GI | Mus | Tox | | | |
| 303 | >10 | - | - | - | - | - | - | - | | | |
| 318 | >10 | - | - | - | - | - | - | - | | | |

TABLE II-continued

ACTIVITY OF NATURAL AND SYNTHETIC AMINOSTEROLS
IN CHICK EMBRYO AND TADPOLE ASSAYS

| Structure | Chick embryo diss. assay (μg) | Tadpole (10 μg/mL) | | | | | | | Cord Formation (μg/mL) | HM MTT assay (μg/mL) | LLC MTT (μg/mL) |
|---|---|---|---|---|---|---|---|---|---|---|---|
| | | V | M | E | TB | GI | Mus | Tox | | | |
| 319 | 0.001 | + | − | − | − | − | − | − | | 13.8 | |
| 353 | >1 | − | + | − | − | − | − | + | 10 | 3.0 | 1.9 |
| 354 | >10 | − | − | − | − | − | − | − | | | |

TABLE II-continued

ACTIVITY OF NATURAL AND SYNTHETIC AMINOSTEROLS
IN CHICK EMBRYO AND TADPOLE ASSAYS

| Structure | Chick embryo diss. assay (μg) | Tadpole (10 μg/mL) | | | | | | Cord Formation (μg/mL) | HM MTT assay (μg/mL) | LLC MTT (μg/mL) |
|---|---|---|---|---|---|---|---|---|---|---|
| | | V | M | E | TB | GI | Mus | Tox | | | |
| 355 | | + | – | – | – | – | – | ± | | | |
| 356 | | + | – | – | – | – | – | + | | | |

TABLE II-continued

ACTIVITY OF NATURAL AND SYNTHETIC AMINOSTEROLS
IN CHICK EMBRYO AND TADPOLE ASSAYS

| Structure | Chick embryo diss. assay (μg) | Tadpole (10 μg/mL) | | | | | | Cord Formation (μg/mL) | HM MTT assay (μg/mL) | LLC MTT (μg/mL) |
|---|---|---|---|---|---|---|---|---|---|---|
| | | V | M | E | TB | GI | Mus | Tox | | |
| 396 | 10 | – | – | – | – | – | – | + | | |
| 397 | 1 | – | – | – | – | – | – | + | | |

TABLE II-continued

ACTIVITY OF NATURAL AND SYNTHETIC AMINOSTEROLS
IN CHICK EMBRYO AND TADPOLE ASSAYS

| Structure | Chick embryo diss. assay (µg) | Tadpole (10 µg/mL) | | | | | | | Cord Formation (µg/mL) | HM MTT assay (µg/mL) | LLC MTT (µg/mL) |
|---|---|---|---|---|---|---|---|---|---|---|---|
| | | V | M | E | TB | GI | Mus | Tox | | | |
| 409 | >1 | − | − | + | + | − | − | + | | | |
| 410 | 0.01 | ± | − | + | + | − | − | + | | 10 | 2.6 |

TABLE II-continued

ACTIVITY OF NATURAL AND SYNTHETIC AMINOSTEROLS
IN CHICK EMBRYO AND TADPOLE ASSAYS

| Structure | Chick embryo diss. assay ($\mu$g) | Tadpole (10 $\mu$g/mL) V | M | E | TB | GI | Mus | Tox | Cord Formation ($\mu$g/mL) | HM MTT assay ($\mu$g/mL) | LLC MTT ($\mu$g/mL) |
|---|---|---|---|---|---|---|---|---|---|---|---|
| 381 | >10 | – | – | – | – | – | – | + | | | |
| 382 | 0.01 | – | – | – | – | – | – | + | | 58.6 | |

TABLE II-continued

ACTIVITY OF NATURAL AND SYNTHETIC AMINOSTEROLS
IN CHICK EMBRYO AND TADPOLE ASSAYS

| Structure | Chick embryo diss. assay ($\mu$g) | Minimum Effective Concentration ($\mu$g/mL) | | | | | | Cord Formation ($\mu$g/mL) | HM MTT assay ($\mu$g/mL) | LLC MTT ($\mu$g/mL) |
|---|---|---|---|---|---|---|---|---|---|---|
| | | Tadpole (10 $\mu$g/mL) | | | | | | | | |
| | | V | M | E | TB | GI | Mus | Tox | | |
| 394 | >10 | - | | | | | | | | |
| 395 | >10 | - | - | - | - | - | - | + | | |

TABLE II-continued

ACTIVITY OF NATURAL AND SYNTHETIC AMINOSTEROLS
IN CHICK EMBRYO AND TADPOLE ASSAYS

| Structure | Chick embryo diss. assay ($\mu$g) | Tadpole (10 $\mu$g/mL) V | M | E | TB | GI | Mus | Tox | Cord Formation ($\mu$g/mL) | HM MTT assay ($\mu$g/mL) | LLC MTT ($\mu$g/mL) |
|---|---|---|---|---|---|---|---|---|---|---|---|
| 459 | >1 | − | − | ± | − | − | + | + | | 5.0 | |
| 465 | | − | − | ± | − | − | + | + | | | |

TABLE II-continued

ACTIVITY OF NATURAL AND SYNTHETIC AMINOSTEROLS
IN CHICK EMBRYO AND TADPOLE ASSAYS

| Structure | Chick embryo diss. assay (µg) | Tadpole (10 µg/mL) | | | | | | | Cord Formation (µg/mL) | HM MTT assay (µg/mL) | LLC MTT (µg/mL) |
|---|---|---|---|---|---|---|---|---|---|---|---|
| | | V | M | E | TB | GI | Mus | Tox | | | |
| 466 | 1 | - | - | ± | - | - | + | + | | | |
| 467 | | - | - | - | - | - | - | + | | | |

TABLE II-continued

ACTIVITY OF NATURAL AND SYNTHETIC AMINOSTEROLS
IN CHICK EMBRYO AND TADPOLE ASSAYS

| Structure | Chick embryo diss. assay ($\mu$g) | Tadpole (10 $\mu$g/mL) | | | | | | Cord Formation ($\mu$g/mL) | HM MTT assay ($\mu$g/mL) | LLC MTT ($\mu$g/mL) |
|---|---|---|---|---|---|---|---|---|---|---|
| | | V | M | E | TB | GI | Mus | Tox | | | |
| 431 | >1 | ± | − | + | + | − | − | + | | | |
| 432 | >1 | − | − | + | − | − | − | + | | | |

TABLE II-continued

ACTIVITY OF NATURAL AND SYNTHETIC AMINOSTEROLS
IN CHICK EMBRYO AND TADPOLE ASSAYS

| Structure | Chick embryo diss. assay (µg) | Tadpole (10 µg/mL) | | | | | | Cord Formation (µg/mL) | HM MTT assay (µg/mL) | LLC MTT (µg/mL) |
|---|---|---|---|---|---|---|---|---|---|---|
| | | V | M | E | TB | GI | Mus | Tox | | |
| 433 | 1 | − | − | + | − | ± | − | − | | |
| 448 | 1 | ± | − | + | + | − | − | + | | |

TABLE II-continued

ACTIVITY OF NATURAL AND SYNTHETIC AMINOSTEROLS
IN CHICK EMBRYO AND TADPOLE ASSAYS

| Structure | Chick embryo diss. assay (μg) | Tadpole (10 μg/mL) | | | | | | | Cord Formation (μg/mL) | HM MTT assay (μg/mL) | LLC MTT (μg/mL) |
|---|---|---|---|---|---|---|---|---|---|---|---|
| | | V | M | E | TB | GI | Mus | Tox | | | |
| 449 | >1 | − | − | ± | ± | − | − | + | | | |
| 458 | >1 | − | − | ± | − | − | + | + | | 6.8 | |

TABLE II-continued

ACTIVITY OF NATURAL AND SYNTHETIC AMINOSTEROLS
IN CHICK EMBRYO AND TADPOLE ASSAYS

| Structure | Chick embryo diss. assay (μg) | Tadpole (10 μg/mL) | | | | | | Cord Formation (μg/mL) | HM MTT assay (μg/mL) | LLC MTT (μg/mL) |
|---|---|---|---|---|---|---|---|---|---|---|
| | | V | M | E | TB | GI | Mus | Tox | | | |
| 411 | >1 | ± | - | - | - | - | - | + | | 10 | |
| 412 | 1 | - | - | - | - | - | + | + | >10 | 18.1 | |

TABLE II-continued

ACTIVITY OF NATURAL AND SYNTHETIC AMINOSTEROLS IN CHICK EMBRYO AND TADPOLE ASSAYS

| Structure | Chick embryo diss. assay (µg) | Tadpole (10 µg/mL) V | M | E | TB | GI | Mus | Tox | Cord Formation (µg/mL) | HM MTT assay (µg/mL) | LLC MTT (µg/mL) |
|---|---|---|---|---|---|---|---|---|---|---|---|
| 413 | >1 | - | - | + | - | - | - | + | | >10 | |
| 414 | >1 | - | - | - | - | - | + | - | | | |

TABLE II-continued

ACTIVITY OF NATURAL AND SYNTHETIC AMINOSTEROLS
IN CHICK EMBRYO AND TADPOLE ASSAYS

| Structure | Chick embryo diss. assay (μg) | Tadpole (10 μg/mL) | | | | | | Cord Formation (μg/mL) | HM MTT assay (μg/mL) | LLC MTT (μg/mL) |
|---|---|---|---|---|---|---|---|---|---|---|
| | | V | M | E | TB | GI | Mus | Tox | | |
| 415 | >1 | – | – | – | – | – | – | – | >10 | |
| 416 | >1 | ± | – | + | + | – | – | + | | 2.4 |

TABLE II-continued
ACTIVITY OF NATURAL AND SYNTHETIC AMINOSTEROLS
IN CHICK EMBRYO AND TADPOLE ASSAYS
| Structure | Chick embryo diss. assay (μg) | Tadpole (10 μg/mL) V | M | E | TB | GI | Mus | Tox | Cord Formation (μg/mL) | HM MTT assay (μg/mL) | LLC MTT (μg/mL) |
|---|---|---|---|---|---|---|---|---|---|---|---|
| 417 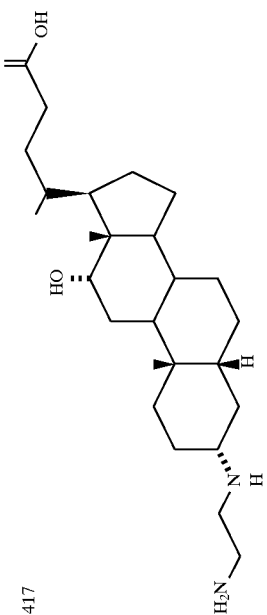 | >1 | – | – | – | – | – | – | – | | | |
| 1256 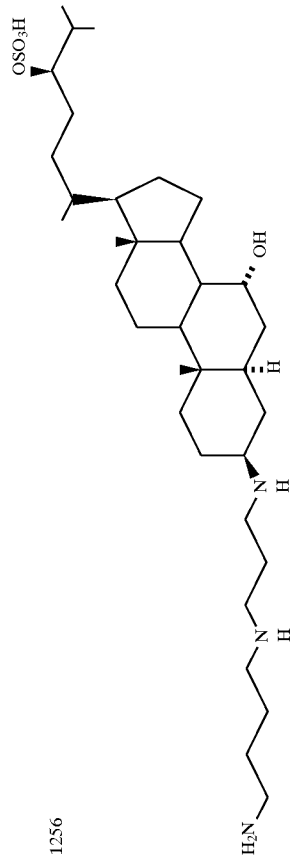 | 0.01 | + | – | – | – | – | + | – | 0.01–01 | 7.8 | 13.2 |

TABLE II-continued

ACTIVITY OF NATURAL AND SYNTHETIC AMINOSTEROLS IN CHICK EMBRYO AND TADPOLE ASSAYS

| Structure | Chick embryo diss. assay ($\mu$g) | Tadpole (10 $\mu$g/mL) | | | | | | Cord Formation ($\mu$g/mL) | HM MTT assay ($\mu$g/mL) | LLC MTT ($\mu$g/mL) |
|---|---|---|---|---|---|---|---|---|---|---|
| | | V | M | E | TB | GI | Mus | Tox | | |
| 1436 | 1 | + | + | ± | – | – | – | + | 6.9 | 16.7 |
| 1437 | >1 | – | – | + | – | – | – | – | | |

V = vascular; M = melanocytes, E = epithelial, TB = tissue breakdown GI = gastrointestinal, Mus = muscle, Tox = lethality at 2 hrs

TABLE III

| Structure | % Inhib. of MSI-1436 Binding @ 100 μg/mL ($^3$H-MSI-1436 at 20 μg/mL) | % Inhib of HIV (140 nM) | % PBMC toxicity (14 μM) | Rel. potency to MSI-1436 (10 mg/kg iv) Mitogen Proliferation Assay | MTT assay IC$_{50}$ μg/mL |
|---|---|---|---|---|---|
| 569 | 78 | 91 | 9 | 0.50 | 14.5 |
| 1436 | 82 | 76 | 0 | 1 | 7.8 |

TABLE III-continued
| Structure | % Inhib. of MSI-1436 Binding @ 100 μg/mL (³H-MSI-1436 at 20 μg/mL) | % Inhib of HIV (140 nM) | % PBMC toxicity (14 μM) | Rel. potency to MSI-1436 (10 mg/kg iv) Mitogen Proliferation Assay | MTT assay IC$_{50}$ μg/mL |
|---|---|---|---|---|---|
| 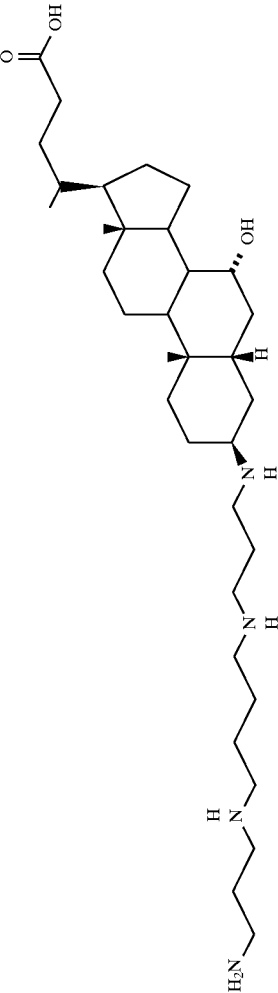 413 | −151 | 27 | 48 | 0.78 | 28 |

TABLE IV

| Structure | % Inhib. of MSI-1436 Binding @ 100 μg/mL ($^3$H-MSI-1436 at 20 μg/mL) | % Inhib of HIV (140 nM) | % PBMC toxicity (14 μM) | Rel. potency to MSI-1436 (10 mg/kg iv) Mitogen Proliferation Assay | MTT assay IC$_{50}$ μg/mL |
|---|---|---|---|---|---|
| 469 | 110 | | | 1.6 | 2.0 |
| 1437 | 14 | −44 | 0 | 1.08 | |

TABLE IV-continued

| Structure | % Inhib. of MSI-1436 Binding @ 100 μg/mL (³H-MSI-1436 at 20 μg/mL) | % Inhib of HIV (140 nM) | % PBMC toxicity (14 μM) | Rel. potency to MSI-1436 (10 mg/kg iv) Mitogen Proliferation Assay | MTT assay IC₅₀ μg/mL |
|---|---|---|---|---|---|
| 1436 | 82 | 78 | 0 | 1 | 7.8 |
| 449 | 92 | | | 0.94 | 6 |

TABLE IV-continued

| Structure | % Inhib. of MSI-1436 Binding @ 100 μg/mL (³H-MSI-1436 at 20 μg/mL) | % Inhib of HIV (140 nM) | % PBMC toxicity (14 μM) | Rel. potency to MSI-1436 (10 mg/kg iv) Mitogen Proliferation Assay | MTT assay IC$_{50}$ μg/mL |
|---|---|---|---|---|---|
| 413 | −151 | 27 | 48 | 0.78 | 28 |
| 459 | −24 | | | 0.73 | 5.0 |

TABLE IV-continued

| Structure | % Inhib. of MSI-1436 Binding @ 100 μg/mL (³H-MSI-1436 at 20 μg/mL) | % Inhib of HIV (140 nM) | % PBMC toxicity (14 μM) | Rel. potency to MSI-1436 (10 mg/kg iv) Mitogen Proliferation Assay | MTT assay IC₅₀ μg/mL |
|---|---|---|---|---|---|
| 467 | −69 | | | 0.22 | |
| 569 | 78 | 91 | 9 | 0.50 | 14.5 |

TABLE IV-continued

| Structure | % Inhib. of MSI-1436 Binding @ 100 μg/mL (³H-MSI-1436 at 20 μg/mL) | % Inhib of HIV (140 nM) | % PBMC toxicity (14 μM) | Rel. potency to MSI-1436 (10 mg/kg iv) Mitogen Proliferation Assay | MTT assay IC$_{50}$ μg/mL |
|---|---|---|---|---|---|
| 466 | 51 | | | 0.43 | 10 |

TABLE V

| % Inhib. of MSI-1436 Binding @ 100 μg/mL ($^3$H-MSI-1436 at 20 μg/mL) | % Inhib of HIV (140 nM) | Structure | % PBMC toxicity (14 μM) | Rel. potency to MSI-1436 (10 mg/kg iv) Mitogen Proliferation Assay | MTT assay IC$_{50}$ μg/mL |
|---|---|---|---|---|---|
| | 110 | 432 | | | 0.8 |
| | | 469 | | 1.6 | 2.0 |

TABLE V-continued

| % Inhib. of MSI-1436 Binding @ 100 μg/mL (³H-MSI-1436 at 20 μg/mL) | % Inhib of HIV (140 nM) | Structure | % PBMC toxicity (14 μM) | Rel. potency to MSI-1436 (10 mg/kg iv) Mitogen Proliferation Assay | MTT assay IC$_{50}$ μg/mL |
|---|---|---|---|---|---|
| | | 416 | | | 2.4 |
| | | 431 | | | 2.9 |

TABLE V-continued
| % Inhib. of MSI-1436 Binding @ 100 μg/mL ($^3$H-MSI-1436 at 20 μg/mL) | % Inhib of HIV (140 nM) | % PBMC toxicity (14 μM) | Rel. potency to MSI-1436 (10 mg/kg iv) Mitogen Proliferation Assay | MTT assay IC$_{50}$ μg/mL | Structure |
|---|---|---|---|---|---|
| −24 | | | 0.73 | 4 | 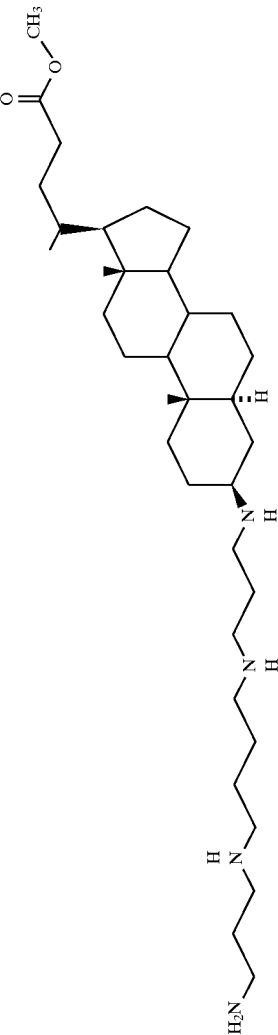 459 |
| | | | | 5.3 | 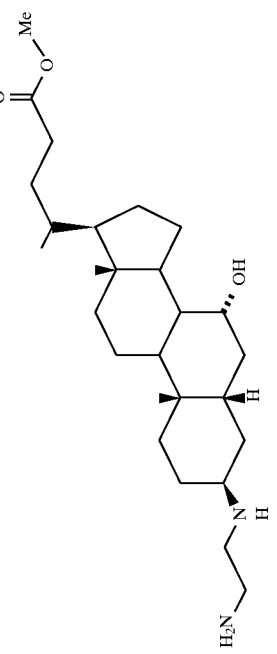 409 |

TABLE V-continued

| % Inhib. of MSI-1436 Binding @ 100 μg/mL (³H-MSI-1436 at 20 μg/mL) | % Inhib of HIV (140 nM) | Structure | % PBMC toxicity (14 μM) | Rel. potency to MSI-1436 (10 mg/kg iv) Mitogen Proliferation Assay | MTT assay IC₅₀ μg/mL |
|---|---|---|---|---|---|
| 15 | | 395 | | | 7.8 |
| 19 | | 411 | | | 7.9 |

TABLE V-continued
| % Inhib. of MSI-1436 Binding @ 100 μg/mL ($^3$H-MSI-1436 at 20 μg/mL) | % Inhib of HIV (140 nM) | Structure | % PBMC toxicity (14 μM) | Rel. potency to MSI-1436 (10 mg/kg iv) Mitogen Proliferation Assay | MTT assay IC$_{50}$ μg/mL |
|---|---|---|---|---|---|
| 32 | | 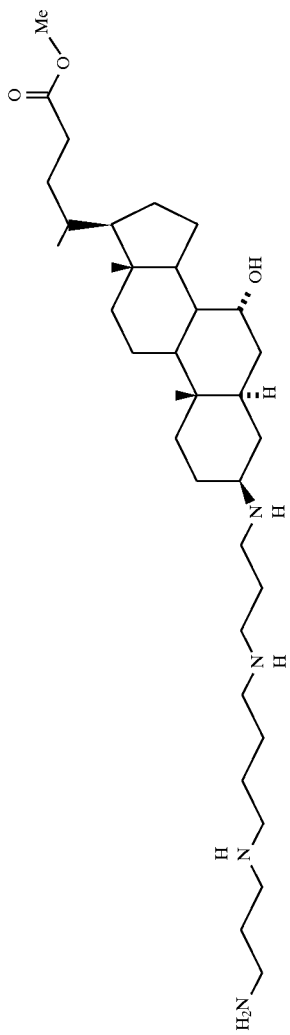 396 | | | 8.1 |
| 18 | | 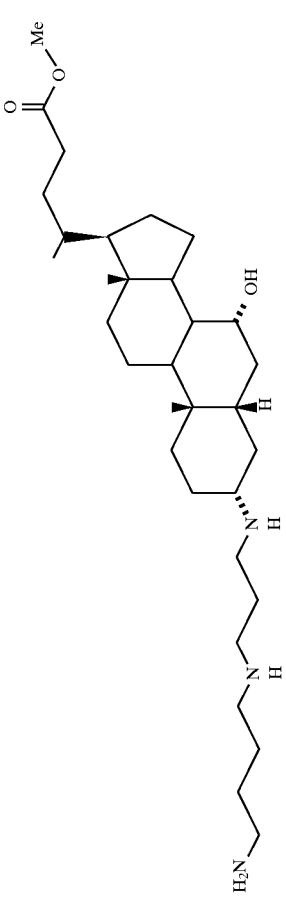 356 | | | 12 |

TABLE V-continued

| % Inhib. of MSI-1436 Binding @ 100 μg/mL (³H-MSI-1436 at 20 μg/mL) | % Inhib of HIV (140 nM) | Structure | % PBMC toxicity (14 μM) | Rel. potency to MSI-1436 (10 mg/kg iv) Mitogen Proliferation Assay | MTT assay IC₅₀ μg/mL |
|---|---|---|---|---|---|
| 57 | | (566) | | | 12 |
| 49 | | (458) | | | 13 |

TABLE V-continued
| % Inhib. of MSI-1436 Binding @ 100 μg/mL ($^3$H-MSI-1436 at 20 μg/mL) | % Inhib of HIV (140 nM) | Structure | % PBMC toxicity (14 μM) | Rel. potency to MSI-1436 (10 mg/kg iv) Mitogen Proliferation Assay | MTT assay IC$_{50}$ μg/mL |
|---|---|---|---|---|---|
| 51 |  | 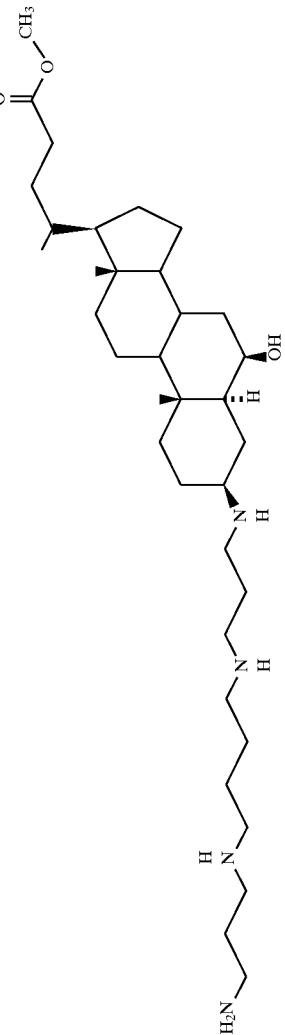 466 |  | 0.43 | 14 |
| 78 | 91 | 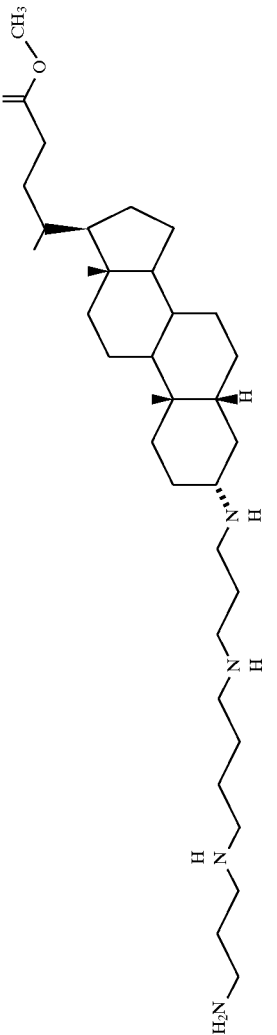 569 | 9 | 0.50 | 15 |

TABLE V-continued

| % Inhib. of MSI-1436 Binding @ 100 μg/mL ($^3$H-MSI-1436 at 20 μg/mL) | % Inhib of HIV (140 nM) | Structure | % PBMC toxicity (14 μM) | Rel. potency to MSI-1436 (10 mg/kg iv) Mitogen Proliferation Assay | MTT assay IC$_{50}$ μg/mL |
|---|---|---|---|---|---|
| 56 | | 448 | | | 20 |
| 11 | | 394 | | | 23 |

We claim:

1. An aminosterol compound according to the following formula:

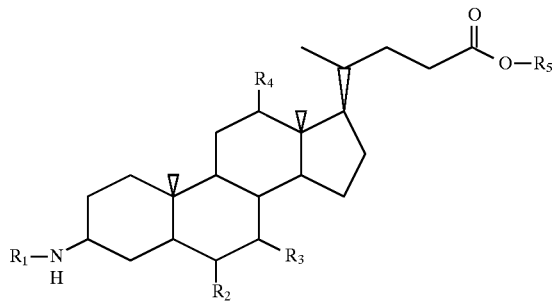

wherein:

$R_1$ is a member selected from the group consisting of:

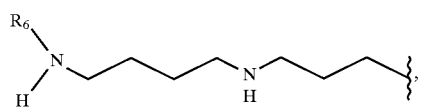

wherein $R_6$ is H or $H_2N\text{—}\!\!\!\sim\!\!\!\sim\!\!\!\sim$ ;

$H_2N\text{—}\!\!\!\sim\!\!\!\sim\text{—}N\!\!\bigcirc\!\!N\text{—}\!\!\!\sim\!\!\!\sim\!\!\!\sim$ ; and $H_2N\text{—}\!\!\!\sim\!\!\!\sim\!\!\!\sim$ ;

$R_2$ is H or OH;

$R_3$ is H or OH;

$R_4$ is H or OH; and $R_5$ is a $C_1$ to $C_{12}$ alkyl group.

2. An aminosterol according to claim 1, wherein $R_5$ is a methyl group.

3. An aminosterol compound according to claim 1, wherein the compound is

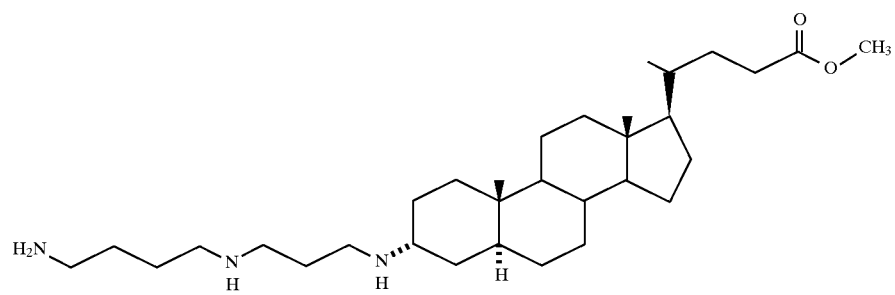

4. An aminosterol compound according to claim 1, wherein the compound is

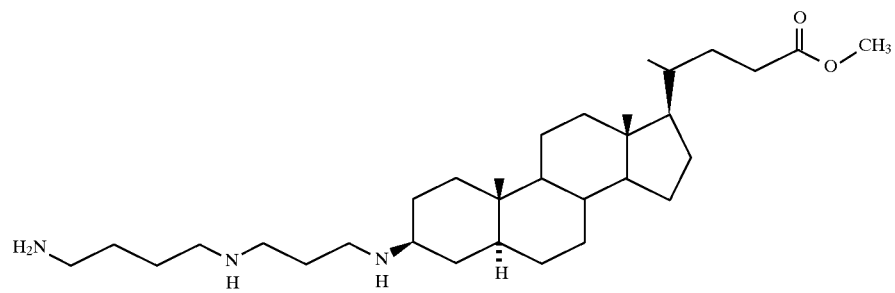

5. An aminosterol compound according to claim 1, wherein the compound is

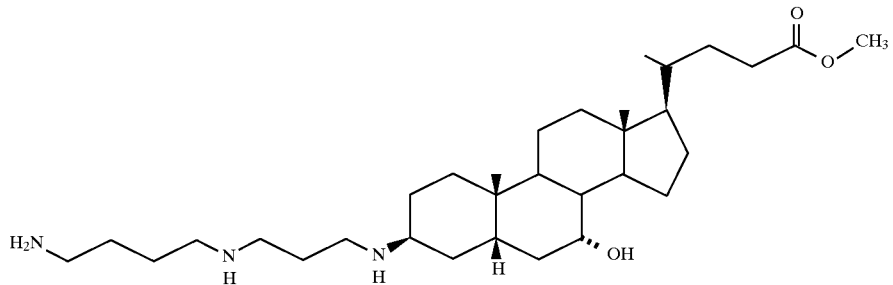
6. An aminosterol compound according to claim 1, wherein the compound is
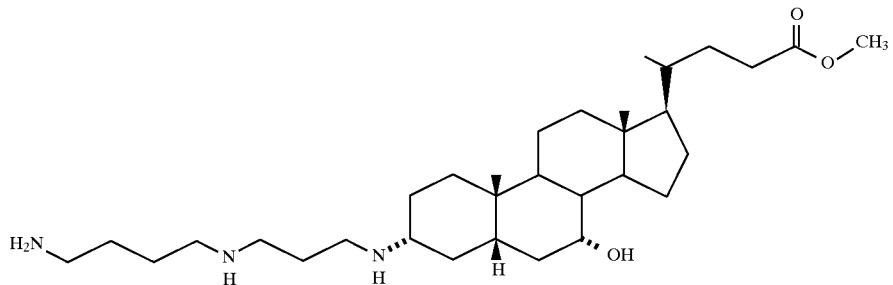
7. An aminosterol compound according to claim 1, wherein the compound is
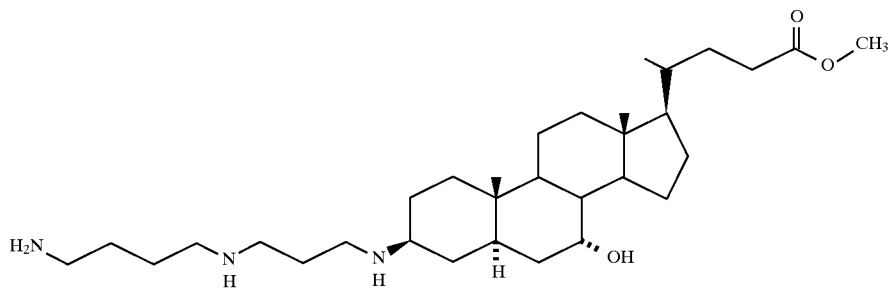
8. An aminosterol compound according to claim 1. wherein the compound is
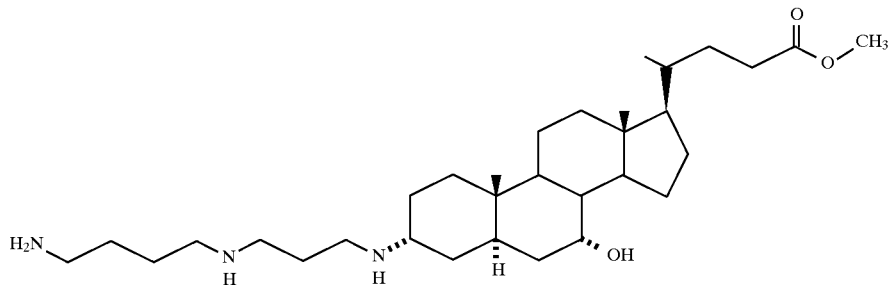
9. An aminosteroi compound according to claim 1, wherein the compound is

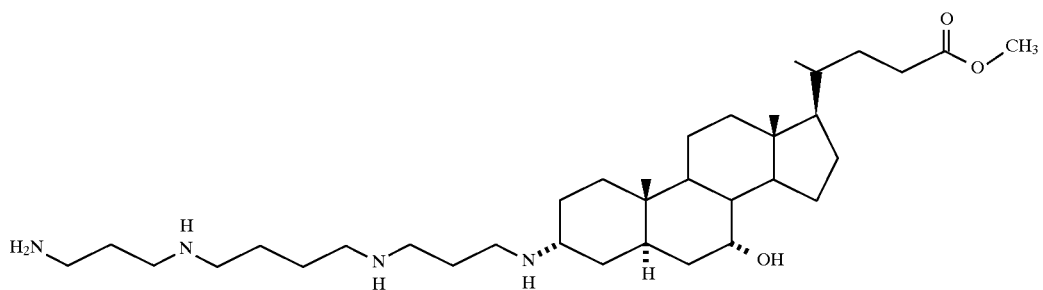
10. An aminosterol compound according to claim 1, wherein the compound is
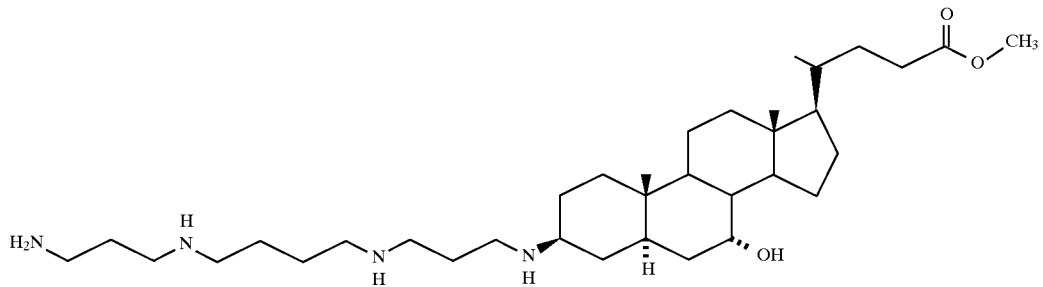
11. An aminosterol compound according to claim 1, wherein the compound is
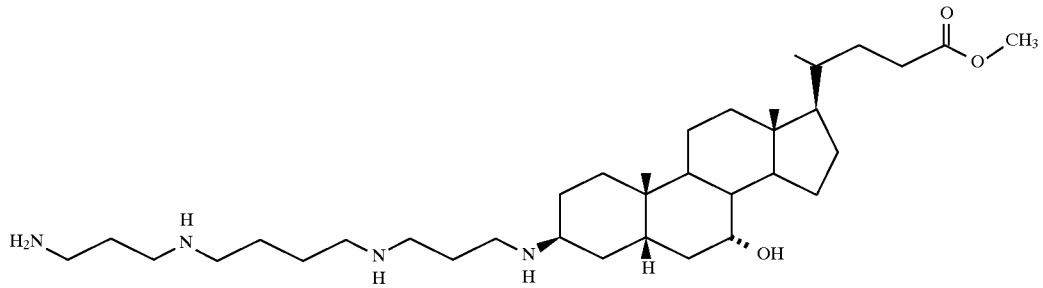
12. An aminosterol compound according to claim 1, wherein the compound is
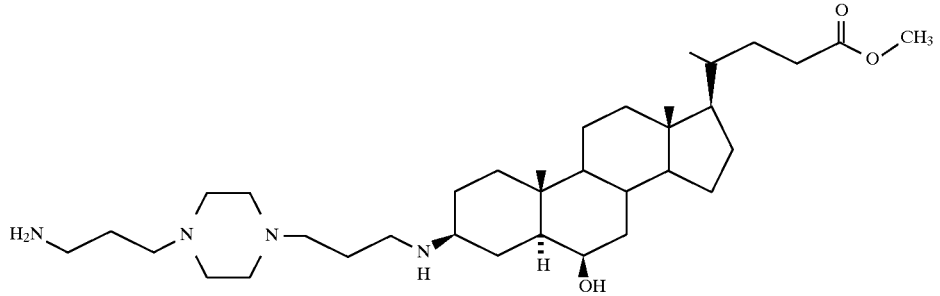
13. An aminosterol compound according to claim 1, wherein the compound is

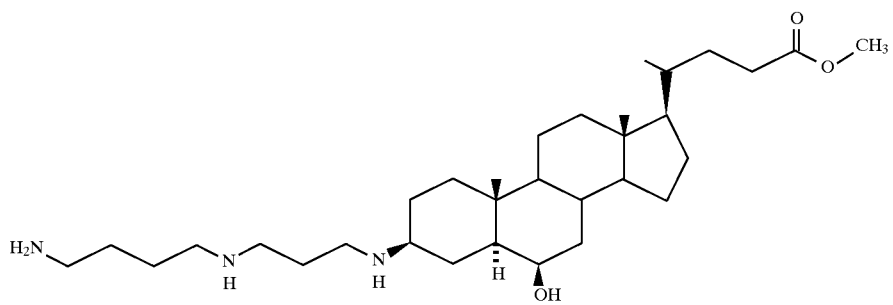
14. An aminosterol compound according to claim 1, wherein the compound is
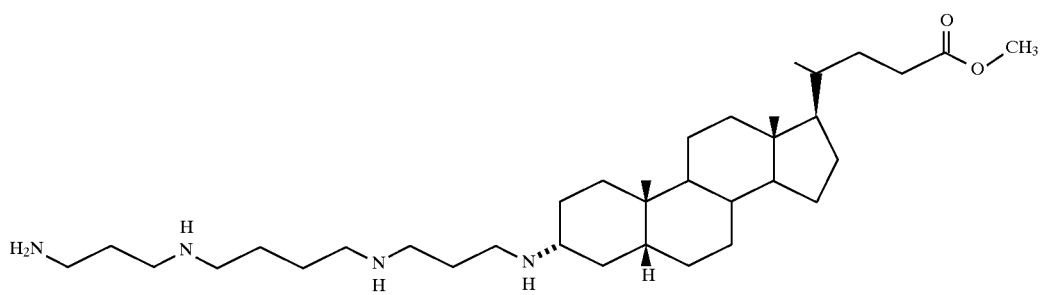
15. A pharmaceutical composition comprising:
an aminosterol compound according to claim 1 or a pharmaceutically acceptable salt thereof; and
a pharmaceutically acceptable carrier or excipient.
* * * * *